United States Patent
Perea-OcHoa

(10) Patent No.: US 12,089,733 B2
(45) Date of Patent: Sep. 17, 2024

(54) THERAPEUTIC MULTI-TASK HAND SUPPORT DEVICE

(71) Applicant: Jesus Perea-OcHoa, Montebello, CA (US)

(72) Inventor: Jesus Perea-OcHoa, Montebello, CA (US)

( * ) Notice: Subject to any disclaimer, the term of this patent is extended or adjusted under 35 U.S.C. 154(b) by 1120 days.

(21) Appl. No.: 16/514,856

(22) Filed: Jul. 17, 2019

(65) Prior Publication Data

US 2021/0015252 A1 Jan. 21, 2021

Related U.S. Application Data

(60) Provisional application No. 62/721,588, filed on Aug. 22, 2018.

(51) Int. Cl.
*A47B 21/03* (2006.01)

(52) U.S. Cl.
CPC .. *A47B 21/0371* (2013.01); *A47B 2021/0392* (2013.01); *A47B 2200/0091* (2013.01)

(58) Field of Classification Search
CPC ........ A47B 21/0371; A47B 2021/0392; A47B 2200/0091; A61F 5/0118
USPC ................... 248/118.3, 118, 118.1; 434/227; 400/715
See application file for complete search history.

(56) References Cited

U.S. PATENT DOCUMENTS

| | | | | |
|---|---|---|---|---|
| 84,844 A | * | 12/1868 | Sangalli | G09B 15/06 84/469 |
| 591,800 A | * | 10/1897 | Westin | G09B 15/06 84/469 |
| 794,042 A | * | 7/1905 | O'Connor | A47B 21/0371 248/118.3 |
| 1,359,928 A | * | 11/1920 | Lewis | G09B 15/06 84/469 |
| 5,050,826 A | * | 9/1991 | Johnston | A47B 21/0371 400/715 |
| 5,082,258 A | * | 1/1992 | Niks | A63B 23/16 601/40 |
| 5,108,057 A | * | 4/1992 | Dandy, III | B41J 5/08 248/118 |

(Continued)

FOREIGN PATENT DOCUMENTS

DE 4025143 A1 * 2/1992
KR 200201619 Y1 * 11/2000

*Primary Examiner* — Kimberly T Wood
(74) *Attorney, Agent, or Firm* — David & Raymond Patent Firm; Raymond Y Chan

(57) ABSTRACT

A hand support device, for an input apparatus such as typing apparatus like keyboard, notebook, laptop, or the like, includes an elongated hand supporting bridge unit, a support base assembly and a pillar and bar joint assembly. The support base assembly supports the hand supporting bridge unit directly over the keyboard along the keyboard from the right side to the left side of the keyboard so that the user can rest on and work, wherein the support base assembly comprises a first base unit and a second base unit adapted for positioning at two sides of the keyboard. The pillar and bar joint assembly is to arranged to movably support by the first base unit and the second base unit in order for the hand supporting bridge unit to provide a transversal support for the user's upper extremities over the keyboard.

23 Claims, 29 Drawing Sheets

(56) References Cited

U.S. PATENT DOCUMENTS

| | | | | |
|---|---|---|---|---|
| 5,161,760 | A | * | 11/1992 | Terbrack ............... G06F 3/0202 345/157 |
| 5,386,957 | A | * | 2/1995 | Miller ................ A47B 21/0371 248/118.5 |
| 5,478,034 | A | * | 12/1995 | Cunningham ........... B41J 29/00 248/118.5 |
| 5,635,955 | A | * | 6/1997 | Maynard, Jr. ........... G06F 3/023 345/184 |
| 5,685,719 | A | * | 11/1997 | Bressler .................... A61F 4/00 108/103 |
| 6,691,972 | B1 | * | 2/2004 | Oliver .................... A47B 97/04 248/118.5 |
| 10,054,980 | B2 | * | 8/2018 | Strieby ................. G06F 1/1632 |
| 2004/0007651 | A1 | * | 1/2004 | Williams ............... F16M 13/00 248/346.06 |

\* cited by examiner

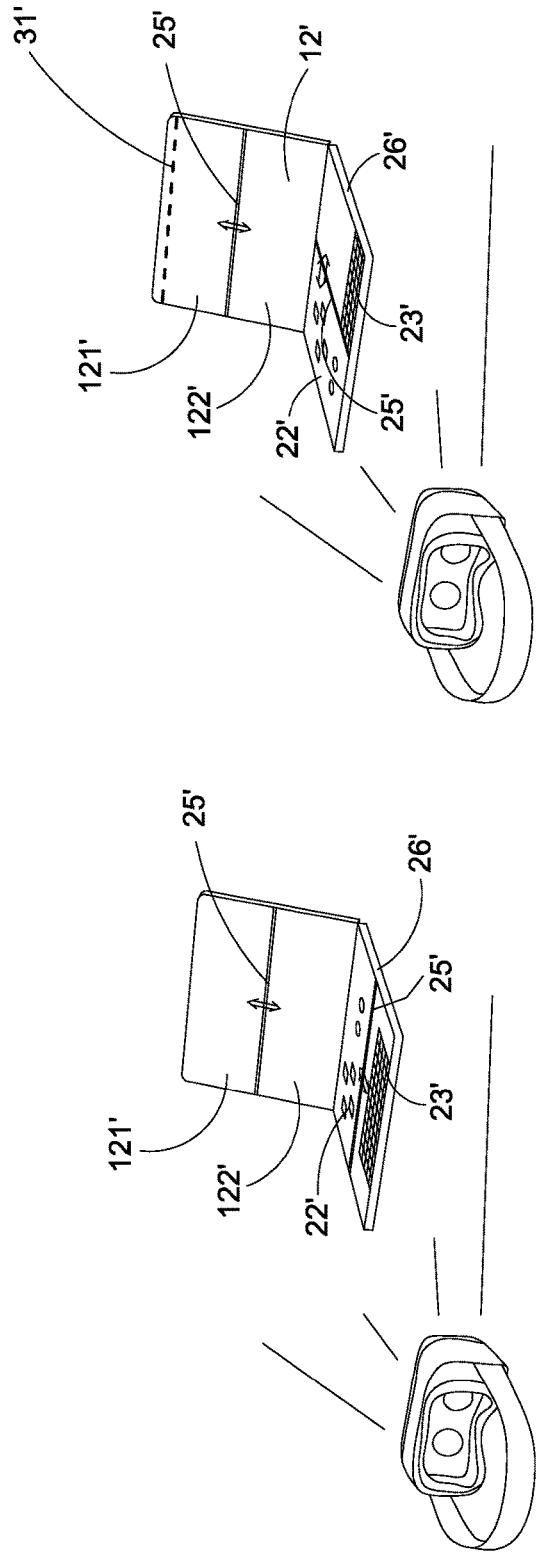
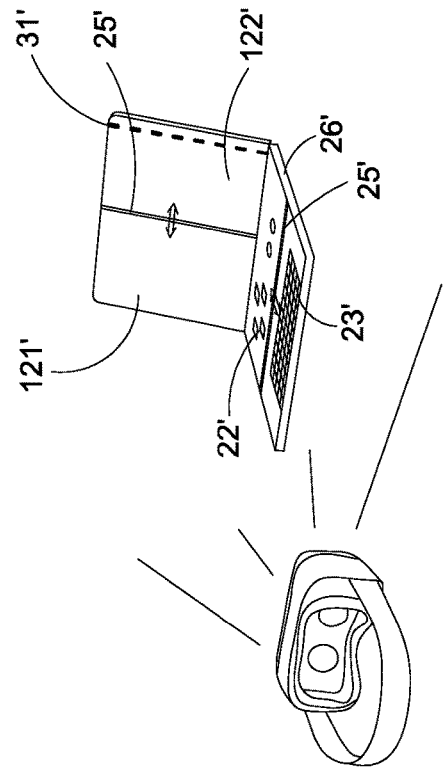
FIG.39A
FIG.39B
FIG.39C

THERAPEUTIC MULTI-TASK HAND SUPPORT DEVICE

CROSS REFERENCE OF RELATED APPLICATION

This is a non-provisional application that claims the benefit of priority under 35 U.S.C. § 120 to a provisional application, application No. 62/721,588, filed Aug. 22, 2018. The afore-mentioned provisional application is hereby incorporated by reference in its entirety.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to hand support device for an input apparatus such as input apparatus such as typing apparatus like keyboard like keyboard, laptop accessory and/or built-in system thereof, and more particularly to a hand support device, adapted for operating in a multi-task interactive system, providing assistance, support and therapeutic treatments to the typist while working on an input apparatus like keyboard, laptop or other communication input apparatus, or gaming device, including augmented reality devices (AR) and/or virtual reality devices (VR) for the purpose of the user supporting his or her uppers extremities, in particular hands and wrist during repetitive task and or for prolong cervical spine muscular posture tension, in a wrist support typing posture.

Description of Related Arts

With the continuous development of new computer applications and functions, people are increasingly unable to give up the computer. Almost all people work on the computer to type, like editing codes, writing reports, sending emails or accessing to information, etc. In other words, the office worker may always sit in the office and spend all working time to type with a keyboard or laptop. The reports say that people are sitting in an average of 9 hours a day, 60% of which are at work facing the computer, which is harmful to the health of people, especially when people sit in a wrong posture. All computing devices like laptops, keyboards computers gaming devices, (AV/AR) devices, communication devices, require a particular level of humans physical effort and stamina to produce a task and for enjoyment.

When people sit and type, they need to withstand a muscle fatigue due to gravitational forces and an opposed support of the chair and the desk, and an alignment force which forces people to face the computer in a fix posture. Gravity and lack of physical endurance preset most people to sit in the wrong posture while typing, their cervical vertebras are in the wrong posture of forward flexion and their muscles of the posterior neck are also strained due to long-term inflexibility, causing cervical spondylosis. At the same time, prolong poor ergonomic sitting and typing posture can cause gravity and weight to be pressed against a thoracic lumbar region, wherein a pressure bearing surface is unevenly distributed, which causes a kyphosis and the waist, abdomen and back muscles to sag and produce pain. Teenagers whose spines and neck are in a growth should pay more attention to above problems. Due to a variety of homeworks, computer games and projects the teenagers spend lots of time in a compromise positional posture, which is not less than the office worker.

It is important and necessary to maintain a correct sitting and typing position while using the computer. When we sit and type, our hands will rise high in the air over the keyboard which even time fatigue causes the wrong siting and typing posture, especially our cervical vertebra in a wrong state of forward flexion. Even if our elbows and forearms are supported, these problems will not be solved.

It is important to mention prolong (AR/VR) utilization will lead to numerous orthopedic stress injuries and additionally the physical kinetic energy requirement will be too demanding for the general public. The computer keyboard platform will not get replace by the (AR/VR) technology but the (AR/VR) technology will enhance the keyboard computer platform. In other words, our invention will physical support the upper extremities and technologically interacted with typing computing apparatus that will interact with multiple systems of electronic devices and computer programs including (AR/VR) technology.

In addition to the hunchback and the cervical spondylosis, the poor sitting and typing posture also causes thoracic enthesopathy, upper crossed syndrome which manifests as inhibited neck flexors, inhibited rhomboids and serratus anterior, tight deltoid and tight upper trapezius and levator scapulae muscles, and tension headache can all manifest with or without (AR/VR) device utilization.

Continues over utilization of the computer has been linked to increase insomnia. Insomnia can increase depression and disrupt the normal circadian rhythm. Our goal is to provide a hand wrist support that works in conjunction with other FDA approved modalities to deliver a system of wellness during work hours, or recreational time. The user will be able to use computers, laptops, keyboards, augmented reality and virtual reality devices all while the hand and wrist are supported and the support device delivers additional medical therapeutic care.

During physical demand on a specific body part over utilization of the muscles will cause soreness and strain, while maintaining the correct sitting and typing posture without any auxiliary equipment for a long time. And some people may not know the correct sitting and typing posture, or the wrong sitting and typing posture has been their habit which is incorrigible behavior. In other words, it is toilsome for people to maintain the correct sitting and typing posture without any auxiliary equipment.

Furthermore, even with the proper auxiliary equipment millions of people around the world live and work with chronic pain and mental health needs. At the same time around the word the dependence on the over utilization of computers or similar devices has increases exponentially. No other hand wrist supporting system provides Tens unit, Interferential therapy (IF), H wave therapy, Microcurrent Electrical Therapy (MET), where the user and/or the medical provider can designate the proper required treatment modalities on the internet/intranet. Where the medical provider and the patient may monitor the treatment and control the duration, intensity and strength of the applicable medical care. In other words, the medical provider will have direct contact with the patient through the internet or intranet.

Furthermore, no conventional hand wrist support encompasses a system where the structural support houses an array of multiple various medical treatments. In other words, the user buys a specific treatment cartridge with specific connecters designated for a specific treatment to be operated by the hand therapeutic support device for the specific illness that is being treated. Additionally, the treatment controls can be on the hand therapeutic support device, cell phone, physical computer, laptop, AR/VR, or on the keyboard. Were the hand wrist support system can be also be control through the internet, intranet and to include a computer application (AP) and not exclusive to any combination.

Multiple illnesses like Raynaud's disease, neuromuscular disease, chronic and acute neuropathic pain, nociception pain, carpal tunnel syndrome, sprain, strain, tendinitis, arthritis, gout, pseudogout or other injuries of the hand can affect mental health like tress, depression, anxiety and insomnia. Additionally, with illness and fatigue proprioception is diminish reducing the user's ability to complete typing task.

In addition, most electronic devices are powerful enough to run two applications at the same time for multi-tasking. For example, the player is able to play via a game application and chat with friends via another chat application. However, these applications are controlled by one single input. In other words, when the player wants to control the game, he or she must switch the input corresponding to the game application. When the player wants to chat with friends, he or she must switch the input back to the chat application from the game application. This switching manner will interfere the flow of the game and the chatting as well.

Such switching burden also exists in processing software applications and/or computer languages, such as processing a word or graphic document, by opening one window and chatting with friends with a communication software or APP by opening another window. The user is required to switch between the windows from time to time too. Specially in users with physical medical tremors, it can be severely limiting to operate programs like these that require continues dexterity without any hand therapeutic support device.

SUMMARY OF THE PRESENT INVENTION

The invention is advantageous in that it provides a keyboard, laptop, or other input apparatus such as typing apparatus like keyboard a hand support device, which provides assistance and support for a user to rest his hands and wrists, so that the user needs less efforts while input working like typing and repetitive fingers or wrist movements while additional therapeutic modalities can be provided.

It is an advantage of the invention in that it provides a hand support device which not only support and treat existing injuries but also provide treatment prophylactically for a better quality of life.

One advantage of the invention is to provide a hand support therapeutic multi-task device that the users have the option to purchase interchangeable therapeutic cartridges for equipping with the hand support therapeutic multi-task device. The user will be able to buy any electrotherapeutic modality and administer more than one therapeutic modalities on multiple body parts at the same time through the use of the hand support therapeutic multi-task device.

Another advantage of the invention is the parallel adjustable bar or bars of the hand support device adapted for running over the input apparatus such as typing apparatus like keyboard, on the side or underneath the input apparatus such as input apparatus such as typing apparatus like keyboard like keyboard, computer, laptop or gaming device. The hand support device of the invention is able to give the user meaningful structural stability hovering over the input apparatus with minimal effort. In other words, existing hand support structures are elementary and lack adjustments specifications that are different to every individual needs. Traditionally current hand supports are made of nylon, cloth rubber soft material and all existing hand supports are located distal to the keyboard or laptop demanding the user to hyperextend all digits to overcome the separation between the input apparatus such as input apparatus such as typing apparatus like keyboard and the hand wrist support, wherein the hand of the user has to bent upwardly from his or her wrist to a up bending typing posture that substantially hurting the wrist for long time typing with such posture. In addition, the lack of available adjustments on current existing hand support compounds the problem. This problem is exceptionally evident with the existing traditional hand/wrist matt support and current laptop combination where the user will continue to experiencing discomfort.

Another advantage of the invention is that while the bar or bars are supporting the hand and wrist at the same time the typist is able to be given multiple types of Food and Drug administration (FDA) approved treatments like electrotherapy treatment, iontophoresis treatment, topical treatments, compound medications and occlusion therapy, these are well known treatment modalities, where currently patients must stop activities on the computer or keyboard activities to enable acquisition of such medical care. According to the present invention, the user will be able to get all treatment modalities without stopping their computer activities.

Another advantage of the invention is to provide a hand support device for input apparatus such as typing apparatus like keyboard or laptop, providing assistance and support for a user to rest his hands and wrists and type with a wrist support typing posture that the hands of the user are naturally handing down from his or her wrists to reach the typing apparatus to type, while the wrists are well supported by the hand support device, so that the user needs less efforts while working like typing and repetitive fingers or wrist movements while provided additional therapeutic modalities.

Another advantage of the invention is to provide a hand support device for input apparatus such as typing apparatus like keyboard, notebook or laptop, which supports the hands of the user to promote the user to sit and type in a correct posture and avoid poor cervical vertebra posture alinement and reduce straining the upper extremities due to a wrong posture of forward flexion. In other words, the user needs less efforts in maintain the correct sitting and typing posture with the hand support device.

Another advantage of the invention is to provide a hand support device for input apparatus such as typing apparatus like keyboard, notebook, laptop, or the like, which helps the user with upper extremities injuries to work or play on the keyboard, laptop or computer. In other words, the hand support device is arranged to better support the injured hands or wrists of the user and enable the hands of the user naturally hanging down from his or her wrists which are well supported by the present invention to helps reduce pain exacerbation from over compensating due to the pre-existing injury while enabling natural, easy and smooth movement of the hands and fingers during typing.

Another advantage of the invention is to have interchangeable therapeutic cartridges kits adaptable to a hand support device for specific medical and prophylactic care. Where the controls for the therapy can also be interchangeable on the hand support device, computer monitor, laptop monitor, keyboard, AR/VR and on the users smart phone internet and or intranet computer application.

Another advantage of the invention is to provide a hand support device for input apparatus such as typing apparatus like keyboard, notebook, laptop, or the like, which radiates heat or cold, and/or frequency vibration to the fingers, hands and wrists of the user.

Another advantage of the invention is to provide a hand support device for input apparatus such as typing apparatus like keyboard, notebook, laptop, or the like with radiates a magnetic field for therapy and diagnostics.

Another advantage of the invention is to provide medicine and electrotherapy to the user of a hand support device while the user is engaging in work, and personal activities on input apparatus such as typing apparatus like keyboard or laptop. In other words, the bars can provide the source of contact for topical medicine, and electrotherapy, and further more the hand support therapeutic device can provide additional leads, pads, patches, and braces etc. for a more complete body care.

Another advantage of the invention is to provide various types of gloves, straps and bracing for comfort and to deliver various treatments modalities of a hand support device for input apparatus such as typing apparatus like keyboard, notebook, laptop, or the like.

Another advantage of the invention is to provide a hand support device for input apparatus such as typing apparatus like keyboard, notebook, laptop, or the like which comprises an additional wrist brace on to the bar or bars for additional added support, treatment and comfort.

Another advantage of the invention is to provide a portable adaptable or built in input apparatus such as typing apparatus like keyboard hand support device to any electronic computing device, which the user can move to a desire location for additional comfort.

Another advantage of the invention is to provide a hand support device for input apparatus such as typing apparatus like keyboard, notebook, laptop, or the like, which enables the user having micro movements in all directions while hovering over the input apparatus such as typing apparatus like keyboard at a desire location.

Another advantage of the invention is to provide a hand support device for input apparatus such as typing apparatus like keyboard, notebook, laptop, or the like, which provides an up and down motion support, a left to right distance support, and oblique angles left to right horizontal plane reaching support and a bilateral vertical angular finger distant position supporting to facilitate a support control.

Another advantage of the invention is to provide a hand support device for input apparatus such as typing apparatus like keyboard, notebook, laptop, or the like, comprising a bar or set of bars under, over or on the side for the support of the users hands and to mount an additional hand wrist brace for additional support and treatment options.

Another advantage of the invention is to provide a hand support device for input apparatus such as typing apparatus like keyboard, notebook, laptop, or the like, adapted for the bar, bars, and or the additional hand wrist support to work in conjunction with hand gloves, elbow brace and other support for the purpose of treating the user illness.

Another advantage of the invention is to provide a hand support device to provide additional multiple therapeutic leads for additional body parts and where the treatment can be the same or different from the upper extremity on going treatment modality, at the same time.

Another advantage of the invention is to provide a hand support device for input apparatus such as typing apparatus like keyboard, notebook, laptop, or the like, which provides the desire adjustable positions for comfort in relation to the upper extremities, such as the plantar surface, volar medial, lateral carpal and metacarpal region of both wrists.

Another advantage of the invention is to provide a hand support device for input apparatus such as typing apparatus like keyboard, notebook, laptop, or the like, which will minimize upper extremities energy consumption and maximizes productivity, additionally one can overcome complex time consuming work or games, through the use of the hand support device on the upper extremities.

Another advantage of the invention is to provide a hand support device for input apparatus such as typing apparatus like keyboard, notebook, laptop, or the like, wherein a plurality of sleeves can be manufactured and provided for additional sliding motion, pressure support, topical medications and several additional medical treatments. Like hypoallergenic sleeves to decreasing contact dermatitis etc.

Another advantage of the invention is to provide a hand support device, which is adapted for a pre-existing keyboard, notebook or laptop.

Another advantage is to provide the existing keyboard a build in premanufactured portable collapsible hand support device accessory.

Another advantage is to provide the existing laptop a build in premanufactured portable collapsible hand support device accessory.

Another advantage is to provide a center midline alphabetic system and numeric system input apparatus such as typing apparatus like keyboard that will have a symbiotic utilization for the hand support device as an accessory or as a single unit in other words the key lettering and numbers on the input apparatus such as typing apparatus like keyboard will be center in relation to the hand support device.

Another advantage is to provide future keyboard, laptops and computers a build-in premanufactured diagnostics and recordings of temperature, heart rate, blood pressure, therapy duration, intensity and level of function.

Another advantage of the invention is to provide a hand support device for input apparatus such as typing apparatus like keyboard, notebook, laptop, or the like, which can be used for military applications for the soldier to have vital muscular skeletal support system to enable immediate and prolong communication and for the overall clerical cyber keyboard demands of military duties.

Another advantage of the invention is to provide a hand support device for input apparatus such as typing apparatus like keyboard, notebook, laptop, or the like, which can be operational in the battle fields as well in the support units for the purpose of providing our soldiers the very best equipment with the latest technology break throughs to complete the mission. In the support units, soldiers are expose to long hours, tedious repetition, and are required to have sharp focus reaction to both incoming threats and during ongoing offensive attacks. The hand support device provides the soldier a support system for the wrist, hands, shoulder and throughout their body without restricting the natural movement of the soldier upper and lower extremities, while maximizing the user productivity time and response time.

Another advantage of the invention is to provide a hand support device for input apparatus such as typing apparatus like keyboard, notebook, laptop, or the like, which reduces the soldier muscular fatigue on bilateral upper extremities by providing the soldier direct support over the keyboard all while the user is in a natural neutral position. Through the hand support device, the user can take a break, like a posture stretch, all while maintaining tactile contact with the keyboard to reacted and act on any threat in less than a second notice. It is importance to emphasize the importance of hovering over the keyboard during critical tactical moment in war for immediate response time. In the past, soldiers fighting fatigue had to completely remove their upper extremities away from the keyboard in order to ensure not to produce erroneous information, or even worse accidently destroy the mission.

Another advantage of the invention is to provide a hand support device for input apparatus such as typing apparatus like keyboard, notebook, laptop, or the like, wherein while the user is at rest no other hand support device provides the soldiers an unsurpassed ability to immediately scramble during long cycles of down time giving the user the ability to produce immediate commands, responses or codes. Presently a soldier would have to completely remove their hands/wrist off the keyboard in order to alleviate posture tiredness. The time it takes to reposition from a brake like this, of removing the hands and arms away from the keyboard, induce a upper extremity posture stretch, and back on to the same keyboard, are precious minutes lost in the battle field that can mean life or death scenarios.

Another advantage of the invention is to provide a hand support device for input apparatus such as typing apparatus like keyboard, notebook, laptop, or the like, wherein military support units benefit from the hand support device in relation to the physical time demands requirement on the soldiers. In other words, one can go minutes to hours without any action and soldiers can easily get distracted during long time-outs. Where soldiers are forced to endure chronic fatigue and at the same time are require to spontaneously generated typing transcriptions on command, where speed and reaction are essential to the mission.

Another advantage of the invention is to provide a hand support device for input apparatus such as typing apparatus like keyboard, notebook, laptop, or the like, wherein other scenario is during short critical times that are adrenalin driven the soldiers can become exponentially exhausted without realizing. This will leaded to increase risk of human errors where time is not the directed contributor to the soldier fatigue and where psychological immediate situational stressors are the directed source of fatigue on to the soldier. The more mental stressors like multi-tasking on the individual the greater the physical fatigue the soldier will experience. Anxiety, insomnia, PTSD, MDD, and stress along with physical fatigue are cumulative malignant factors in relation to combat deployment and can manifest into tremors and erode the linguistic utterance demands required to communicated in order to win a war. In other words, the stressors of war can produce upper extremity tremors reduce dexterity and thereby reduces any soldier efficiency, and that is the biggest sympathetic response problem all humans must overcome during immediate emergency scenarios. The hand support device of the present invention provides the support to improve upper extremity dexterity and reduce upper extremity mental transient physical movements thereby improving typing on the keyboard during time of crisis.

Another advantage of the invention is to provide a hand support device which is the interactions in relation to the VR/AR technology for example while in a moving vehicle a soldier will be able to type and read their messages on the AR/VR system all while maintaining visual surveillance for enemies from the inside of the vehicle.

Another advantage of the invention is to provide a hand support device for input apparatus such as typing apparatus like keyboard, notebook, laptop, or the like, which enables soldiers being more productive just in general whether they had a sleepless night before, or where out drinking late last night, or suffered from headaches, or have a common cold, the user will have the ergonomic option to utilize a support device on their hand and wrist while providing additional therapy throughout their body at work for longer and faster work production.

Another advantage is to provide a method and system of operating multi-task interactive electronic devices with an attached or a detached hand support deice as an accessory built in or adaptable.

Another advantage is to provide sports betting as a function of and electronic device with a hand therapeutic support device of the present invention.

Another advantage is to provide a multiple gaming devices with a hand therapeutic support device, where the user can select from various therapeutic options, while gaming.

Another advantage of the present invention is to provide a method and arrangement of operating multi-task interactive electronic device with a hand support device for playing games or processing software's or applications such as processing word or graphic documents, in which the user is able to control at least two applications simultaneously by at least two input modules in a real time manner without interfering with the applications on an electric device.

Another advantage of the present invention is to provide a method and arrangement of operating multi-task interactive electronic devices with a hand support device, including but not limited to augmented reality and virtual reality (AR/VR) devices, working independently or in conjunction with at least an electronic device for playing games or processing softwares or applications such as processing word or graphic documents, in which the user is able to control at least two applications simultaneously by at least two input modules in a real time manner without interfering the applications.

Another advantage of the present invention is to provide a method and arrangement of operating multi-task interactive electronic device(s) with a hand support device for playing games, wherein the players of the game are able to remotely play the selected game while being able to play against one or more of other real players playing through the communication network in a real time manner.

Another advantage of the present invention is to provide a method and arrangement of playing games or processing softwares or applications such as processing word or graphic documents in an electronic device with a hand support device, wherein the players or users are able to play the games or process the softwares or applications anywhere anytime via remotely linking the individual electronic devices to the communication network.

Another advantage of the present invention is to provide a method and arrangement of playing games or processing softwares or applications, wherein the players or users are able to remotely play the game or process the software or application while communicatively chatting with other real players or users through the communication network of an electronic device with a hand therapeutic support device.

Another advantage of the present invention is to provide an arrangement of operating multi-task interactive electronic devices with one or more hand support devices for playing games, wherein the communication network of the casino is able to link to a plurality of individual electronic devices with hand support devices, such as slot machines, electronic roulettes, and electronic poker games, so that the players are able to remotely bet or play the gambling game against another real player and/or the dealer, which may be the machine, via the individual electronic devices with hand support devices through the communication network. Therefore, the players have no need to physically go to the crowded gambling table of the table type games or sit in front of the machines while being able to play against the real players.

Another advantage of the present invention is to provide a method and arrangement of operating multi-task interactive electronic devices with a hand support device for playing games, wherein the player is able to active a sideline program for operating multi-task while interacting with one or more electronic devices by inputting membership information such as by inserting a membership card which may digitally store the player information and the prepaid money therein or by means of face or fingerprint recognition to verify the player's information and open the player's prepaid money account stored in the central control of the host of the game, such as the casino, for actuating the games. Thereby, the arrangement may also eliminate the precisely and accurately counting process of physical cash or betting chips after each round of the betting or wagering of the game, so as to enhance the security of the casino and players. Accordingly, the arrangement will be designed primarily for the use of the guest of an establishment such as a hotel. Gambling atmosphere will be fully provided for the establishment guest to play the game anywhere.

Another advantage of the present invention is to provide a method and arrangement of operating multi-task interactive electronic device(s) with a hand support device for playing game, wherein the information of the player, including credit card information and personal information, will be encrypted and stored, such tokenization, for enhancing the data security.

Additional advantages and features of the invention will become apparent from the description which follows, and may be realized by the following description of the instrumentalities and combinations particular pointing out in the appended claims.

According to the present invention, the foregoing and other objects and advantages are attained by providing a hand support device for an input apparatus such as typing apparatus like keyboard, notebook, laptop, or the like, which comprises:

an elongated hand supporting bridge unit;
a support base assembly, wherein the support base assembly supports the hand supporting bridge unit directly over the keyboard along the keyboard from the right side to the left side of the keyboard so that the user can rest on and work, wherein the support base assembly comprises a first base unit and a second base unit adapted for positioning at two sides of the keyboard; and
a pillar and bar joint assembly, which is arranged to movably support by the first base unit and the second base unit in order for the hand supporting bridge unit to provide a transversal support for the user's upper extremities over the keyboard.

The pillar and bar joint assembly comprises a first pillar and bar joint and a second pillar and bar joint respectively arranged at the first base unit and the second base unit.

The hand supporting bride unit comprises one or more elongated bars, preferably a pair of parallel bars, wherein the bars is supported between the first pillar and bar joint and the second pillar and bar joint which are positioned respectably on opposite side of the keyboard.

At the same time the bars sitting over the keyboard, the user can control the desire direction for comfort thereof. In other words, the hand supporting bridge unit provide an upward and downward motion support, a left to right distance support, and oblique angles left to right horizontal plane reaching support and a bilateral vertical angular finger distant positioning support. Preferably, the hand supporting bridge unit sits over the keyboard where the height is adjustable for the different users to work and rest. Additionally, the hand supporting bridge unit can be under or on the side of the input apparatus such as typing apparatus like keyboard to support a brace visa versa as another example.

In one embodiment, the hand supporting bridge unit comprises one or more elongated bars. It is important to mention the bar or bars can be of any shape like hollow bars, I beam, L beam, C channel, U channel, formatted truss etc.

In one embodiment, the present invention provides an arrangement of playing games, which comprises:
a plurality of individual electronic devices with hand support devices respectively for being activated by at least one player of the game to controllably and selectively play games therethrough; and
a networking system electrically linking to each of the individual electronic devices with hand support devices and being accessible by at least one casino for managing the arrangement of playing games, wherein the communication network system comprises:
a communication network, which comprises an information storage for storing at least one of the player's information therein, and a plurality of game programs stored in the communication network; and
a remote connecting module for electrically linking the individual electronic devices with a hand support devices with the communication network to form the networking system, so that when the player controllably activates the individual electronic device with hand therapeutic support devices in an authorized manner to electrically link the communication network through the remote connecting module, the player is able to play the casino games in a remotely gambling manner.

In one embodiment, the game players may activate the individual electronic devices with hand support devices thereof by inputting a membership information, for example, via a membership card provided by the casino, so that when the membership card is electrically connected to the individual electronic device with a hand support devices to authorize the player accessing the computer program for the communication network of the casino, the player is able to selectively play the games for betting or wagering.

In one embodiment, the communication network further comprises an online chatting program electrically linking with the remote connecting module, so that the players are able to remotely play the games against or with other real players while being able to chat with other players in a real-time manner. Therefore, the arrangement of playing game does not require the players physically go to the gambling table, and meanwhile, provides the players remotely play against or with other real players in a real-time manner.

In one embodiment, the communication network may be wirely or wirelessly linked to the individual electronic device with a hand support device in the remote control manner. In other words, the individual electronic devices with a hand support device are able to access communication network remotely, preferably, within a predetermined distance.

In accordance with another aspect of the invention, the present invention provides a method of operating a multi-task interactive electronic devices with hand support devices respectively for playing games or processing softwares or applications, which comprises the steps of:
(a) providing a plurality of individual electronic devices with hand support devices, such as notebook, tablet, smart device, cellular phone, portable computer, image capturing device, voice capturing device, motion sensing device, augmented reality (AR) device, and/or virtual reality (VR) device, installed with a sideline program for operating multi-task interaction for a plurality of players respectively for playing games via each of the individual electronic devices; and
(b) remotely linking the individual electronic devices to a networking system, wherein the networking system comprises a communication network having a remote connecting module to electrically connect the individual electronic devices with a hand support devices and with the networking system in a remotely connection manner, and a central control device for managing the networking system.

In accordance with another aspect of the invention, the present invention provides an electronic device equipped with a hand support device for playing games or processing softwares or applications, comprising:
a processor that executes at least a first task application and a second related task application with different interactive programs at the same time;
a screen module operatively linked to the processor, wherein the screen module comprises a display screen having two or more display areas for displaying the first application and the second related application thereon respectively; and
one or more input modules operatively linked to the processor, wherein the first application and the second related application are simultaneously controlled by the input modules respectively, such that the first application and the second related application are executed to be displayed on the display areas respectively and are independently controlled by the input modules at the same time for enabling a user to play a game of the first application via one of the input modules and operate the second related application at the same time via the another input module without interfering the first application.

In one embodiment, the electronic device equipped with the hand support device further comprises a control module operating a sideline program to generate one or more sidelines displayed on the display screen to split the display screen into the two or more display areas.

In one embodiment, a sidelines program is generated as one of a horizontal sideline and a vertical sideline being movable on the display screen to split the display screen into the one or more display areas and to adjust a size of each of the display areas.

In one embodiment, the electronic device of the present invention further provides a control module which comprises a color code generator that generates different color codes for the one or more sidelines to indicate the different interactive programs of the game related application. It is also important to note that each of the sidelines is able to be controlled by voice command and audible. It is important to mention the electrical device with the hand support device is not dependent on the sideline program.

In one embodiment, a control panel of the electronic device equipped with the hand support device of the present invention is coupled at the display screen, wherein the input modules are provided at the control panel to independently control the first application and the second related application displayed on the display areas of the display screen.

In one embodiment, at least a visual sideline is slidably formed and displaced at the display screen of the electronic device equipped with the hand support device of the present invention to separate the first application and the second related application displayed on the display areas respectively and at least another control sideline is slidably formed and displayed at the control panel to separate the input modules thereon.

In one embodiment, at least one of the input modules is automatically selected to match with the first application and at least one of the input modules is manually selected by the user to match with the second related application.

In one embodiment, the electronic device equipped with the hand support device of the present invention further includes a phone connection station for connecting with a user smart phone of the user, wherein the verification module comprises a verification program application to generate a verification code in order to activate the electronic device with a hand support devices and also to executed the user smart phone settings and preferences down to the electronic device automatically.

In one or more embodiments, the electronic device equipped with the hand support devices of the present invention supported by the sideline program to provide the sideline(s) at the display screen and/or the control panel is embodied as an innovative portable electronic device with a hand support device, a traditional notebook, tablet or smart device, an AR device, a VR device, or AR/VR device.

In one embodiment, the communication network used by the electronic device equipped with the hand support device of the present invention is a closed communication network module being executed by the processor for wirelessly linking to a private networking system, wherein the first application is restricted for being accessed only through the private networking system.

In one embodiment, the electronic device equipped with the hand support device of the present invention further includes a positioning unit for detecting a location of the electronic device, such as notebook, smart device, tablet, portable computer, AR device, VR device, or AR/VR device, wherein the electronic device may or may not be disable for being outside a facility perimeter area in a real time manner via the positioning unit.

In one embodiment, the electronic device equipped with the hand support device of the present invention further includes a chatting module, wherein the second related application comprises a chatting application being executed for enabling the user to chat with another user of another portable electronic device with a hand support devices via the chatting module when the users play or process the same first application.

These and other objectives, features, and advantages of the present invention will become apparent from the following detailed description, the accompanying drawings, and the appended claims.

BRIEF DESCRIPTION OF THE DRAWINGS

FIGS. 39A to 39C illustrate the electronic device interacting with the AR/VR device according to the above preferred embodiment of the present invention.

DETAILED DESCRIPTION OF THE PREFERRED EMBODIMENT

Figure 1:
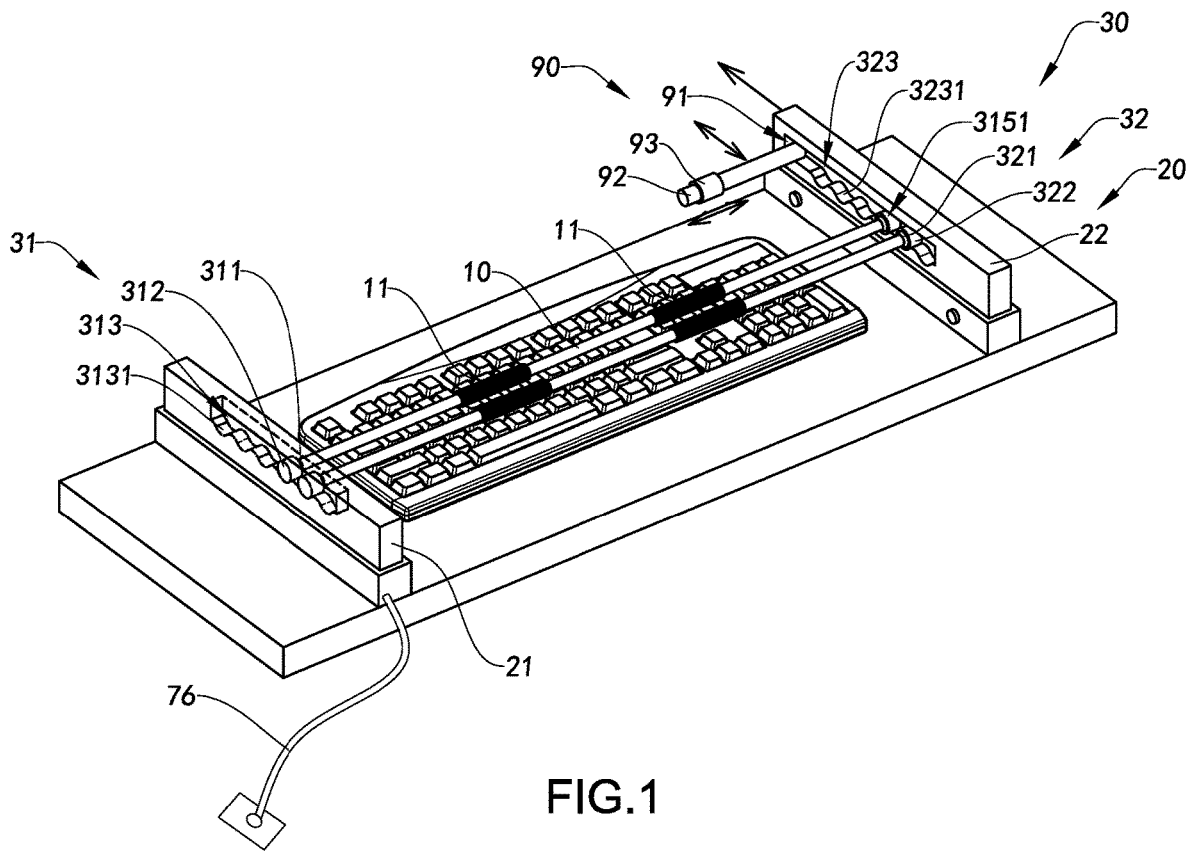
FIG. 1 is a perspective view of a hand support device according to a first preferred embodiment of the present invention.
Figure 2:
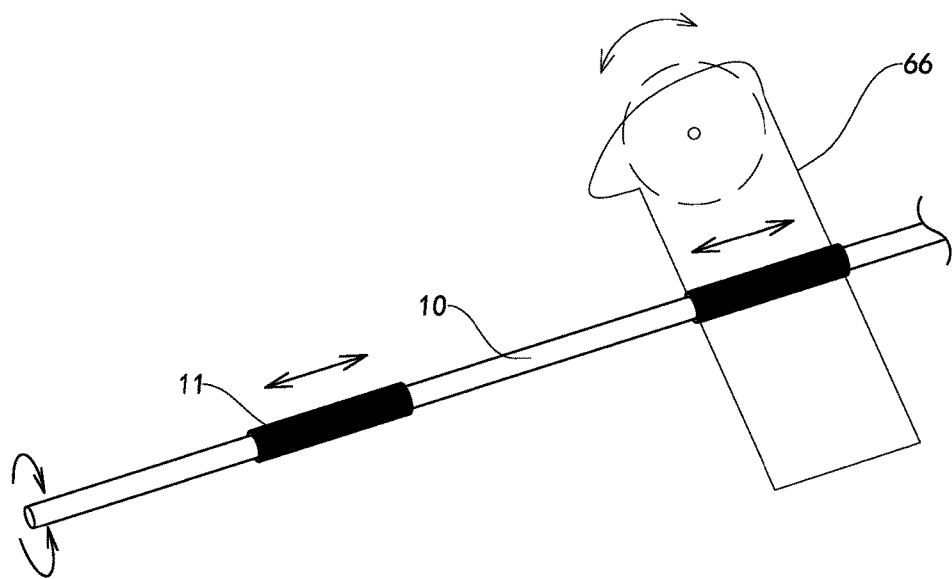
FIG. 2 is a partial perspective view of the above first preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIG. 1 to FIG. 7 of the drawings, a hand support device for input apparatus such as typing apparatus like keyboard, notebook, laptop, or the like according to a preferred embodiment of the present invention is illustrated, wherein the hand support device can be mounted with a keyboard to provide assistance with work like typing and repetitive fingers or wrist movements, and other activities of hands or wrists such as playing games and recreational repetitive activities, while providing various therapeutic and medicinal treatments.

The hand support device according to the preferred embodiment of the present invention comprises an elongated hand supporting bridge unit 1 and a support base assembly 20. The hand supporting bridge unit 1 comprises one or more elongated bars 10 and the support base assembly 20 supports the bars 10 of the hand supporting unit 1 directly over the keyboard along the keyboard from the right side to the left side of the keyboard so that the user can rest on and work.

At the same time the bars 10 sit over the keyboard, the user can control the desire direction for comfort thereof. In other words, the bars 10 provide an upward and downward motion support, a left to right distance support, and oblique angles left to right horizontal plane reaching support and a bilateral vertical angular finger distant positioning support. Preferably, the bars 10 sits over the keyboard where the height is adjustable for the different users to work and rest. Additionally, the bar or bars 10 can be under or on the side of the input apparatus such as typing apparatus like keyboard to support a brace 66 visa versa as another example. It is important to mention the bar or bars 10 can be of any shape like hollow bars, I beam, L beam, C channel, U channel, formatted truss etc.

In other words, the user will type with the controlled support of the bars 10, which will enable the user to sit in a correct posture and avoid his cervical vertebra are in a wrong state of forward flexion. In other words, the user needs less efforts in maintain the correct sitting and typing posture for longer periods of time with the keyboard hand therapeutic support device.

Preferably, the bars 10 have different diameter and length with various functions and can be sold separately to meet the user, necessities and to meets most size of the keyboard in the market. The bars 10 can be made of fiber organic composites, glass, wood, plastic, ceramic composites, rubber, carbon, metallic alloys, or any of these combinations together as a hold or in sections throughout the bars 10. The bars 10 can have various designated shapes with various designated contours, such as being circular, triangular, rectangular or star configuration. The number of the bars 10 shown in the figures is an example not limited, where the hand support device is preferred to comprise a pair of bars 10 adapted for the wrists of the user's hands resting between the pair of bars 10 while typing or using the keyboard or the like.

The bars 10 of the hand supporting bridge unit 1 can be positioned together working as one unit or separately apart to provide the desire position for comfort in relation to the upper extremities. And the bars 10 can be elevated or declined in relation each of the other adjacent bars for additional comfort. Preferably, the separation between the bars 10 can be up to 8 inches. The bars 10 can also radiate heat or cold to the fingers, hands and wrists of the user. In addition, vibrating frequency, Transcutaneous Electrical Nerve Stimulation (TENS), Percutaneous Electrical Nerve Stimulator (PENS), Microcurrent Electrical Therapy (MET), and Cranial Electrotherapy Stimulation (CES, topical medication, transdermal/transcutaneous therapy can be provided while working or playing. The treatment and efficacy can also be monitor and recorded through the hand support device via intranet or internet. The bars 10 can be solid, hollow, fabricated with single or multiple materials for multiple conductions, and as a structural facilitator, for the present invention for and future treatments options, recreational and or medicinal.

The support base assembly 20 comprises a first base unit 21 and a second base unit 22 which arranged respectively on the left and the right sides of the keyboard to support the motion of the hand supporting bridge unit 1. A first end and a second end of each of the bars 10 of the hand supporting bridge unit 1 are arranged at the first base unit 21 and the second base unit 22 respectively so as to extend along the length of the keyboard and perpendicular to the left and right margins of the keyboard. According to the preferred embodiment of the present invention, the hand supporting bridge unit 1 comprises a pair of elongated bars 10 arranged in parallel and to be moving up and down across the keyboard between the first base unit 21 and the second base unit 22 of the support base assembly 20.

Figure 3:
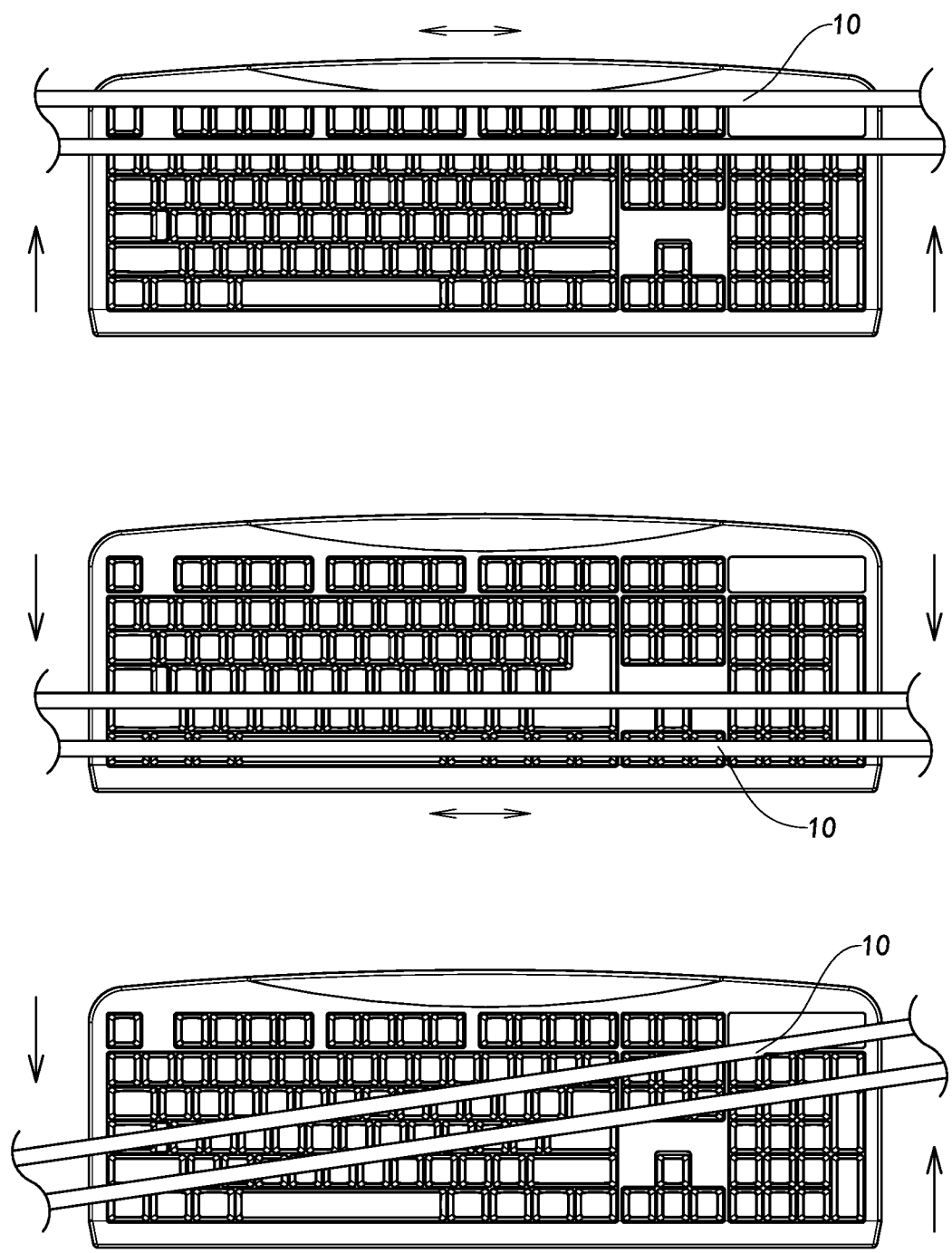
FIG. 3 is a schematic view of the above first preferred embodiment of the present invention.

The first base unit 21 and the second base unit 22 provide the vertical and structural support the bars 10 adapted for the function of effortless reaching to minimize energy consumption and maximize productivity through the support on the upper extremities, such as plantar surface, volar medial, lateral ulnar and metacarpal region of both wrist, flexor retinaculum or distal ulnar or radius anterior or lateral region of the hands. All of these are accomplished while the hands and the wrists are at the most neutral relaxing position for the user to hover over the input apparatus such as typing apparatus like keyboard. Accordingly, the user may use the input apparatus, such as typing, with a wrist support typing posture, as shown in FIGS. 3 and 30, that the wrists of the user are well supported by the bars 10 of the hand supporting bridge unit 1 enabling his or her hands naturally hanging down from the wrists to reach the typing apparatus, so that the user may move his or her fingers freely and naturally without stresses applied on his or her wrists.

The first base unit 21 and the second base unit 22 can be made of fiber organic composites, glass, wood, plastic, ceramic composites, rubber, carbon, metallic ally, or any of these combinations together as a hold or in sections throughout the first base unit 21 and the second base unit 22. Preferably the first or second base unit 21 or 22 is equal or higher than an input apparatus such as typing apparatus like keyboard.

Further, the hand support device comprises a pillar and bar joint assembly 30, which is arranged to movably insert the bars 10 into the first base unit 21 and a second base unit 22 in order for the bars 10 to provide a transversal support for the user's upper extremities over the input apparatus such as keyboard. The pillar and bar joint assembly 30 comprises a first pillar and bar joint 31 and a second pillar and bar joint 32 respectively arranged at the first base unit 21 and the second base unit 22, wherein the bars 10 is supported between the first pillar and bar joint 31 and the second pillar and bar joint 32 which are positioned respectably on opposite side of the keyboard.

Referring to FIGS. 1 to 7, a ball-and-socket joint is implemented according to the preferred embodiment, which comprises a pair of first bearing members 311, a pair of second bearing members 321, a pair of first bearing sockets 312, and a pair of second bearing sockets 322. The first bearing members 311 are respectively arranged at first ends of the bars 10 and the second bearing members 321 are respectively arranged at second ends of the bars 10, wherein the bars 10 of the hand supporting bridge unit 1 are extended between the first bearing members 311 and the second bearing members 321. A first bearing socket 312 corresponding to the first bearing members 311 is mounted at a first guiding slot 313 defined in the first base unit 21 in a movable manner, wherein the first bearing members 311 are mounted actively in the first bearing socket 312. One skilled in the art will understand the operating principle and basic structure of the ball-and-socket joint which is not repeated here.

Figure 4:
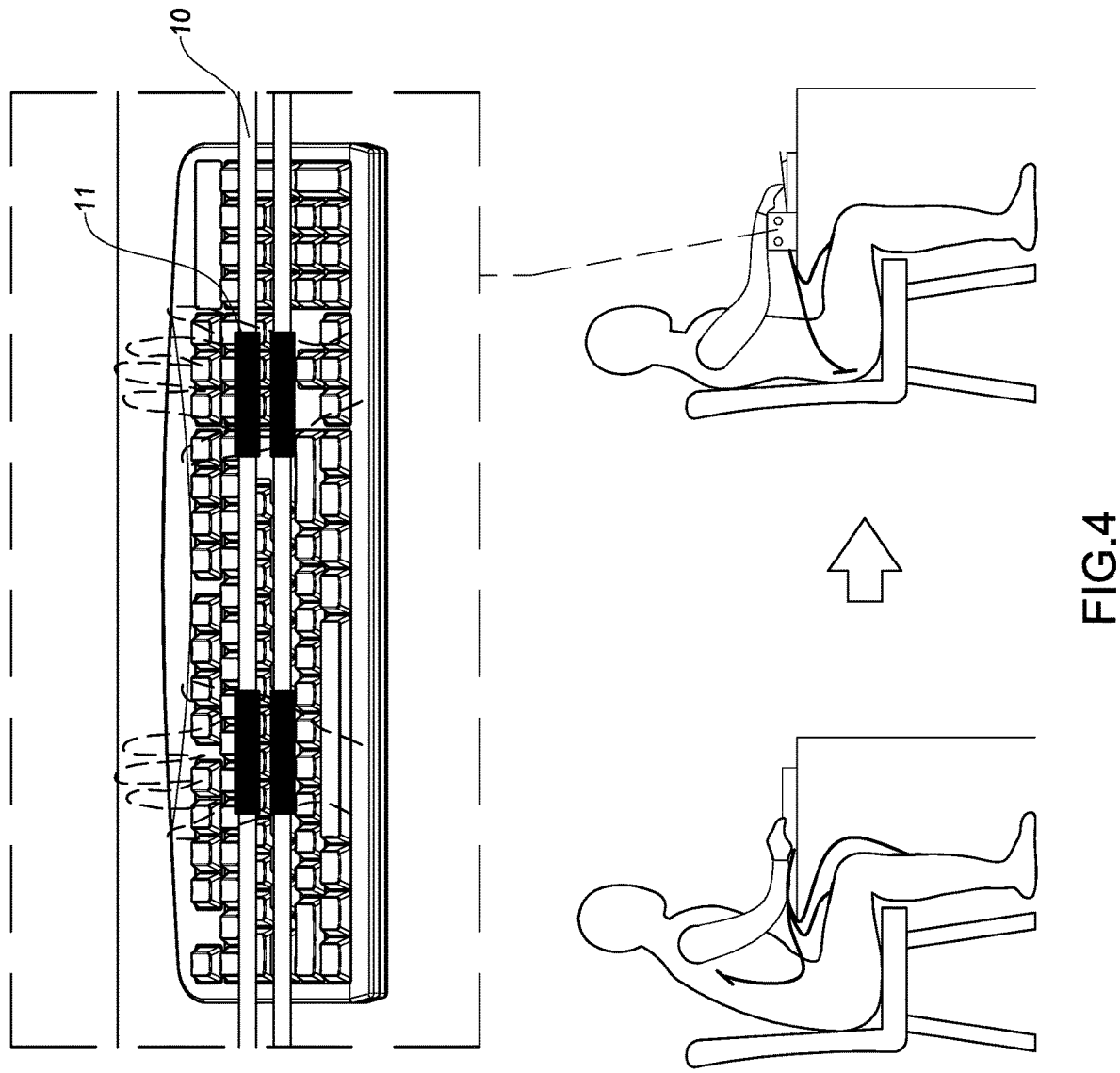
FIG. 4 is an application view of the above first preferred embodiment of the present invention.

By means of the ball-and-socket joint, each first end of the bars 10 can be rotated to move forward, backward, upward and downward freely and independently. Likely, the second bearing socket 322 corresponding to the second bearing members 321 is mounted at a second guiding slot 323 defined in the second base unit 22 in a movable manner, wherein the second bearing member 321 is mounted actively in the second bearing socket 322, wherein each second end of the bars 10 can be rotated to move forward, backward, upward and downward freely and independently. Accordingly, the wrists of the user resting and being supported on the bars 10 of the hand support bridging unit 1 in the wrist support typing posture are able to move up-and-down and left-and-right above the typing apparatus, as shown in FIGS. 4 and 30, so that the user has no need to bend his or her wrist left and right and to stretch or bend his or her fingers to reach different keys on the keyboard that is the main cause of the joint injury to the wrists and fingers of those users who need to type for relative long time continuously. Instead, the user may naturally hang down his hands and fingers from his or her wrists which are well supported by the hand support bridging unit 1 during typing naturally and neutrally while moving the whole hands vertically and horizontally above the typing apparatus by means of the hand support device of the present invention.

The first guiding slot 313 is formed in an inner side of the first base unit 21, wherein the first bearing socket 312 is mounted in the first guiding slot 313 in a movable manner. The first guiding slot 313 has a first gear rail 3131 arranged at a bottom of the first guiding slot 311, wherein the first bearing socket 312 has a first periphery matched to the first gear rail 3131. In other words, the size of the first bearing socket 312 matches each slot of the first rail 3141 to allow the first bearing socket 312 with the first end of bars rotating e forward and backward and locking at the desire position.

Likely, the second guiding slot 323 is formed in an inner side of the second base unit 22, wherein the second bearing socket 322 is mounted in the second guiding slot 323 in a movable manner. The second guiding slot 323 has a second gear rail 3231 arranged at a bottom of the second guiding slot 312, wherein the second bearing socket 322 has a second periphery 3151 coupled to each slot of the second gear rail 3231. The second bearing socket 322 and the second gear rail 3231 couple to allow the second bearing socket 322 with the second end of bars rotating forward and backward and locking at the desire position, so the desire bar separation between two neighboring bars 10 can be fixed. Or, the first periphery and the second periphery 3151 are arranged with gears around meshed with the first gear rail 3131 to achieve the objects above.

Due to the first bearing socket 312 and the second bearing socket 322 freely moving and not limiting the ball bearing moving, any end of the bars 10 can move in desire direction. Especially, the first end of the bars can move distally away from the user while the second end of the same bars can be moving proximally closer to the user and vice versa, so the user can move his hand for typing freely.

The support base assembly 20 and the pillar and bar joint assembly 30 provide the rolling motion of the bars 10 in a clockwise motion and counterclockwise motion while providing the surface area for the hands and/or wrists to rest thereon. The pillar and bar joint assembly 30 also supports and provides the housing length to the bars 10 for the horizontal angular plane displacement of the bars 10.

Figure 5:
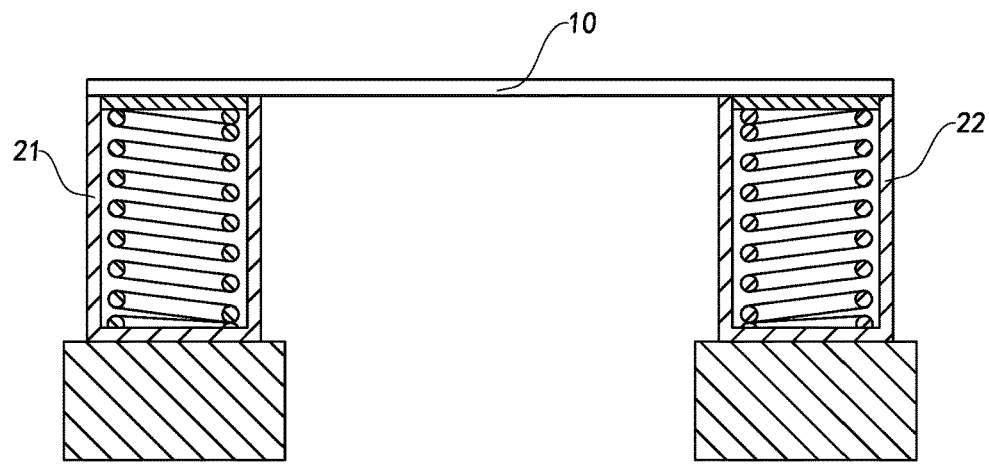
FIG. 5 is a side view of the above first preferred embodiment of the present invention.
Figure 6:
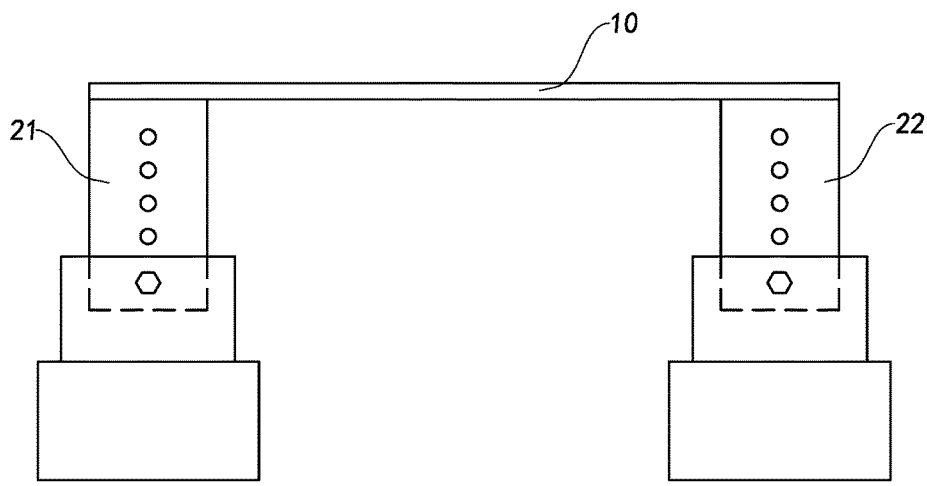
FIG. 6 is a side view of the above first preferred embodiment of the present invention.
Figure 7:
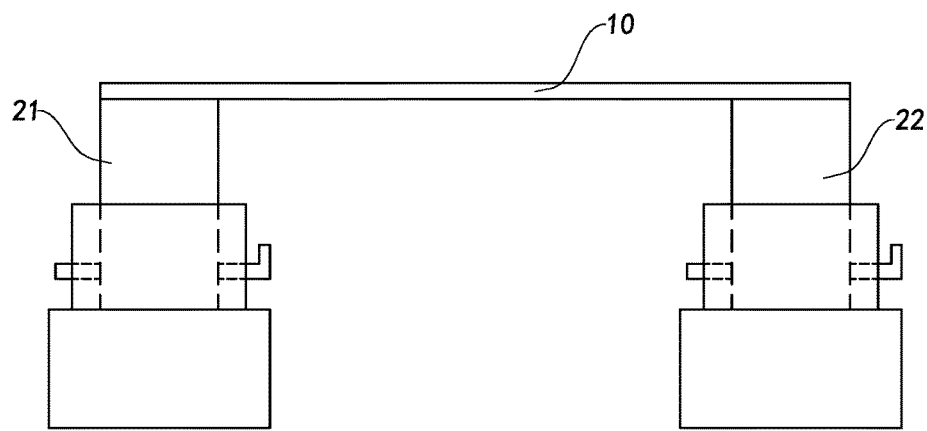
FIG. 7 is a side view of the above first preferred embodiment of the present invention.
Figure 8:
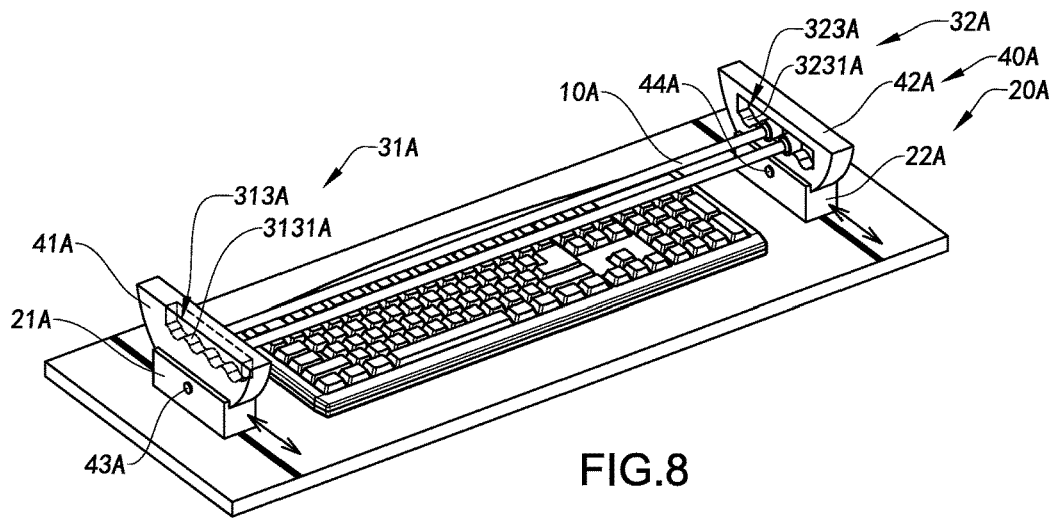
FIG. 8 is a perspective view of a hand support device according to a second embodiment of the present invention.
Figure 9:
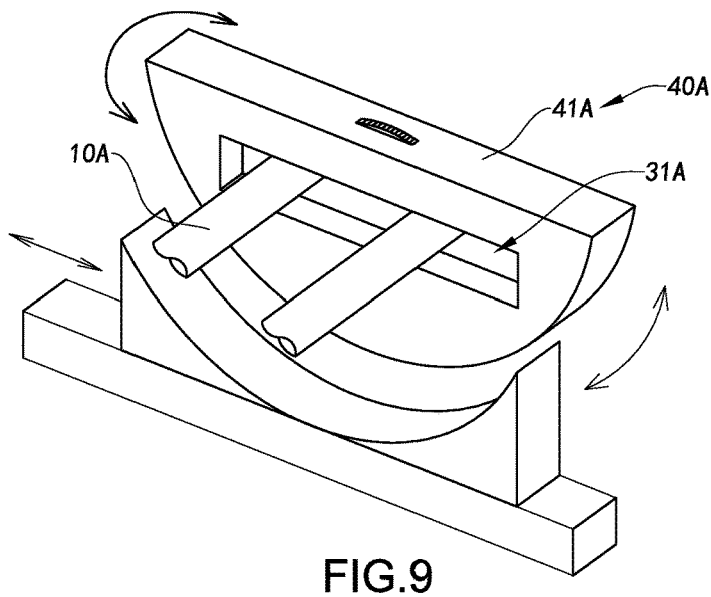
FIG. 9 is a partial perspective view of the above second embodiment of the present invention.
Figure 10:
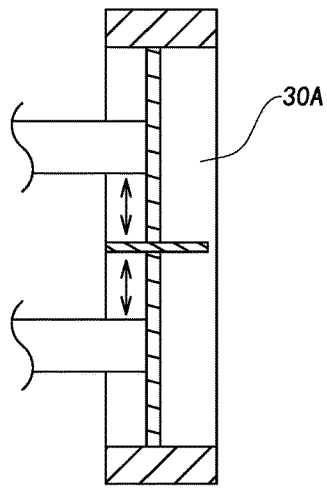
FIG. 10 is a section schematic view of the above second embodiment of the present invention.
Figure 11:
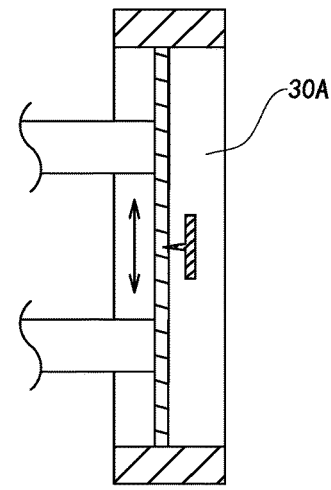
FIG. 11 is a section schematic view of the above second embodiment of the present invention.

In addition, the first base unit 21 and the second base unit 22 are arranged to be adjustable in height, referring to FIG. 5 to FIG. 7, so as to provide an adjustable vertical support structure while maintaining a vertical parallel height between the bars 10 of the hand supporting bridge unit 1 and the keyboard to the user's desire fix height position and at the same time to maintain the desire fix separation between the bars 10 in relation to the upper extremities. The first base unit 21 and the second base unit 22 are adjustable to height size by clamp, push pin, spring torque, screw positional adjustment, track trial, hydraulic pressure, spring tension or air compression in combination or independent. Or the first base unit 21 and a second base unit 22 can be collapsible, when not in used and the entire device is portable.

In the preferred embodiment, the first base unit 21 and the second base unit 22 are implemented as a telescopic structure as shown in FIGS. 5 to 7. An inner pillar is mounted to slide in an outer pillar, wherein a screw is mounted near the top edge of the outer pillar to control and lock the slide of the inner pillar. When the screw is tightened, the inner pillar is locked at the desire position and when the screw is loosed, the user can slide the inner pillar to the desire position. One skilled in the art will understand that the structure in the preferred embodiment is an example, they can use other structure to control and lock the height of the first base unit 21 and the second base unit 22 mentioned above.

Moreover, as shown on FIG. 4, the hand supporting bridge unit 1 further comprises a plurality of sleeves 11 provided around the bars 10 for additional motion in relation to the existing motion of the bars 10. For example, if the bars 10 are in a rolling motion clockwise or counterclockwise, the sleeves 11 increase additional rolling motion clockwise and counterclockwise in relation to the existing clockwise motion or counterclockwise motion of the bars 10. The motion of the sleeves 11 is like the motion of the bars 10 of the hand supporting bridge unit 1 which can be locked in either motion or completely fix to no motion either way, such as forward and backward rotation.

In addition, the bars 10, sleeves 11, and the braces 66 are the end points where therapeutic build-in leads carry the specific therapeutic currents from the hand support device to the user's skin to provide therapy. In others words, the hand support device also has multiple non built-in leads that attach to an electro path independently for the built-in leads of the bars 10, sleeves 11 and braces 66, and therefore to deliver additional desire therapy on any other body part where the user requires treatment. For example, while the user is treating his or her upper extremity through the bar, sleeve, or brace, the user can connect the non built-in leads on the hand support device and also place corresponding electros pad on the other end of the non-built-in leads. Ultimately, the user may position the electro pads on the skin surface of the back and legs and therefore get a more complete body care, for example an external bone stimulator.

Further, the sleeves 11, bars 10, and braces 66 can be spring loaded to achieve desire placement at all times of the sleeve, brace and bars in combination or separated in relation to making contact with the user's skin. This will also give the user proprioception in relation to the home run keys on the input apparatus such as typing apparatus like keyboard and on the overall hand support device location.

The additional function of the sleeves 11 and brace 66 are to decrease contact dermatitis and provide shock support. The sleeves 11 and braces 66 can have various shapes and sizes. The sleeves 11 and braces 66 can be made of fiber organic composites, glass, wood, plastic, ceramic composites, rubber, carbon, metallic alloy, or any of these combinations together as a hold or in sections throughout the sleeves 11 or brace 66. The sleeves 11 is mounted on the parallel bars 10 in a sliding manner, wherein the sleeves 11 provide the user additional left to right sliding motion on the bars in relation to the keyboard and vice versa. The brace 66 can be mounted on the sleeve or without the sleeve on to the bars providing the same sliding function as the sleeve 11, as mention above, with additional treatments options and comfort. For example, the brace 66 can transfer current or heat on to a glove, body sleeve, split or a garment as other means of delivering therapy and where the bars and sleeves can have the same function of the brace, as mention above.

The support base assembly 20 further comprises a mouse device 90. The mouse device 90 is configured in the inner side of the second base unit 22. The mouse devices 90 is installed in front of the bars 10, as shown on figured 1. Preferably, the mouse device 90 perpendicular in front of hands in relation to the bars for convenience and effortless repetitive motions. The mouse device 90 further comprises a detecting bar 92 and a detecting sleeve 93. The detecting sleeve 93 is provided around the detecting bar 92. The second base unit 22 further has a slot 91. One end of the detecting bar 92 is installed in the slot 93 so as to the detecting bar 92 is able to move along the slot 91. When the detecting bar 92 moving along the slot 91, the detecting bar 92 detects the displacement between the original place of the slot 91 to the current place of slot 92, and sends a moving data regarding to the displacement to a computer. The computer processes the moving data and control the mouse to move. When the detecting sleeve 93 moving along the detecting bar 92, the detecting sleeve 93 detects the displacement between the original place of the detecting bar 92 and the current place of the detecting bar 92, and then sends the moving data regarding the displacement of the detecting sleeve 93 to the computer. The computer processes the moving data and control the mouse to move. It is important to mention the mouse devices moves with the pillar assembly 20, so that the user is capable of having minimal finger reach to active the mouse devices 90 at all time with minimal reaching effort. The mouse devices 90 is capable of being installed in the first base unit 21 and/or the second base unit 22. Preferably, the mouse device 90 is attached and installed on the second base unit 22 if user is right hand dominant per drawing schematic. In another embodiment, the mouse device 90 is a trackball. The track ball has at least one LED (light emitting diode). The mouse device 90 can be a touch flat pad or touch screen. The touch flat pad and the touch screen have various designated shapes, such as rectangle, triangle, square, circle, cylinder, tube, or sphere. The user is able to control to mouse through the touch flat pad or touch screen, such as, single tap, double tap and other operation. The mouse device 90 can be a nipple mouse. The nipple mouse has the same functions as the computer mouse. It is also important to mention that motion hologram technology can also be applied to the keyboard and mouse controls.

Referring to FIGS. 8 to FIG. 11, the hand support device according to a second preferred embodiment of the present invention is illustrated. The hand support device further comprises a pillar joint assembly 40A which is rotatably mounted at the support base assembly 20A for the angular motion of the bars.

The pillar joint assembly 40A comprises a first swing pillar 41A and a second swing pillar 42A, which are respectively mounted rotatably at the first base unit 21A and the second base unit 22A on both sides of the keyboard respectively. The pillar and bar joint assembly 30A is formed at the pillar joint assembly 40A, wherein the first pillar and bar joint 31A is arranged at the first swing pillar 41A and the second pillar and bar joint 32A is arranged at the second swing pillar 42A.

The first guiding slot 313A with the first gear rail 3131A is defined at the first swing pillar 41A and the second guiding slot 323A with the second gear rail 3231A is defined at the second swing pillar 42A, wherein the first periphery of the first bearing socket 312A couples with the first gear rail 3131A and the second periphery of the second bearing socket couples with the second gear rail 3231A, so the ends of the bars 10A of the hand supporting bridge unit 1A mounted with balls can move relative to the first swing pillar 41A and the second swing pillar 42A.

The pillar joint assembly 40A further comprises a first rotation and fix component 43A and a second rotation and fix component 44A, wherein the first swing pillar 41A is mounted at the first base unit 21A in a swing manner by the first rotation and fix component 43A and the second swing pillar 42A is mounted at the second base unit 22A in a swing manner by the second rotation and fix component 44A. When the first swing pillar 41A and the second swing pillar 42A rotate at the desire position, a surface of the bars 10A defined has a desire angle with the keyboard which increases additional comfort for the hand and wrist. When the first swing pillar 41A and the second swing pillar 42A rotate at the desire position, the first rotation and fix component 43A and the second rotation and fix component 44A lock the rotation.

Figure 12:
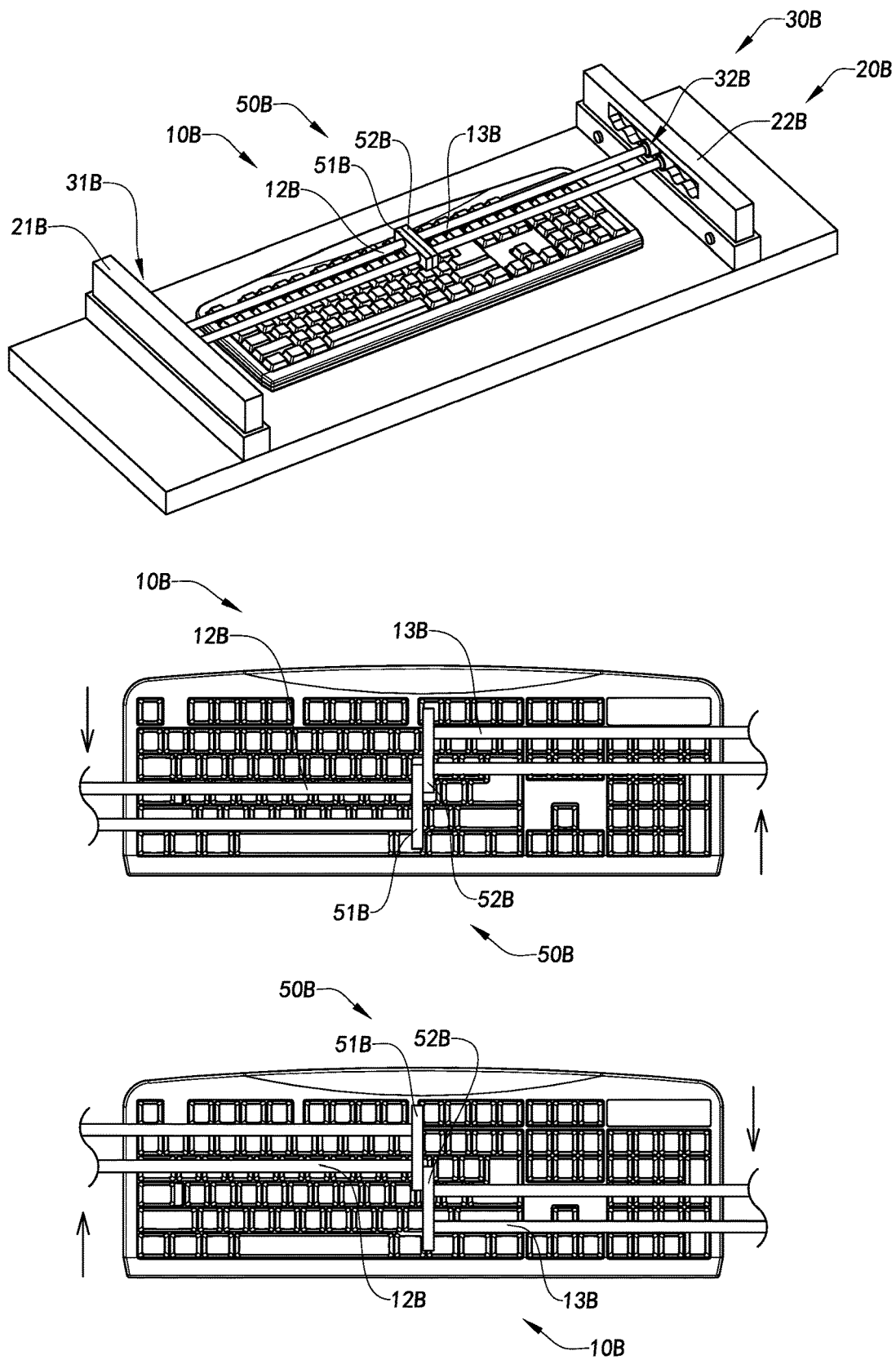
FIG. 12 illustrates a perspective view and schematic views of a hand support device according to a third embodiment of the present invention.

Referring to FIG. 12, the hand support device according to a third preferred embodiment of the present invention is illustrated. Each of the bars 10B of the hand supporting bridge unit 1B is divided into two half bars, including a first half bar 12B and a second half bar 13B, wherein a mid-bar divider 50B is arranged in the middle of the first half bar 12B and the second half bar 13B arranged in a same extension line.

The mid-bar divider 50B comprises a first mid-bar divider 51B and a second mid-bar divider 52B, wherein the first mid-bar divider 51B and the second mid-bar divider 52B are arranged to slide on each other to permit the first mid-bar divider 51B and the second mid-bar divider 52B to move forward and backward independently. According to the same embodiments, the first mid-bar divider 51B has a sliding slot which couples with a raised sliding joint of the second mid-bar divider 52B, wherein the raised sliding joint is inserted in the sliding slot so that the first mid-bar divider 51B and the second mid-bar divider 52B can slide independently.

One end of the first half bar 12B is arranged at the first base unit 21B and the other end of the first half bar 12B is inserted to one side of the first mid-bar divider 51B opposite to the sliding slot, while one end of the second half bar 13B is arranged at the second base unit 22B and the other end of the second half bar 13B is inserted to the other side of the second mid-bar divider 52B opposite to the raised sliding joint. In order to adjust and fix the separation of the half bars, a guiding slot with a gear rail can be arranged in the side of the first mid-bar divider 51B or the second mid-bar divider 52B the half bar inserted.

The mid-bar divider 50B can also permit the half bars 12B, 13B of the bars 10B to move upward and downward by a frictionless surface that will be telescope perpendicular or a sliding connective symbiotic pressure cancelation, which will continue to provide support on the bars 10B. And be able to resist gravity and support the apply forces by both user hands on opposite sides of the mid-bar divider 50B. In other words, the movement of moving the hand up and down independent from each other can be also accomplished by the mid-bar divider 50B between the first half bar 12B and the second half bar 13B.

It is worth to mention that the mid-bar divider 50B is situated directly in the middle between the first half bar 12B and the second half bar 13B, wherein each of the first mid-bar divider 51B and the second mid-bar divider 52B have an opposite frictionless surface parallel to each other. Both the frictionless surfaces of the first mid-bar divider 51B and the second mid-bar divider 52B are parallel and have proportionally length to maintain contact throughout the frictionless surface telescoping connector at all times throughout the require up and down motions. Furthermore, both the frictionless surfaces stay in contact directly or indirectly to opposed and cancel the downward pressure apply by the hands on the bars 10B and to provide the independent up and down frictionless motion on the hands on the bars. Because of mid-bar divider 50B is arranged in the middle between the bars 10, so that it does not get in the way from the keyboard operation being conducted by the user.

Figure 13:
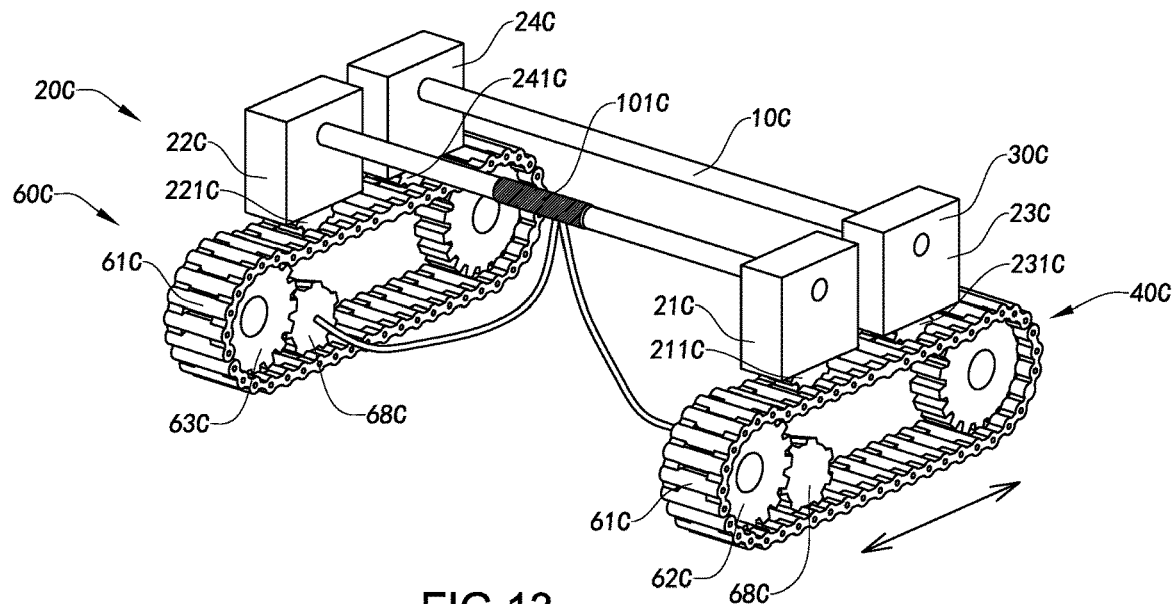
FIG. 13 is a partial perspective view of a hand support device according to a fourth embodiment of the present invention.

Each of the bars may be supported by a single pillar or a pillar may be arranged with multiple bars. Referring to FIG. 13, the hand support device according to a fourth preferred embodiment of the present invention is illustrated, wherein one pillar is only related to one bar. In other words, the support base assembly 20C further comprises a third pillar 23C arranged at the same side as the first base unit 21C to the keyboard, and a fourth pillar 24C arranged at the same side as the second base unit 22C to the keyboard, wherein one of the bars 10C is inserted and fixed into the first base unit 21C and the second base unit 22C, and another one of the of the bars 10C is inserted and fixed into the third pillar 23C and the fourth pillar 24C over the keyboard. One skilled in the art will understand that the number of the pillars and the bars is just an example not limited.

The hand support device further comprises a base assembly 60C which supports the pillar and bar joint assembly 30C to have the motion by being mounted on the base assembly 60C. The base assembly 60C provides a tandem motion between the support base assembly 20C on to the bars 10C over the keyboard, with or without the horizontal angular motion. Preferably, the base assembly 60C is a liner frictionless track base related to both sides of the keyboard.

According to the fourth preferred embodiment of the present invention, the base assembly 60C can be implemented as a band pulley system, a belt pulley system, a tooth pulley system, a Boston pulley system, or a timing belt system, wherein an upper track 61C is adjustable for each other separation of the bars 10C which locks the bars 10C of the hand supporting bridge unit 1C in the desire bar separation between the bars 10, and locks the location of the bars 10C in relation to the location of the first base unit 21C and the second base unit 22C to the keyboard.

The base assembly 60C comprises a first base 62C and a second base 63C, wherein the first base unit 21C and the third pillar 23C sit movably on the first base 62C, wherein the second base unit 22C and the fourth pillar 24C sit movably on the second base 63C. According to the fourth preferred embodiment, the first base 62C and the second base 63C are implemented as the band pulley system for example, wherein a first wheel 211C and a third wheel 231C mounted at the bottom of the first base unit 21C and the third pillar 23C mesh with the first base 62C for moving and freely and independently, wherein a second wheel 221C and a fourth wheel 241C mounted at the bottom of the second base unit 22C and the four pillar 24C mesh with the second base 62C for moving freely and independently, so the separation between bars 10C will be adjustable and locked according to the separation and the location of the formers. Along the track 61C, moving direction of the pillars is guided for the base assembly 60C to work as a unit.

In addition, the first base 62C and the second base 63C also support the upward and downward independent motion of the support base assembly 20C simultaneously, independent of the pillar and bar joint assembly 30C and the pillar joint assembly 40C. For example, a second lower chain pulley band is controlled by the user for an up and down gliding motion. It is in the mechanical layout that different gears types can be assembled for motorize electrical automatic sensory uses like spur gear, helical gear, herring gear, herring bone gear, rack and pinon gear, revel gear, spiral bevel gear, screw gear, worm and worm wheel gear, miter gear, and internal gear. Preferably, the band tension of the first base 62C and the second base 63C is adjustable to provide the user additional comfort.

Figure 14A:
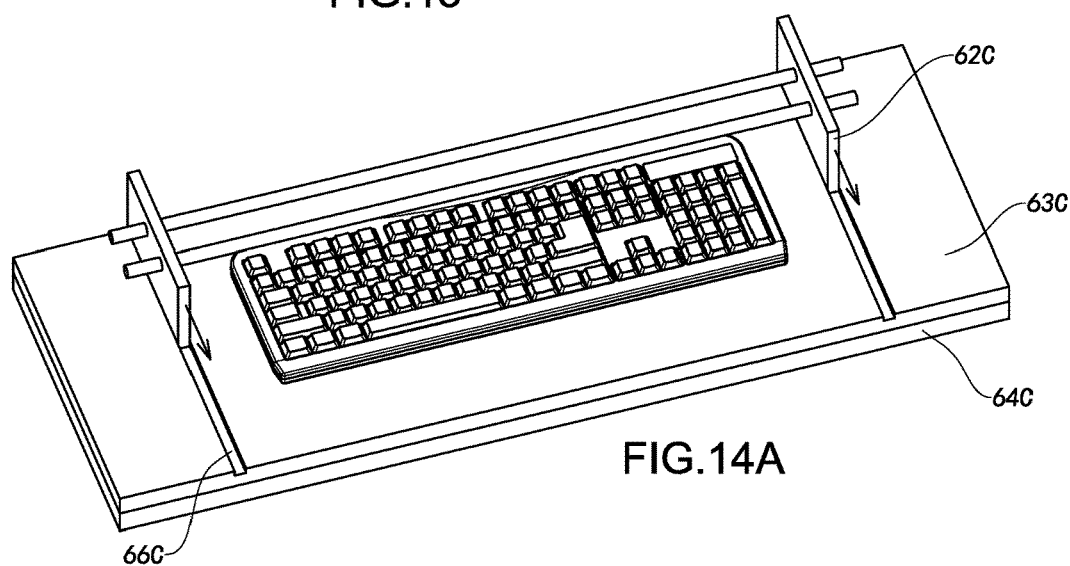
FIG. 14A is a section schematic view of the above fourth embodiment of the present invention.
Figure 14B:
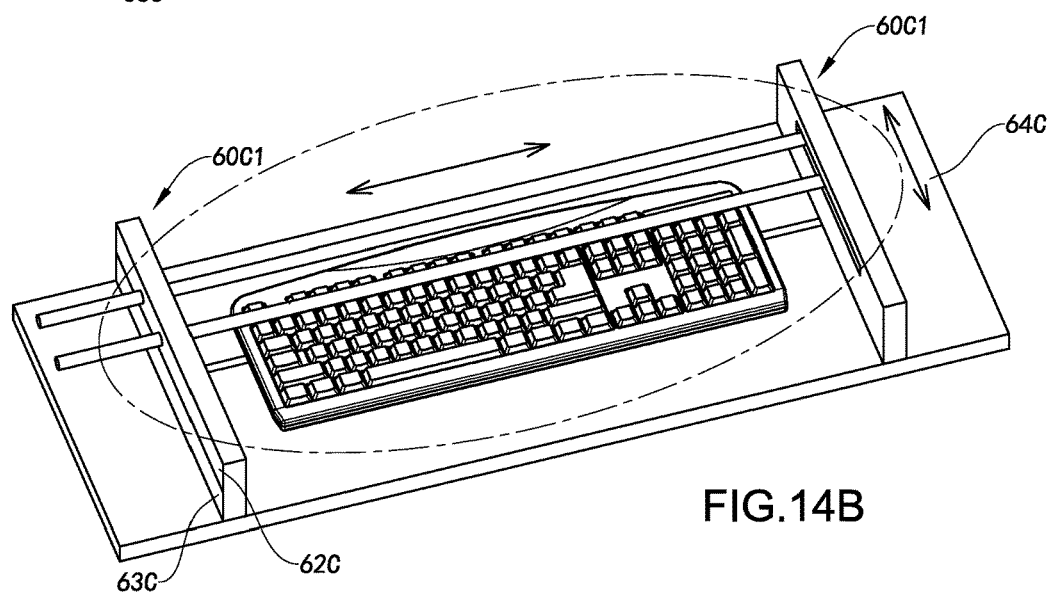
FIG. 14B is a section schematic view of the above fourth embodiment of the present invention.
Figure 15:
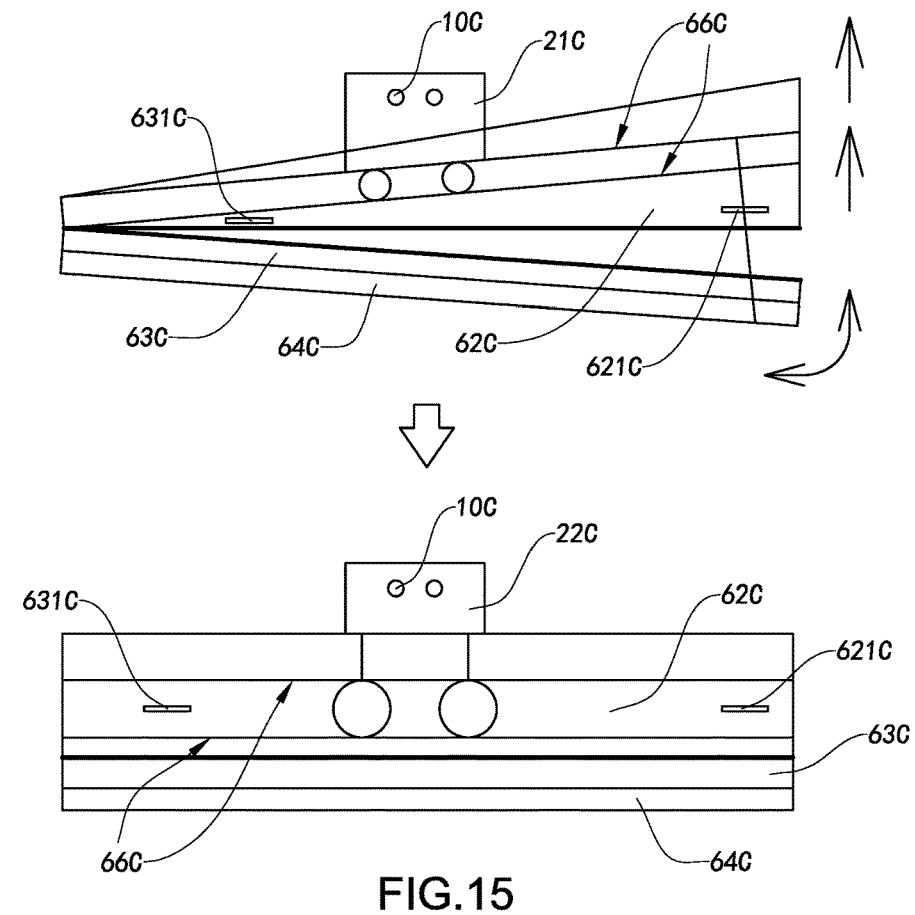
FIG. 15 is a section schematic view of the above fourth embodiment of the present invention.
Figure 16:
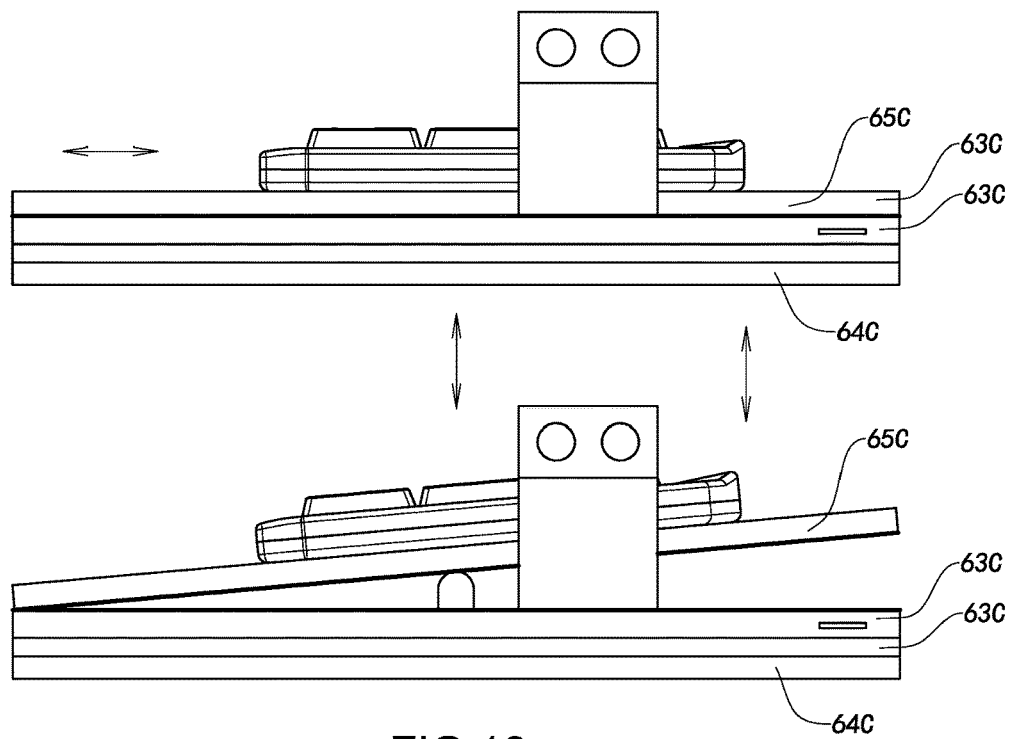
FIG. 16 is a section schematic view of the above fourth embodiment of the present invention.
Figure 17:
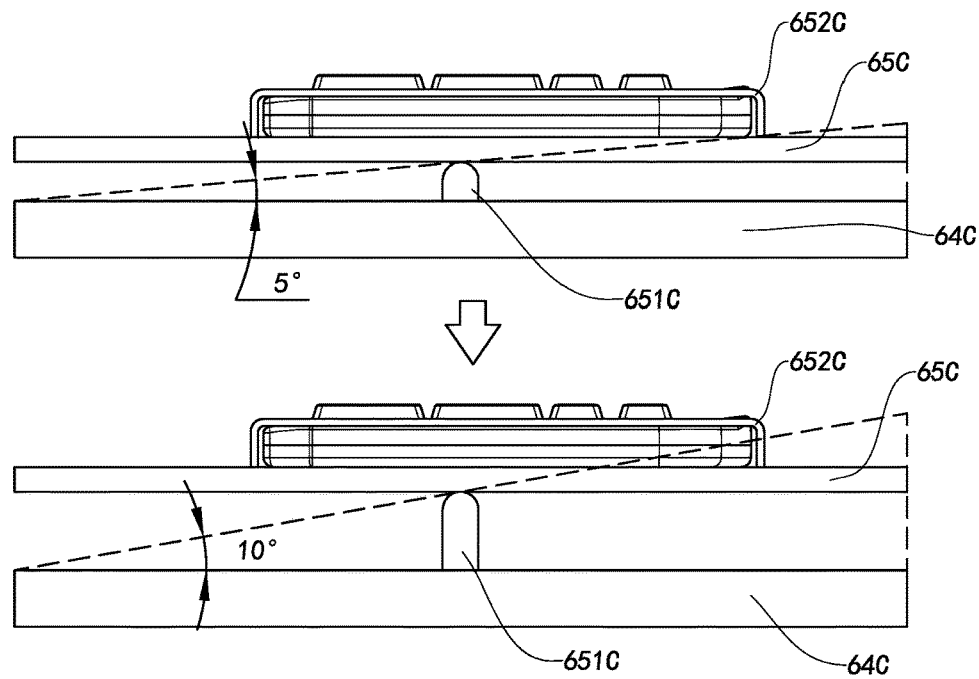
FIG. 17 is a section schematic view of the above fourth embodiment of the present invention.

Or, in another embodiment according to FIG. 14 and FIG. 15, the first base 62C comprises a first lift control 621C, while the second base 63C comprises a second lift control 631C to respectively support the first base 62C and the second base 63C to incline. By the first lift control 621C and the second lift control 631C, the distal ends of the first base 62C and the second base 63C related to the user may be higher than the proximal end to make the first base 62C and the second base 63C inclining and vice versa, wherein when the user can incline the first base 62C and the second base 63C in the opposite direction which forces the support base assembly 20C inclines away from the user in an automatic effortless manner.

Preferably, the first lift 621C and the second lift 631C provide at less a 0 to 60 degrees downgrading slope and upgradient slope. When the bars 10C of the hand supporting bridge unit 1C are over the keyboard and the users releases the bars 10C on an upper region of the keyboard, it will automatically have a gravitational down grade, wherein the support base assembly 20C with the bars 10C have a decline gradient at all times which leads the bars 10C closer to the user at a faster time automatically and effortlessly. In other words, the first lift control 621C and the second lift control 631C provide a faster and automatic gravitational direction of the support base assembly 20C and bars 10C related to the users and the operator upper extremities.

Figure 25:
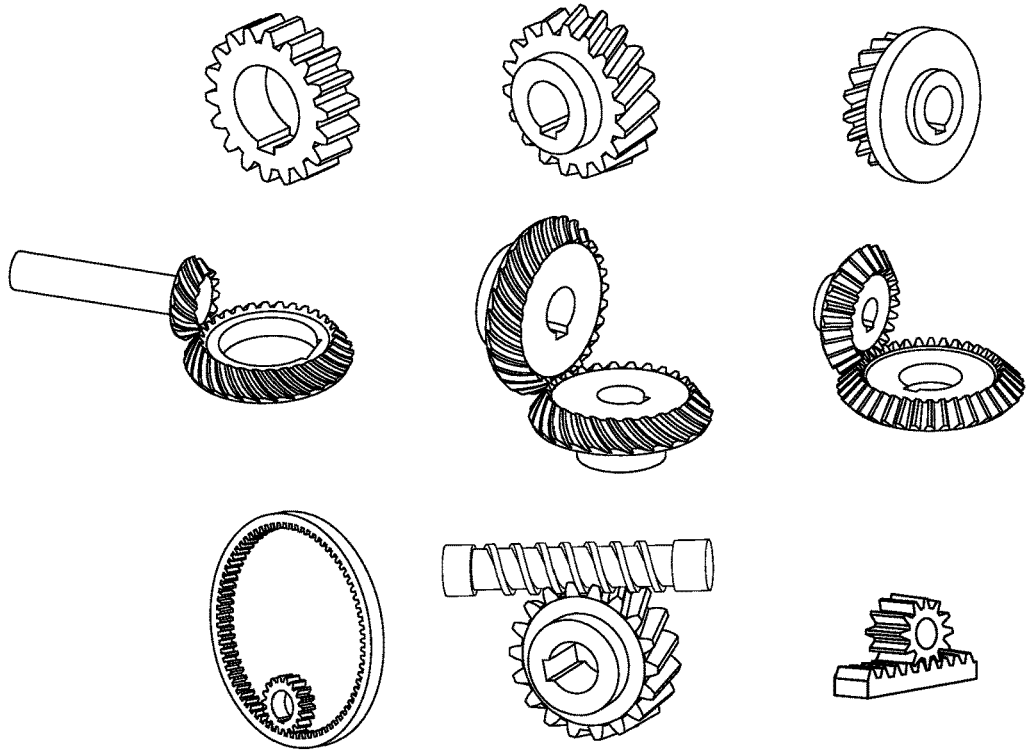
FIG. 25 illustrates schematic views of parts of the hand support device according to another embodiment of the present invention.

In other embodiments, an electronic device or a control device is arranged with the first base 62C and the second base 63C by any types of mechanical set ups, as shown in FIG. 25. As shown on FIG. 13, the base assembly 60C further comprises at least one pressure sensor 101C. The pressure sensor is provided on the bar 10. The base assembly 60C further comprises an electric motor 68C. The electric motor 68C is installed between the first base 62C and the second base 63C. The pressure sensor 101C is electric connected the electric motor 68C. When the pressure sensor 101C received pressure, the pressure sensor 101C sends a signal to the electric motor 68C for trigging the electric motor 68C to work. The electric motor 68C drivers the first base 62C and the second base 63C to move. According to the received pressure position of the pressure sensor 101C. The electric motor 68C is electrically connected a power source. By providing a pressure sensor, the hand support device will read and activated the control sensors to perform the desire actions electronically.

The base assembly 60C, as shown in FIG. 14, bears the weight of the support base assembly 20C, that provides a bilateral vertical support, a horizontal support cross sectional support and a lateral support. The base assembly 60C may or may not connect to the keyboard at the right and left opposite side of the keyboard. When the base assembly 60C connects the keyboard, it provides the keyboard stability in response to the forces being apply during normal usage. In another embodiment, as shown in FIG. 13, the electrical component and the motorize engine are inside the base assembly of 60C.

Preferably, the first base 62C and the second base 63C are made of fiber organic composites, glass, wood, plastic, ceramic composites, rubber, carbon, metallic ally, or any of these combinations together as a hold or in sections throughout the first base 62C and the second base 63C.

Further, a first incline slope control is arranged at the first base 62C and a second incline slope control is arranged at the second base 63C for additional direction guide at the first base 62C and the second base 63C. The first incline slope control and the second incline slope control can be a mechanical slide, a linear guide rail or track, a vertical wheel on a rail mount, dualvee motion technology guide wheel linear rack, wheel bearing and/or liquid nitrogen super conduction frictionless surface referring to FIG. 23.

In another embodiment, as shown on FIG. 15, one or more first guide rails 66C are supported by the first base 62C to predetermine the motions of the pillars sitting thereon that preset the motion rang of the bars 10C for the user, wherein the first guide rails 66C provide the pillars the movement and provide synchronization between the user, the keyboard and the hand support device. The guide rails can be made of fiber organic composites, glass, wood, plastic, ceramic composites, rubber, carbon, metallic alloys, or any of these combinations together as a hold or in sections throughout the guide rails. Likely, the first base 62C is supported by the second base 63C.

It is important to mention that the base units are arranged to house the mechanical movement mainly to prevent the user's clothing from getting stuck by or the user getting injured from all the moving parts. It is appreciated that the base units may also house other additional pressures components, electrical components and mechanical components for the delivery of the invention movements and functions. In addition, the each of the first and second base units can be mounted on the corresponding back brace for the movement where the base units are the barrier to prevent the movement of the hand support device from interfering with external objects. Furthermore, the base units can be mounted with additional bracing to provided additional support to taller individuals forearms and elbows from the sides of the base or from on top of the base unit on any and all embodiments of the present invention, including other embodiment that also includes a fix mount on a swivel.

As shown FIG. 14, the base assembly 60C further comprises a back brace 64C supporting the first base 62C and the second base 63C, wherein the back brace 64C connects the first base 62C and the second base 63C. The back brace 64C can be made of fiber organic composites, glass, wood, plastic, ceramic composites, rubber, carbon, metallic alloys, or any of these combinations together as a hold or in sections throughout the back brace 64C. The back brace 64 can be have various shapes and layouts to include different sizes.

The back brace 64C is an underneath plane surface area where all elements of the device and working parts in the device are housed and supported thereon. In other words, the back brace 64C is a surface tension area that makes direct contacts with a flush flat opposing a counter surface area where the hand support device sits on, such as a table. The back brace 64C is $1/16$ to 3 inches in thickness, 1 to 46 inches in length and 1 to 46 inches in width.

A mounted plate 65C attaches directly over the back brace 64C, wherein the mounted plated 65C is used to house the keyboard or laptop for stabilization, to the first base 62C and the second base 63C. The mounted plate 65C sits adjacent, side to side or slightly elevated in relation to the first incline slope control and the second incline slope control. The mounted plate 65C is arranged to rise and fall, wherein two elevators 651C are respectively arranged at the middle of the left edge and the right edge thereof next to the first base 62C and the second base 63C, which lock the mounted plate 65C at a neutral elevation. By elevating the two elevators 651C, the center of the left and right sides of the mount plate 65C, it provides an inclination and a declination independent from the first base 62C and the second base 63C which provide the inclination or declination for the pillars up or down grade movement independent from the position of the keyboard or laptop. the higher the keyboard or laptop is elevated with the mount plate 65C, the deeper the angle of inclination and vice versa the higher the angle for decline in relation to the bars 10C and pillars 21 and 22.

The mount plate 65C further comprises a block 652C to fix the keyboard, wherein the block 652C can be universal clips, screw, or straps in combination or through on process. It is important to mention that the elevators 651C work independent of the support base assembly 20C, the first base 62C and the second base 63C, wherein the mount plate 65C allows the keyboard to have a distal decline, distal elevation, or a neutral adjustment independently, when the keyboard or laptop are securely mounted on the mount plate 65C.

Preferably, the mounted plate 65C has the same length and width as the keyboard, wherein the mounted plate 65C has equal distance from the left side to the right side and from the top to the bottom of the base brace 64C. The base brace 64C connects the first base 62C and the second base 63C on the right and left side of the keyboard or laptop, to include the top and bottom sides of the keyboard or laptop in relation to the user. In another embodiment, the first base unit and the first base are integrally arranged and the second base unit and the second base are arranged integrally arranged as a base and pillar fix structure. The base and pillar fix structure may or may not connect to the back brace, or even be arranged without the back brace. The base and pillar fix structure can be made of fiber organic composites, glass, wood, plastic, ceramic composites, rubber, carbon, metallic alloys, or any of these combinations together as a hold or in sections throughout the base and pillar fix structure. The back brace may or may not connect the base and pillar fix structure on all sides the hand support device. In other words, the top is the horizontal most distal keyboard margin in relation to the user and the bottom of the keyboard is the proximal most closes to horizontal margin of the keyboard in relation to the user.

Figure 18:
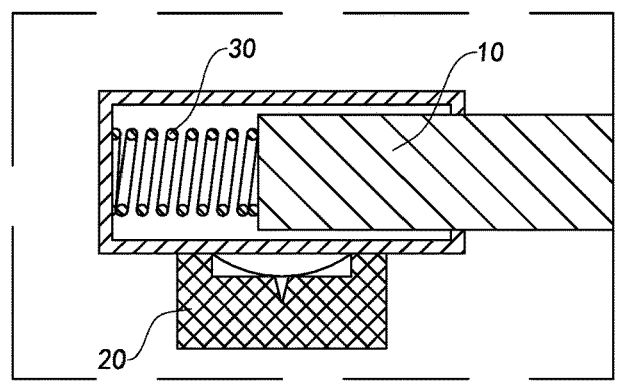
FIG. 18 is a section schematic view of the hand support device according to another embodiment of the present invention.
Figure 19:
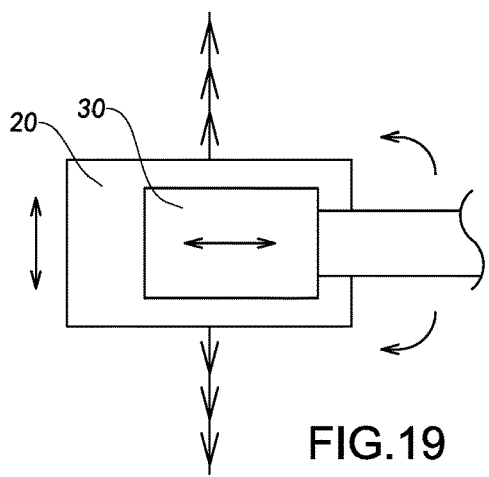
FIG. 19 is a section schematic view of the hand support device according to another embodiment of the present invention.

In another embodiment according to the FIG. 18 and FIG. 19, the first pillar and bar joint and the second pillar and bar joint are implemented as spring close casings that provides additional freedom for horizontal angular motion support on the bars, while maintaining the desire bar separation or bar union between the bars throughout the time of usage. The first pillar and bar joint and the second pillar and bar joint in a different open casing configuration are also the location where the bars can slide form the opposites side to provide an escape sliding bar release system for the purpose of moving the bar and the user's upper extremities together from side to side, from right to left and vice versa.

Figure 20:
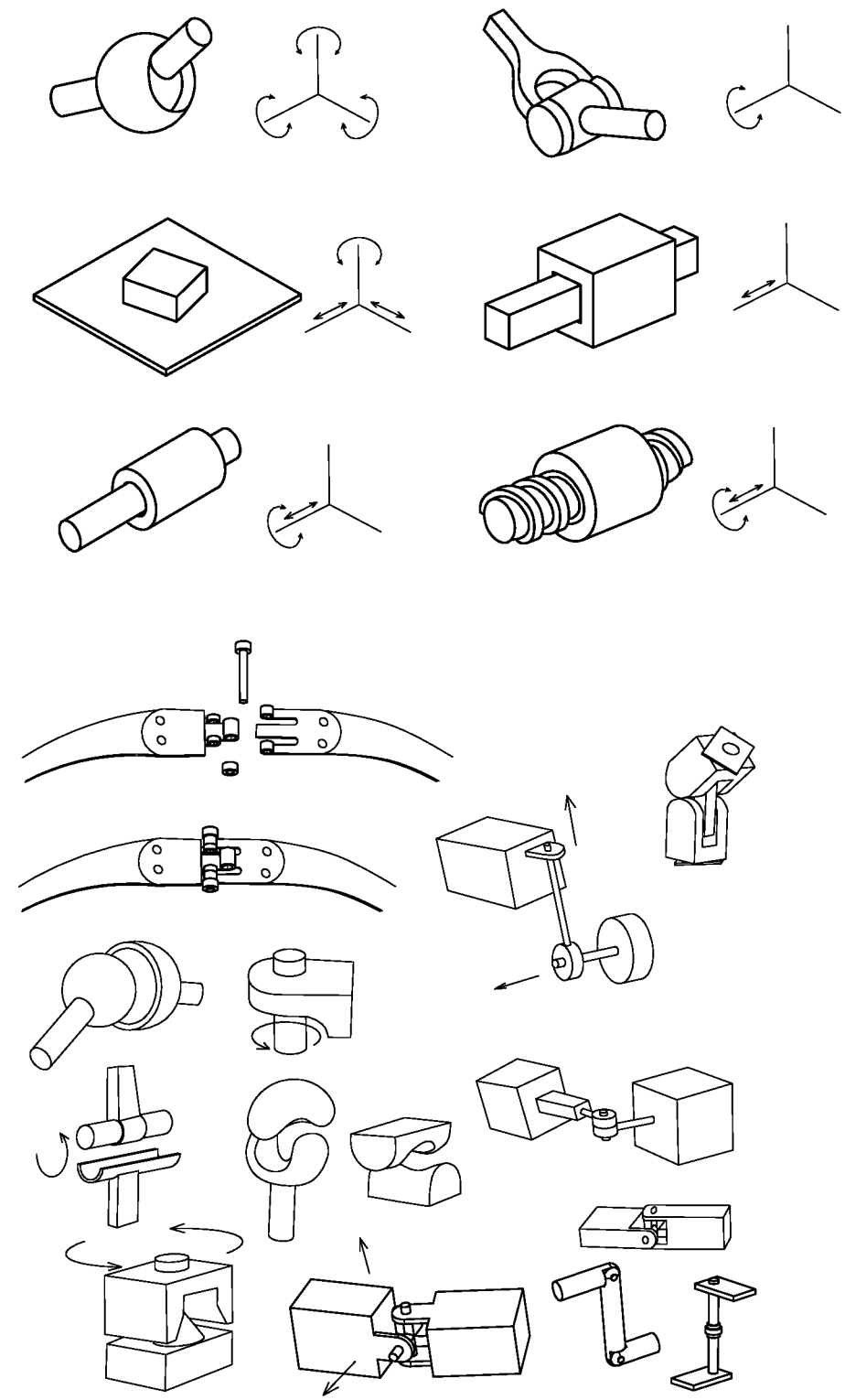
FIG. 20 is a partial view illustrating a pillar and bar joint assembly of the hand support device of the present invention.
Figure 21:
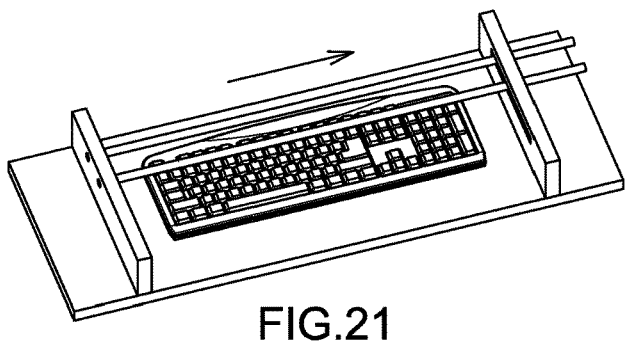
FIG. 21 is a section schematic view of the hand support device according to another embodiment of the present invention.
Figure 22:
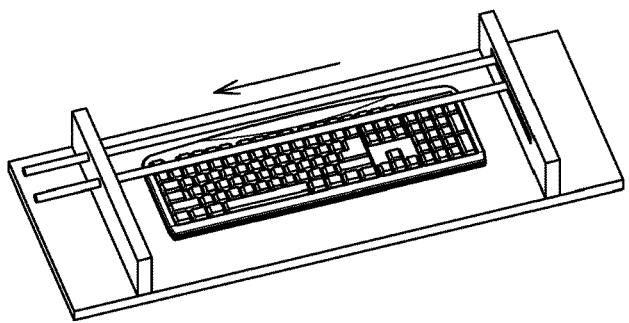
FIG. 22 is a section schematic view of the hand support device according to another embodiment of the present invention.

In addition to the embodiments above, the first pillar and bar joint and the second pillar and bar joint can be implemented as any mechanical structure likely shown in the FIG. 20. In other words, the embodiments above are example not limited. In other words, in some embodiments, the bars can freely spin clockwise and counter clockwise so that the bars can spin forward or away from the user applied any mechanical structure likely shown in the FIG. 20. In addition, the bars can be locked to stop the free spin motion in either direction or completely which is convenient for the direction and posture adjustment.

In another embodiment, the pillar joint assembly is implemented as a partial or complete concave or convex ball and socket joint movement system position on the pillar. Furthermore, the pillar joint assembly can be in any axis up or down side to side in relation to the middle central equator axis between the concave and the convex union. In other words, the pillar joint assembly provide the bars the ability to have angular horizontal motion in relation to the first base unit and the second base unit on each side of the opposite side on the keyboard or laptop. The system permits the user to move any hand up and down independent of the other hand and fingers for positioning because the ball and socket is free to rotated side to side in respect to the perpendicular horizontal plane on each side.

According to the hand support device in the present invention, the pre-existing keyboard or laptop as a premanufacture device attaches to the hand support device, wherein the present invention of the hand support device does not need to produce the keyboard, input apparatus such as typing apparatus like keyboard or laptop. The premanufacture keyboard or laptop comes in different sizes, wherein the hand support devices in the present invention are arranged in various specific ranges of measurements that provides just the right levels of additional adjustments to provide optimal utilization, and more convenience to the user. The hand support device of the present invention takes into account numerous additional adjustments, each user will need. It is important to mention the invention, in no way is made to be limited from future potentials of being produce as a built in single device unit where the hand support device are buildin, onto the keyboards, laptops, game devices and input apparatus such as typing apparatus like keyboard or any other computing devices where typing or repetitive finger, hand movements are required.

Figure 23:
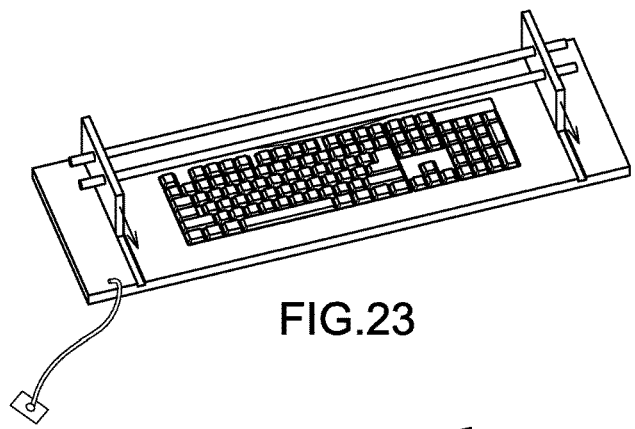
FIG. 23 is a section schematic view of the hand support device according to another embodiment of the present invention.
Figure 24:
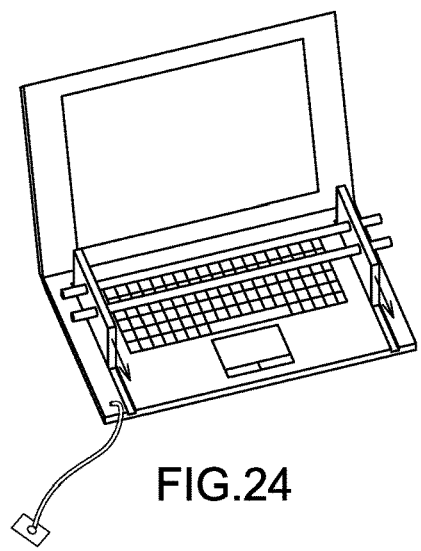
FIG. 24 is a section schematic view of the hand support device according to another embodiment of the present invention.

According to the base assembly 60, it can elevate on either end and is connected to the support base assembly 20 that can move up and down in relation to the input apparatus such as typing apparatus like keyboard, it is important to mention the keyboard or laptop position and location is fix without any additional movements, The present invention mainly illustrates an attachable hand support device for the purpose of describing, and explaining details of the present invention. As shown in FIG. 23, the hand support device is built in the keyboard, as shown in FIG. 23. FIG. 24 illustrates that the hand support device is built in onto the laptop with electrical wiring connecting to power source or other electrical appliances such as therapeutic devices.

Figure 24A:
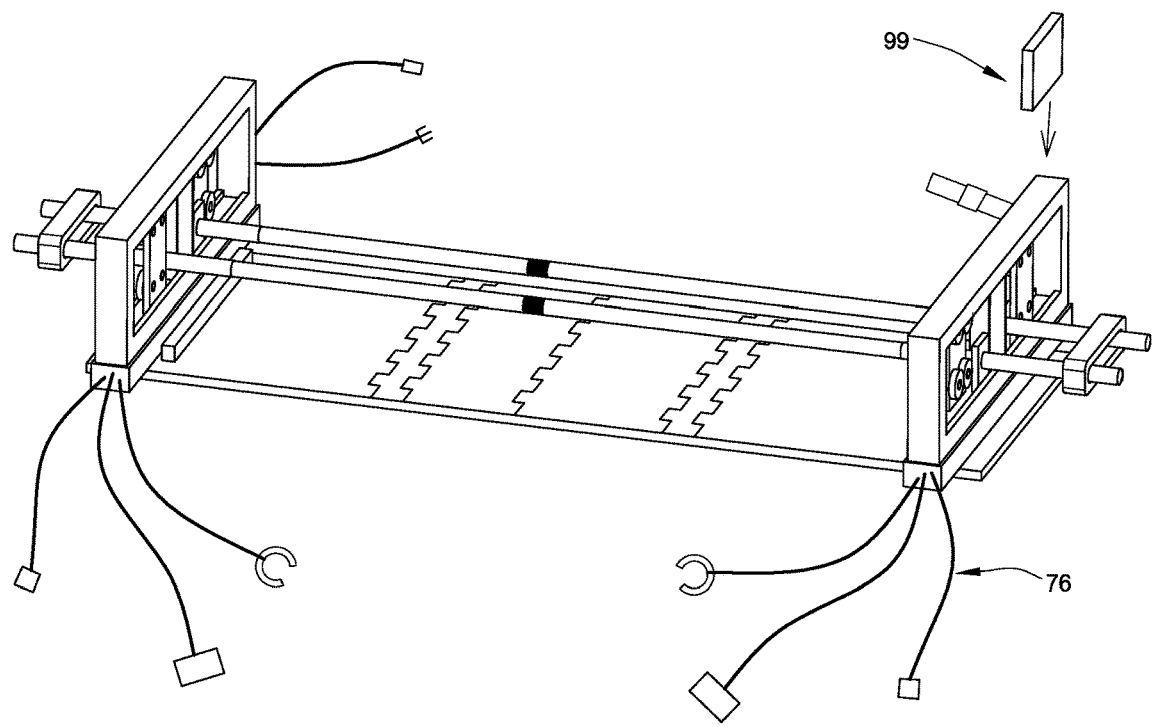
FIG. 24A is a perspective view of a hand support device according to another embodiment of the present invention.

FIG. 24A illustrates another embodiment of the hand support device of the present invention, wherein electrical wires or leads are extended therefrom to electrically connect with external devices, such as USB, mouse, therapeutic cartridge, therapeutic electro pads or deahs, earphones, camera, internal therapeutic device, and the like.

Referring to FIG. 25 of the drawings, in regards to the numerous gears for movement and adjustments in relation to comfort and performance of the hand support device.

Figure 26:
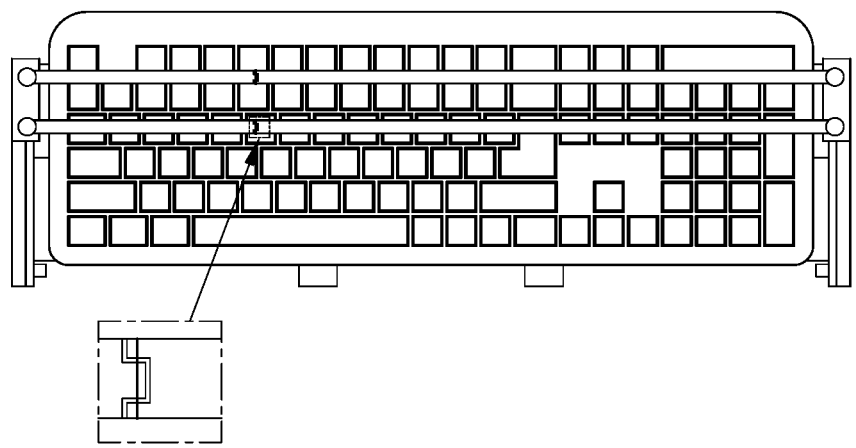
FIG. 26 is a schematic view of a hand support device according to another embodiment of the present invention.

Referring to FIG. 26 of the drawings, the bar/pillar/base system in the hand support device in relation to the keyboard, top view.

Figure 27:
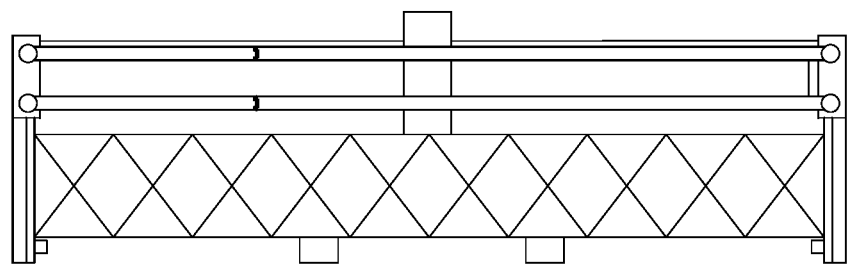
FIG. 27 is a schematic side view of the hand support device according to another embodiment of the present invention.

Referring to FIG. 27 of the drawing, the bar/pillar/base system in the hand support device without the keyboard, top view.

Figure 28:
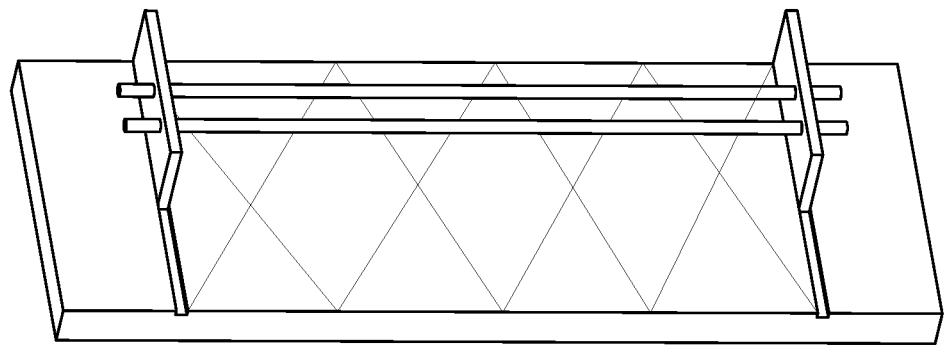
FIG. 28 is a schematic view of the hand support device according to another embodiment of the present invention.

Referring to FIG. 28 of the drawing, the bar/pillar/base system top view and bottom view of the same hand support device.

Figure 29:
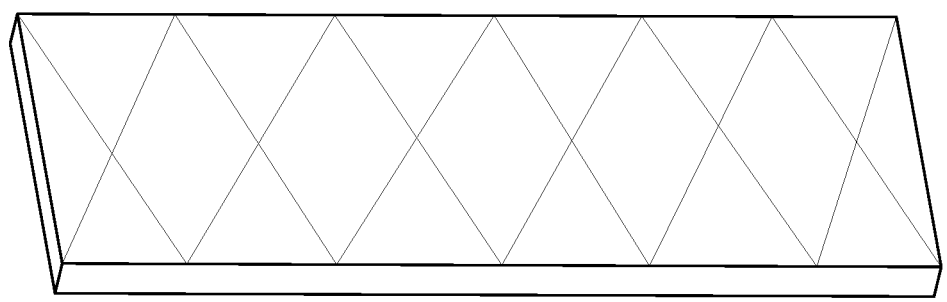
FIG. 29 is a schematic view of the hand support device according to another embodiment of the present invention.
Figure 29:
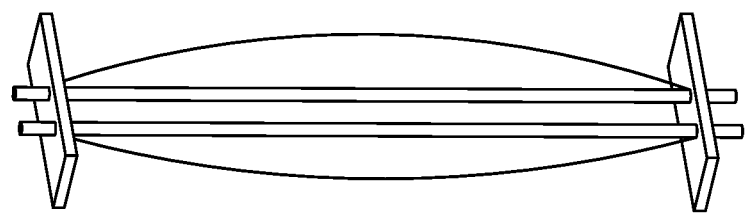

Referring to FIG. 29 of the drawing, is a detach bar/base unit where the bar or bars can be cover by a pad like material that is soft, elastic, rubbery, durable, and sturdy as another example of the present invention.

Figure 30A:
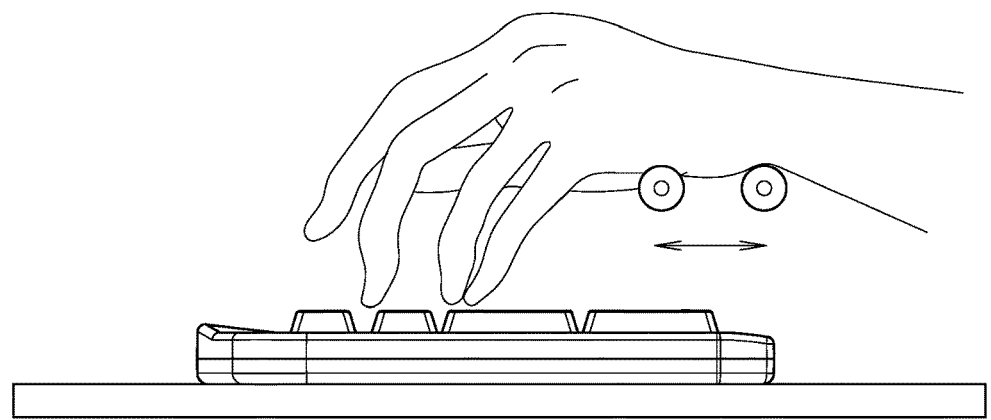
FIGS. 30A to 30C illustrate the hovering position of the hand to the input apparatus such as typing apparatus like keyboard in relation to the bar or bars and the bars to the brace with and without additional therapeutic gloves.
Figure 30B:
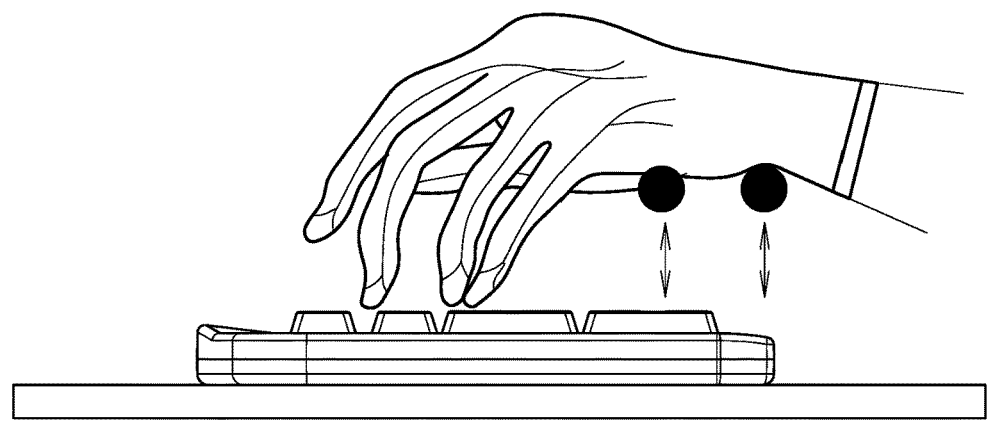
Figure 30C:
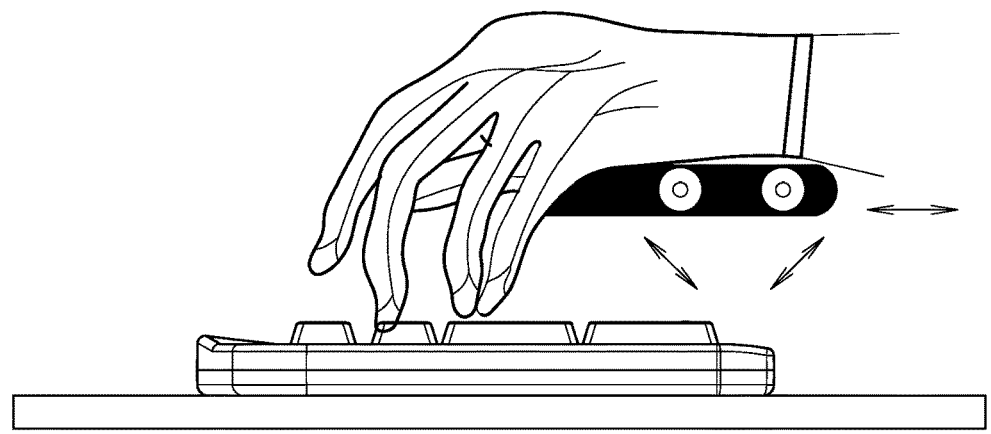

Referring to FIGS. 30A to 30E of the drawings, FIG. 30A illustrates a cross view of the hand support device without the pillars, illustrating the position of the hand without gloves hovering neutrally over the bars in regards to the location of the input apparatus such as typing apparatus like keyboard, where the bar and or sleeve is making contact with the users skin, for the purpose of support and providing optional treatment care. FIG. 30. illustrates a cross view of the hand support device without the pillars, illustrating the position of the hand with gloves hovering neutrally over the bars and or sleeves in regards to the location of the input apparatus such as typing apparatus like keyboard, where the bar and or sleeves are making contact with the users gloves for the purpose of delivering additional therapy throughout the glove and providing additional shock support. FIG. 30C illustrates a cross view of the hand support device without the pillars, illustrating the position of the hand with gloves hovering neutrally over the bars and or sleeves in regards to the location of the input apparatus such as typing apparatus like keyboard, where the brace is mounted on the bar or sleeve for additional therapy and where the glove outside volar surface are in contact with the brace to transfer current onto the inside of the glove that is in contact with the users skin for the purpose of providing additional optional treatment care and support. It is important to mention the brace can be used without the glove and the user will also be able to receive the optional therapeutic modalities.

Figure 30D:
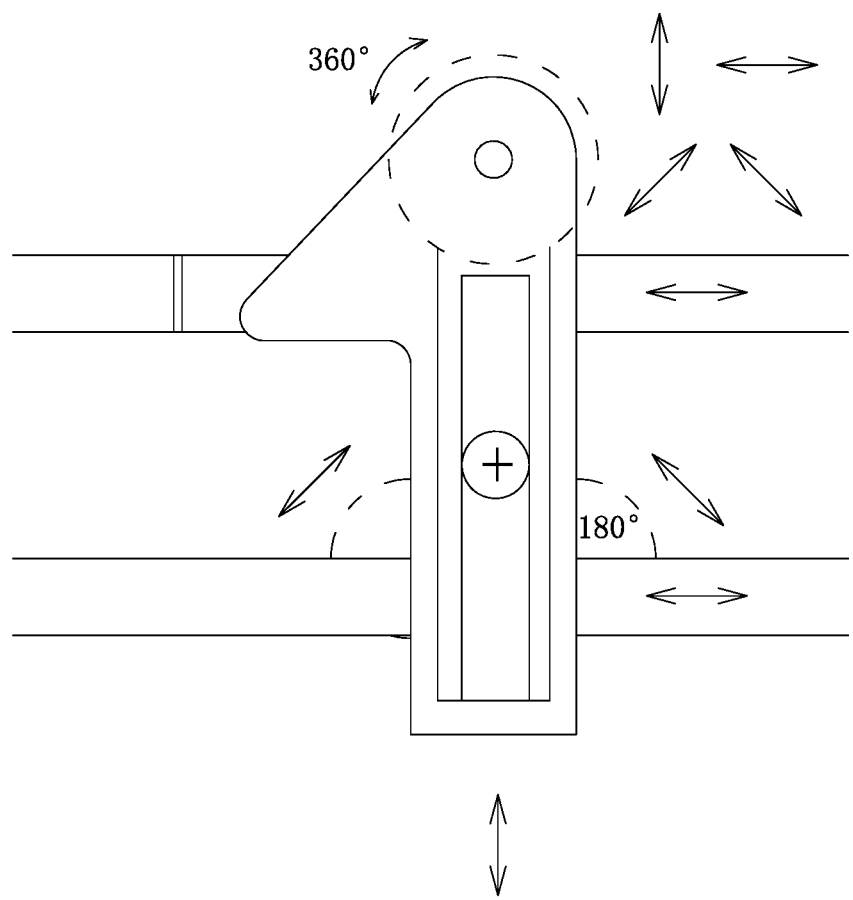
FIG. 30D illustrates the brace movement of the hand support device according to the preferred embodiments of the present invention.

FIG. 30D illustrates the various shapes, sizes, and composition of the brace and more important the synergy function the bar or bars and the braces have in common for the purpose of supporting the hand while therapy is in process. The shape can be rectangular, circular, triangular, and or square, in any combination. The sizes will range from small, medium and large. The brace will give the user a 180 degrees rotation reach where the brace can be moved and locked anywhere throughout the horizontal length of the bar or bars while supporting the user's hands. The brace also functions with a 360 degrees rotational circular support under the user wrist for additional wrist reaching movements. It is important to mention the brace can have the electrodes on any location on the brace, the bar or bars are the means by which the current can get to the brace and make contact with the user skin to deliver different therapeutic modalities. Any and all rotations on the brace in relation to the mechanical support on the upper extremities can be locked independent of the location of the brace on the bar or bars. The braces can also have and up and down vertical motion and can also be locked at a proximal or distal position in relation to the vertical distance between the user and the keyboard. The brace can be made of fiber organic composites, glass, wood, plastic, ceramic composites, rubber, carbon, metallic alloys, or any of these combinations together as a hold or in sections throughout the brace.

It is important to mention the circular micromotion of the braces and bars have due to the vertical up and down sliding pillars motion with the horizontal right and left over extension motion of the bar or bars on the pillar joints together, the vertical and horizontal motions, including up-and-down motions and left-and-right motions, enable the bars/brace system to have an elliptical and/or circular motion in relation to the keyboard or input apparatus such as typing apparatus like keyboard.

The keyboard or input apparatus such as typing apparatus like keyboard can have a neutral parallel elevated plane or a flat decline in relation to the counter surface. The keyboard or input apparatus such as typing apparatus like keyboard can also be elevated on the proximal bottom edge of the keyboard to create a forward decline grade or be elevated on the distal top edge of the keyboard to create a backwards decline grade at 70 degrees. The user can also give the right and left side of the keyboard or input apparatus such as typing apparatus like keyboard an elevation to create a tilt on either side of the keyboard or input apparatus such as typing apparatus like keyboard. The keyboard or input apparatus such as typing apparatus like keyboard can be provided all of these movements through the use of the mount plate, as mention before or through the use of structural wedge support under the keyboard or the input apparatus such as typing apparatus like keyboard. Accordingly, the wrists of the user resting and being supported on the bars of the hand support bridging unit in the wrist support typing posture are able to move up-and-down and left-and-right above the typing apparatus, as shown in FIGS. 30A to 30C, so that the user has no need to bend his or her wrist left and right and to stretch or bend his or her fingers to reach different keys on the keyboard that is the main cause of the joint injury to the wrists and fingers of those users who need to type for relative long time continuously. Instead, the user may naturally hang down his hands and fingers from his or her wrists which are well supported by the hand support bridging unit 1 during typing naturally and neutrally while moving the whole hands vertically and horizontally above the typing apparatus by means of the hand support device of the present invention.

Figure 30E:
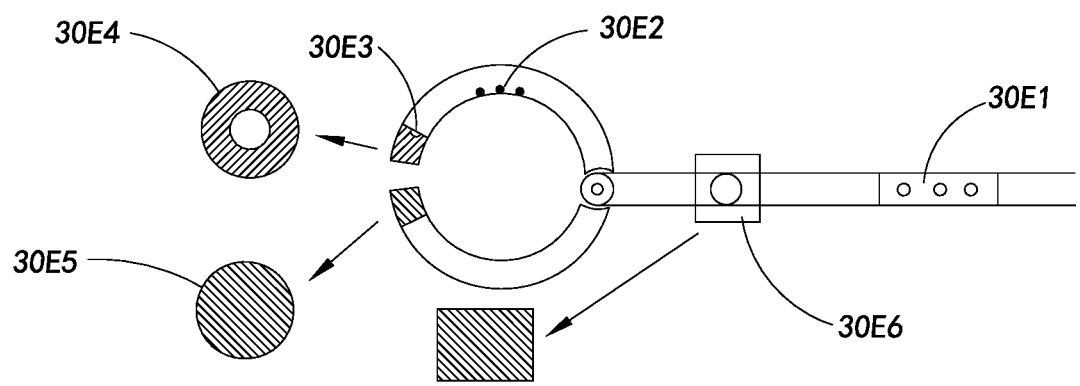
FIG. 30E illustrates a CES (Cranial Electrotherapy Stimulation) lead earpiece adapted to equip with the hand support device according to the above preferred embodiments of the present invention.

Referring to FIG. 30E, the Cranial Electrotherapy Stimulation (CES) lead will provide an earpiece with acupressure capabilities to be place on specific trigger points on the outer ear throughout the helix and the antihelix for acupressure areas and to provide treatment of anxiety, insomnia, and depression at the same time. Additionally, the Cranial Electrotherapy Stimulation (CES) leads can be place on the mastoid process with an electro patch with or without the earpiece for acupressure. Specifically, the Cranial Electrotherapy Stimulation (CES) leads can have a build-in speaker and the earpiece can have a audio hearing capacity to enable the user to multi-task as previously mention in this invention. It is important to mention the metallic tip provides the current treatment on to the conductor piece, and on to the pressure conductor, and all three pieces are interchangeable parts for the comfort and delivery on to different users. The conductor piece surrounds the metallic tip that provides current and counter pressure to the pressure conductor, where both the conductor piece and the pressure conductor can be saturated in a liquid solution to enhance electrical conduction.

In general, the present invention dose various efforts to provide adjustment for positioning as the means to providing a quality tool to provide support assistances and wellness to the consumer for repetitive hand, wrist and fingers movements. With the invention, the keyboard hand therapeutic support device is an attachment unit for an existing keyboard or laptop and\or to have itself on a fix keyboard or laptop premanufactured. A set of ranges in all the measurements, lengths, diameters, width, sizes and horizontal/vertical angular degrees have been proven to provide the maximum result to the majority of the human population dimensions.

Figure 31A:
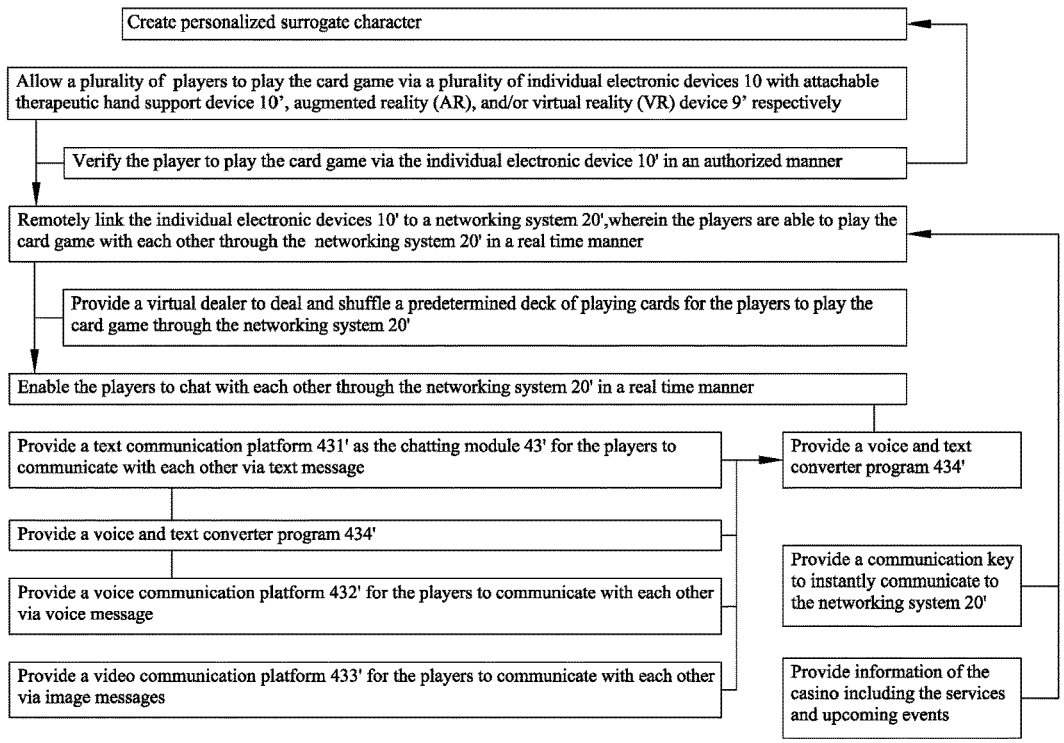
FIG. 31A is a flow chart of a method of playing games according to a preferred embodiment of the present invention.

Referring to FIG. 31A of the drawings, a method of operating an electronic device with a detachable or attachable hand therapeutic support device for playing games, especially for card games, according to a preferred embodiment of the present invention is provided, wherein the method comprises the following steps.

(a) Allow a plurality of players at least to play a game or process of at least a software or application via a plurality of individual electronic devices with a detachable or attachable therapeutic hand support device 10' as described preferred embodiments respectively.

(b) Remotely link one or more of the individual electronic devices with the detachable or attachable therapeutic hand support device 10' as described in the above preferred embodiments to a networking system 20', wherein the players or users are able to play the same game or process the same software or application with each other through the networking system 20' in a real time manner.

(c) Enable the players to chat with each other through the networking system 20 in a real time manner, wherein the players or users are able to remotely and simultaneously play the game or process the software or application and chat with each other via the individual electronic devices with the detachable or attachable therapeutic hand support device 10' as described in the above preferred embodiments through the networking system 20', such that the networking system 20' forms not only a playing or processing channel for the player or user to play the game or to process the software or application but also a communication channel for the players or users to chat so as to enhance the entertainment of the game or the software or application.

Accordingly, the networking system 20' may further comprise at least a central control 40' for centrally managing the networking system 20'. The central control 40' preferably comprises an information storage module 41' for storing a plurality of information of players or users, and a plurality of game, software and/or application programs 42' electrically and digitally stored in the central control 40' for providing variety of games, softwares or applications being remotely and virtually played or processed by the players or users.

Figure 33:
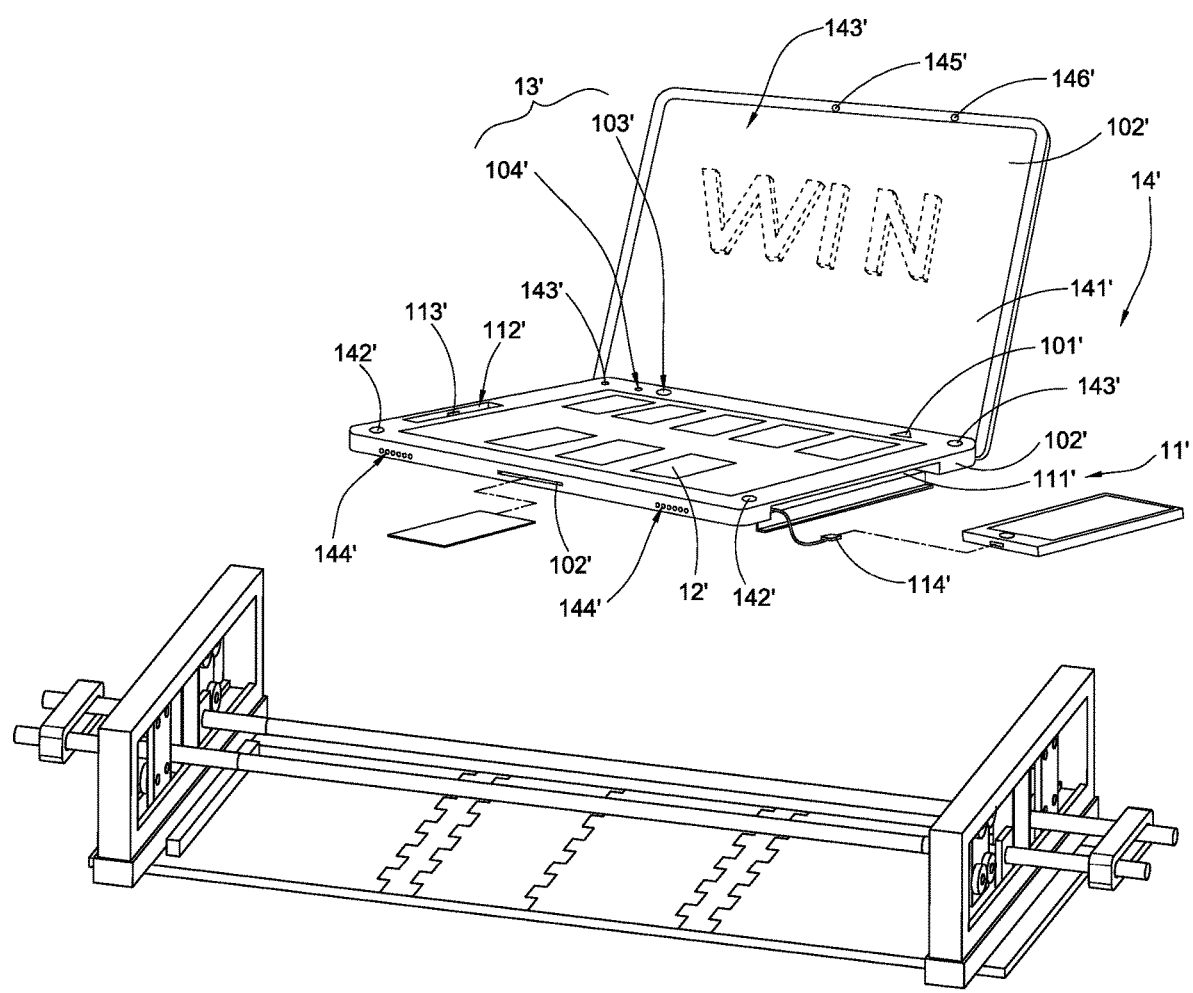
FIG. 33 is a perspective view of the electronic device and the hand support device according to the preferred embodiment of the present invention.
Figure 33A:
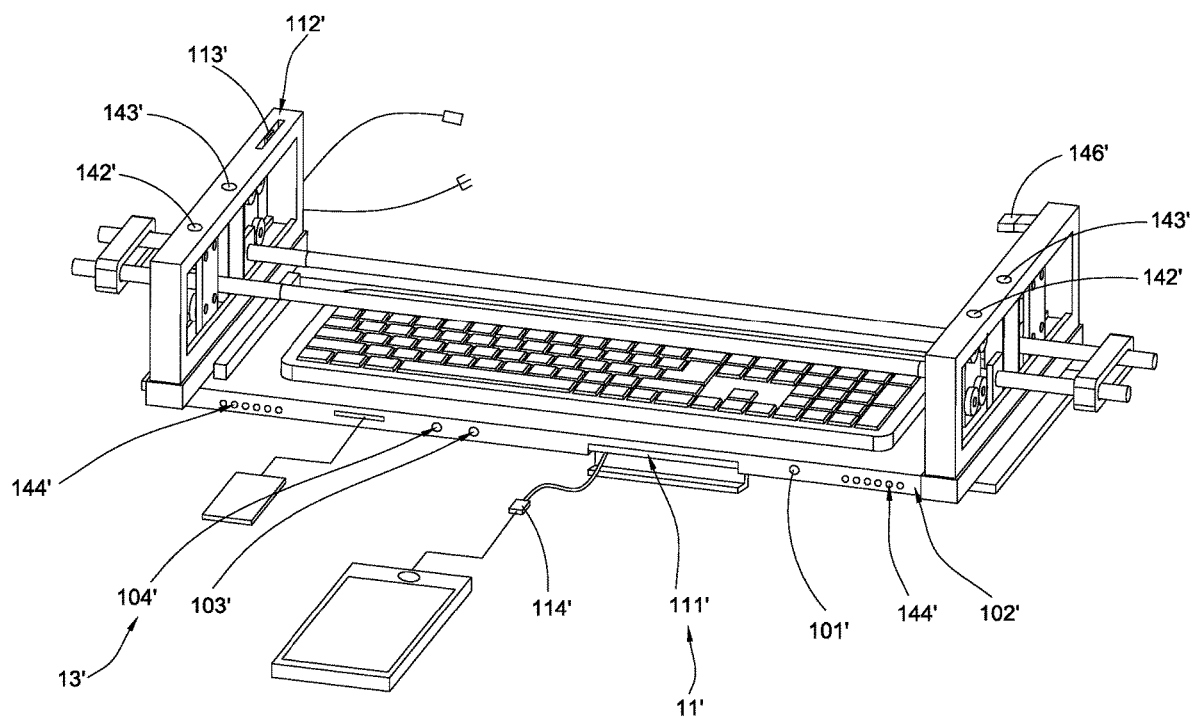
FIG. 33A is a perspective view of a hand support device according to another preferred embodiment of the present invention.
Figure 33B:
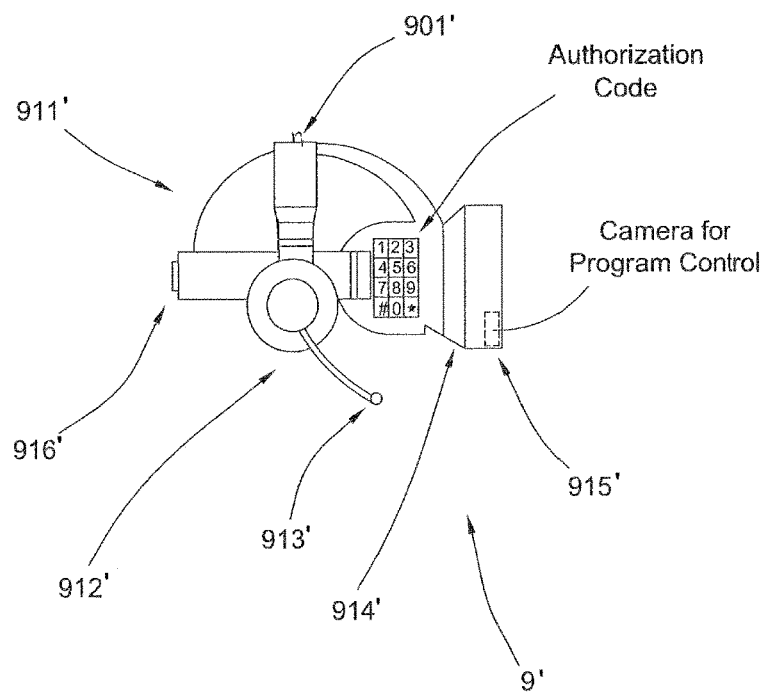
FIG. 33B illustrates an augmented reality and virtual reality (AR/VR) device embodied as the electronic device according to the preferred embodiment of the present invention.
Figure 33C:
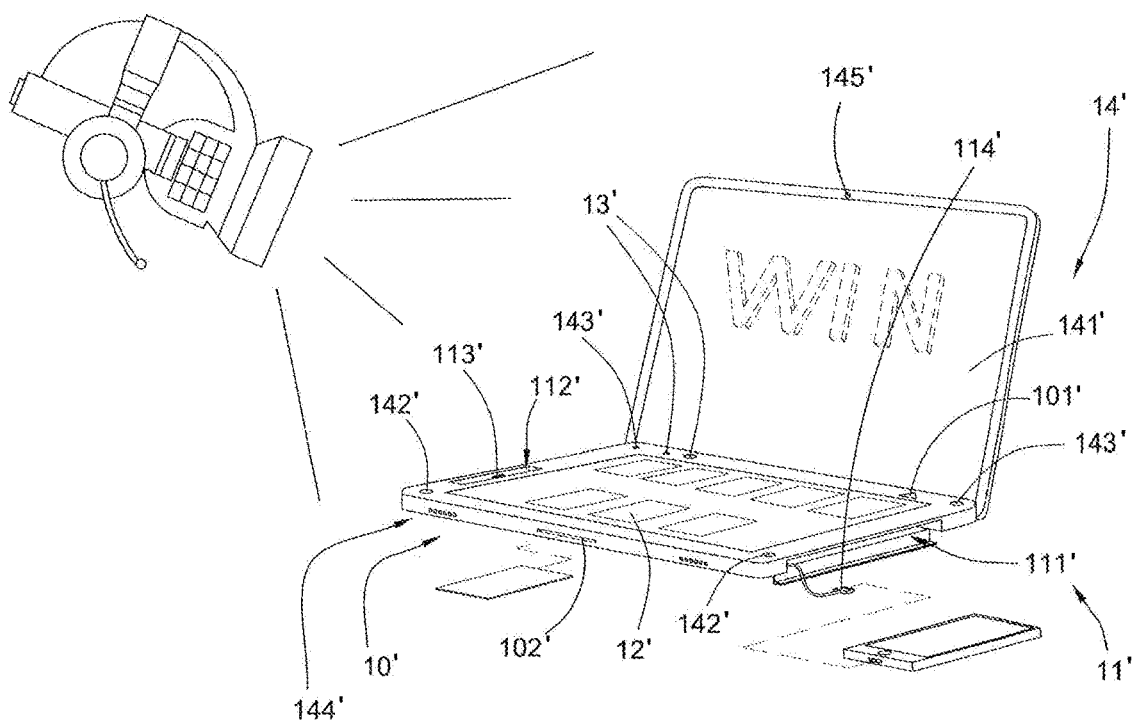
FIG. 33C illustrates the image of the AR/VR operator to be seen in the AR/VR device of the FIG. 33B in relative to the operation and functions according to the preferred embodiment of the present invention.
Figure 33D:
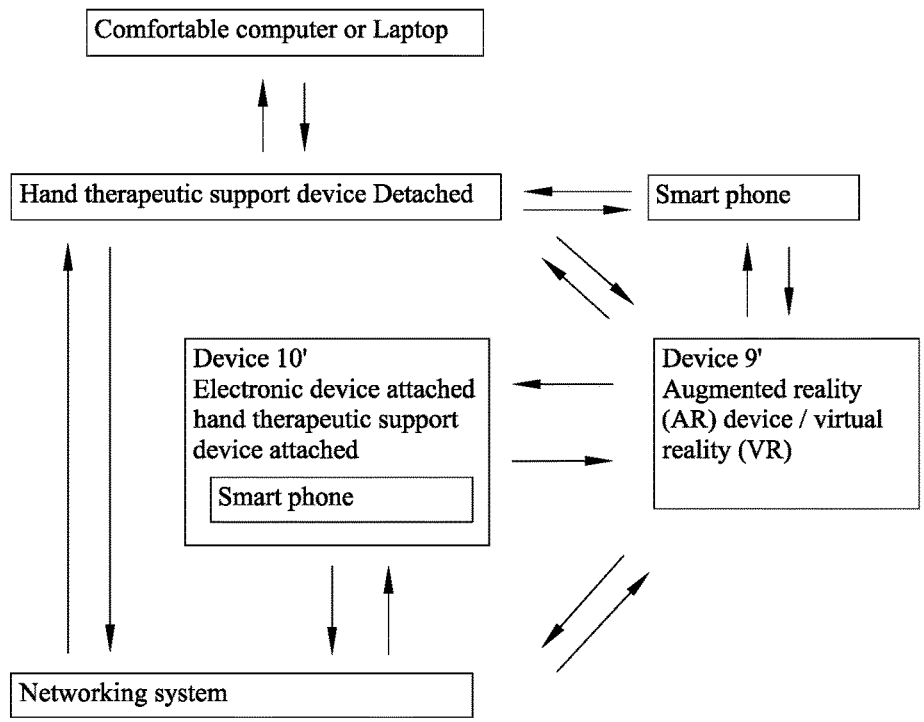
FIG. 33D is a block diagram illustrating the interacting of the electronic device, the AR/VR device, the smart device, and the networking system according to the preferred embodiment of the present invention.
Figure 35:
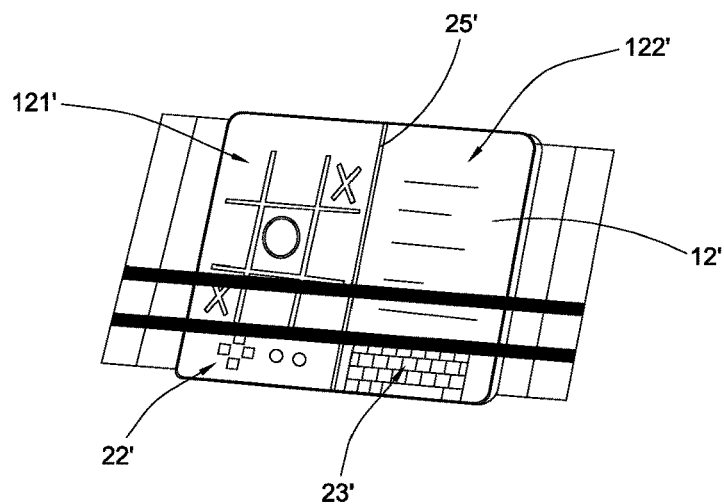
FIG. 35 illustrates the electronic device as a tablet computerized device according to the preferred embodiment of the present invention.
Figure 36A:
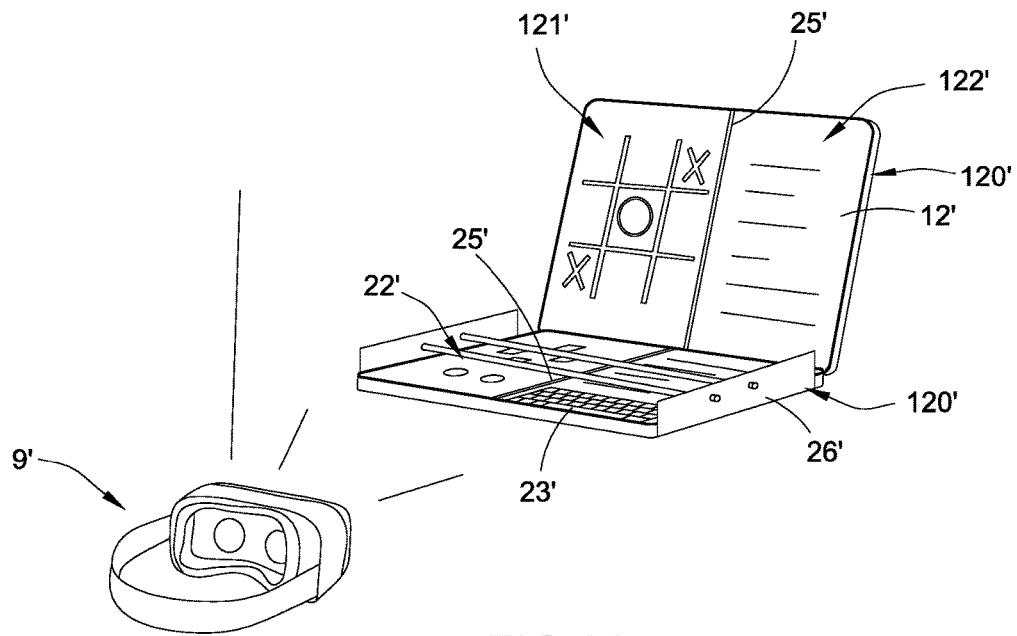
FIGS. 36A to 36C illustrate various settings of the electronic device as a laptop-like computerized device according to the preferred embodiment of the present invention.
Figure 36B:
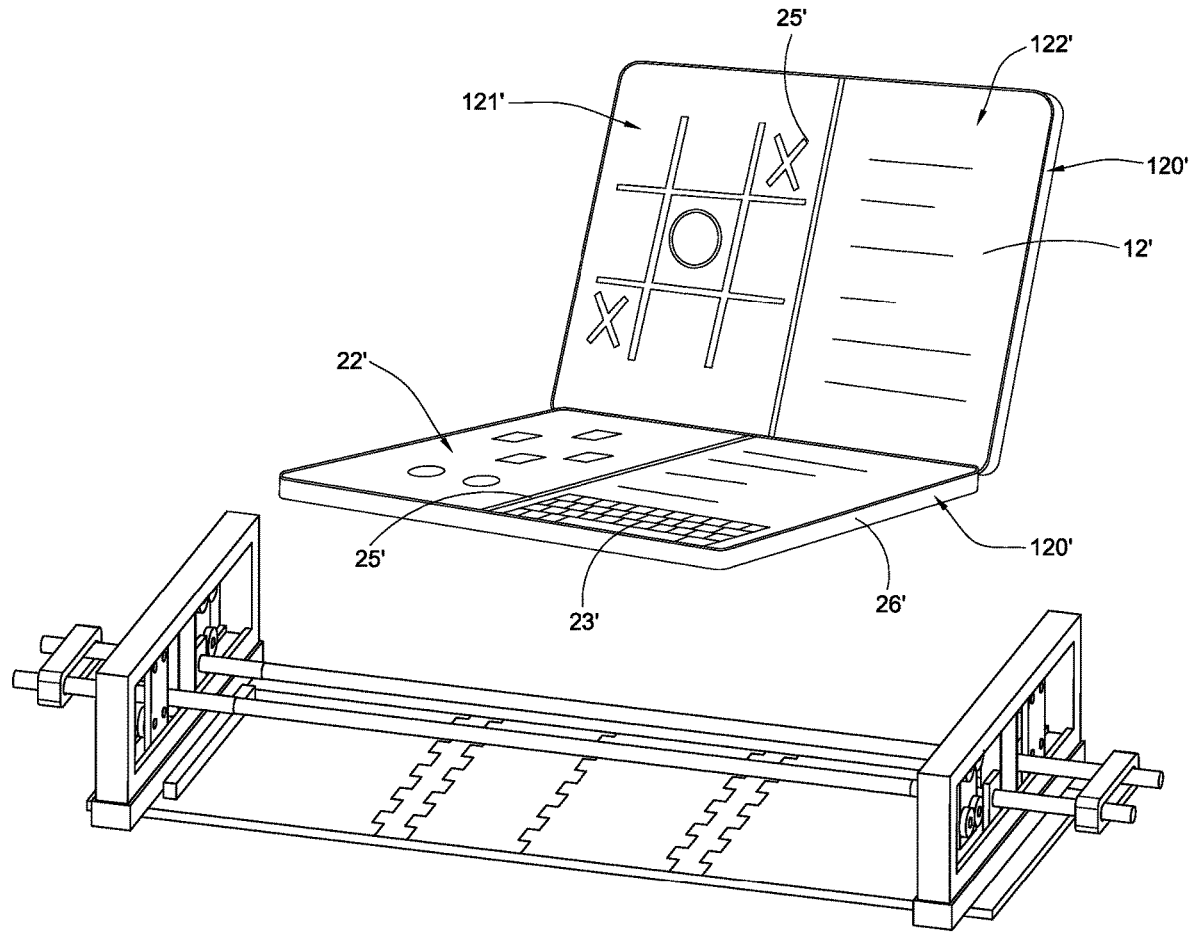
Figure 36C:
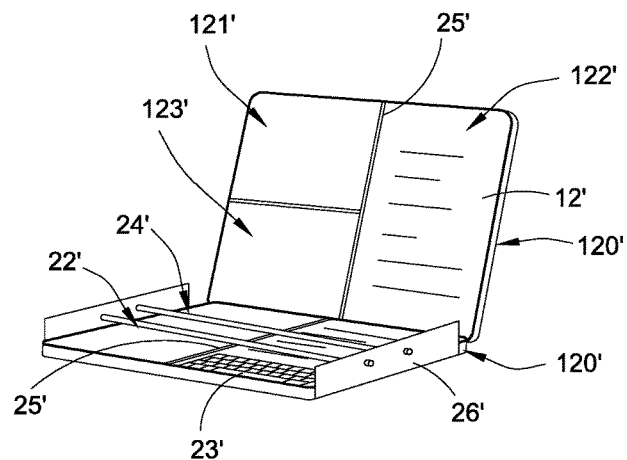

According to the preferred embodiment of the present invention, the electronic device with the detachable or attachable therapeutic hand support device 10' as described in the above preferred embodiments can be a notebook type electronic device with a detachable or attachable hand therapeutic support device as illustrated in FIG. 33, an augmented reality and virtual reality (AR/VR) device 9' as illustrated in FIGS. 33 and 33C, a tablet type electronic device as illustrated in FIG. 35, an innovative electronic device with a detachable or attachable hand therapeutic support device as illustrated in FIGS. 36A to 36C, and/or any other like electronic device that can be operated with a sideline program to form and display a slidable sideline on the display screen and/or the control panel of the electronic device.

It is important to mention that FIG. 33A illustrates a detachable therapeutic hand support device 10', with all the same embodiments of the electronic device with the attachable hand therapeutic device 10', as shown in FIG. 33. Where all the functions and futures are physically located on the detachable hand therapeutic support devices to interface (wireless or wire) with compatible atypical electronic computing devices. As a means, to provide the present invention to and existing computerize market, and not just an all in one new attachable electronic device. In other words, part of the invention is to incorporated most of the current existing electronic devices, like lap tops, (AR/VR) devices, computer monitors, slot machines, table electronic machines, kiosk machines, and etc., where the hand therapeutic support device can interface and link some or all of the functions of the present invention to the existing computer industry.

According to the preferred embodiment of the present invention, when the game to play is a gambling game such as card game, the central control 40' remotely linked with the individual electronic devices with the detachable or attachable therapeutic hand support device 10', as described in the above preferred embodiments, to form the virtual dealer to deal and shuffle a predetermined deck of playing cards for the players to play the game through the networking system 20'. Accordingly, the players will play the game through the networking system 20' as if they are playing the real table game.

Therefore, the players or users are able to remotely connect the notebook type or tablet type individual electronic device with the detachable or attachable therapeutic hand support device 10' and/or the AR/VR device 9' to the remote connecting module 31' for communicatively accessing the communication network 30' and for playing the games or processing the softwares or applications that the communication network 30' provided in an authorized manner. The communication network 30 can be any networks, such as a computer network, International Mobile Telecommunication network, other private internal network, and etc., so that through connecting to the designated communication network 30', the players or users are able to play the games or process the softwares or applications in a remote manner.

The arrangement preferably further comprises a chatting module 43' linked to the networking system 20' for enabling the players or users to chat with each other through the networking system 20' in a real time manner through video, image, audio, and/or text communication via the electronic devices with the detachable or attachable therapeutic hand support device 10' as described in the above preferred embodiments through the networking system 20'. The networking system 20' forms not only a playing or processing channel for the players or users to play the game or process the software or application but also a communication channel for the players or users to chat so as to enhance the entertainment of the game or the processing of the software or application, such that the players or users are able to remotely and simultaneously play the same game or process the same software or application and chat with each other via the notebook type or tablet type individual electronic devices with the detachable or attachable therapeutic hand support device 10' and/or in the AR/VR devices 9' through the networking system 20'.

It is worth mentioning that the player or user is able to search other players through the chatting module 43'. For example, the player or user is able to input the player or username in the electronic device with the detachable or attachable therapeutic hand support device 10 (including for example the AR/VR device 9') for searching a particular player or user. Likewise, the player or user is able to search different players or users within a predetermined radial range of the electronic device with the detachable or attachable therapeutic hand support device 10'. The player or user is able to set a private group for one or more designated players or users to join or a public group for any player or user to join.

According to the preferred embodiment of the present invention, the step (b) preferably further comprises a step of providing a virtual dealer to deal and shuffle a predetermined deck of playing cards for the players to play the game through the networking system 20' when the game is a card game.

The method of the present invention may further comprise a step of activating the notebook type or tablet type individual electronic devices with the detachable or attachable therapeutic hand support device 10' as described in the above preferred embodiments and/or the AR/VR devices 9' by the players or users to communicate between the players or users through the communication network 30, so that after the individual electronic device with the detachable or attachable therapeutic hand support device 10' as described in the above preferred embodiments is being activated by the player or user in the authorized manner, the player or user is able to monitor the selected game or the selected software or application on a display screen of the individual electronic device 10' and to controllably interact with the game, such as entering a common or betting for gambling type games, or the softwares or applications.

According to the preferred embodiment of the present invention, the central control 40' further comprises a verification module 44' for verifying the player or user to play the game or to process the software or application via the individual electronic device with the detachable or attachable therapeutic hand support device 10' as described in the above preferred embodiments in the authorized manner, wherein each of the players or users is able to sign in the networking system 20' to participate the games or the softwares or applications and to sign out the networking system 20' to quit the games or the softwares or applications at any time.

According to the preferred embodiment of the present invention, the verification module 44' can use the biometric technology, such as fingerprint, face recognition, hand geometry, iris recognition, or the like, to verify the person whether he or she is the authorized player or user. Preferably, a photo ID is used at the time when the player or user signs in and signs out the game or the software or application while the date and playing or processing time will be recorded.

Therefore, the step (a) may further comprise a step of verifying the player or user to play the game or to process the software or application via the individual electronic device with the detachable or attachable therapeutic hand support device 10' as described in the above preferred embodiments in an authorized manner. Each of the players or users may be able to sign in the networking system 20' to participate the game or the software or application and to sign out the networking system 20' to quit the game or the software or application at any time, so as to activate the individual electronic devices with the detachable or attachable therapeutic hand support device 10' in the authorized manner.

Therefore, the networking system 20' is able to remotely connect two or more real players at the same time for the player competing or playing against other real players or users simultaneously over the communication network 30'. It should be noted that, through the networking system 20', the players or users have no need to physically go to a predetermined gathering location, such as in a gaming room, or a gaming table, while still being able to enjoy the fun and realistic of playing games or processing softwares or applications with other real players or users.

Accordingly, the surrogate character can be created by the player or user that the surrogate character will be displayed during the playing or processing time. Therefore, other players or users will see the surrogate character instead of the actual image of the player or user. In addition, the username can also be created by the player or user such that the username will be displayed instead of the actual name of the player or user. Therefore, the player or user will be given a player ID and profiled photo ID during the game or the application. Of course, the player or user must use his or her truth person information to register and sign in the central control 40' in order to play the games or to process the softwares or applications.

A character development module 434' will be provided for the players or users to create their personalized surrogate character, wherein a plurality of fantastic computerized characters will be provided for the players or users to select in order to enhance the entertainment, processing and/or gambling experience. In addition, the character development module 434' further includes digital programs to convert drawings and voice speech into text messages or into digital tool characters.

The central control 40' may further comprises a chatting program of the chatting module 43' stored thereat, so that when two or more players or users are linked to the communication network 30' of the networking system 20' via each of the notebook type or tablet type individual electronic devices with the detachable or attachable therapeutic hand support device 10' as described in the above preferred embodiments as described in the above preferred embodiments and/or the AR/VR devices 9', the players or users are further being able to chat and talk to each other while playing the games or processing the softwares or applications over the communication network 30. Therefore, the reality of the virtual games is further enhanced.

According to the preferred embodiment of the present invention, the step (c) of the method further comprises a step of providing a text communication platform 431' as the chatting module 43' for the players or users to communicate with each other via text message through the individual electronic devices with the detachable or attachable therapeutic hand support device 10' as described in the above preferred embodiments, such as notebook, tablet, smart device, and/or AR/VR device, so as to allow the players or users to exchange written messages with each other during playing the games or processing the softwares or applications.

In addition, in order to enhance the reality of chatting with other players or users, the step (c) is preferred to comprise a step of providing a voice communication platform 432' for the players or users to communicate with each other via voice message through the individual electronic devices with the detachable or attachable therapeutic hand support device 10' as described in the above preferred embodiments, such as notebook, tablet, smart device, and/or AR/VR device, so as to allow the players or users to talk to each other during playing the games or processing the softwares or applications.

Also, the step (c) is preferred to comprise a step of providing a video communication platform 433' for the players or users to communicate with each other via image messages through the individual electronic devices with a detachable or attachable therapeutic hand support device 10' as described in the above preferred embodiments, such as notebook, tablet, smart device and/or AR/VR device, so as to allow the player or users to view each other during playing the games or processing the softwares or applications and to further enhance the reality as of playing the games or processing the softwares or applications face-to-face with other players, users and/or dealers in the real time manner.

Therefore, in order words, the chatting module 43' preferably comprises the text communication platform 431', the voice communication platform 432', and the video communication platform 433' that optimizes the reality of playing games or processing softwares or applications without physically showing up at the predetermined location, so that the player or user has relatively more freedom to play the games or to process the softwares or applications anywhere anytime.

A step of posting a record of competence in the game or the software or application for each of the players or users at the respective individual electronic device with a detachable or attachable therapeutic hand support device 10' as described in the above preferred embodiments is preferably provided. The record contains winning/losing records or working records and tax information of each of the players or users in response to the winning/losing records or working records. For example, the remains or totally amount of the cash or gambling chips of each of the players at the same game may be showed on the display screen of each of the individual electronic devices with the detachable or attachable therapeutic hand support device 10' as described in the above preferred embodiments.

Accordingly, for example, in the entertainment industrial, there are plenty of casinos or gambling rooms have the gambling type games provided for the players playing the game for betting against each other or wagering against the dealer. However, during the peak of gambling, all the table type games in the casino may be full of the players or tourists, so that the casino may face the shortage of game tables or the shortage of dealers. Therefore, the players in the casino may leave with no choose but instead going to play the machine type gambling games. However, the machine type gambling games in the casino, such as slot machines or roulette gambling machines, does not have the function to allow the players to gamble against the other real players.

Therefore, for example, the communication network 30' is further embodied as a local or private casino communication network 30' for electrically connecting two or more individual electronic devices with a detachable or attachable therapeutic hand support device 10' as described in the above preferred embodiments of one or more casino's customers, so that the players of the casino customer are able to remotely link to the communication network 30' for playing the games remotely through the individual electronic devices with a detachable or attachable therapeutic hand support device 10' as described in the above preferred embodiments. Thus, the players are able to gamble anywhere and anytime that he or she is able to connect to the casino communication network 30. In other words, the players not only have their own privacy to play the game at their own desired locations but also have communication and interaction, sociability among other players. Preferably, the electronic device with a detachable or attachable therapeutic hand support device 10' as described in the above preferred embodiments comprises a GPS unit for identifying the location of the electronic device with a detachable or attachable therapeutic hand support device 10' as described in the above preferred embodiments. Once the electronic device with a detachable or attachable therapeutic hand support device 10' as described in the above preferred embodiments is out of the casino area or outside of the range of the private casino communication network 30', the electronic device with the detachable or attachable therapeutic hand support device 10' will be disabled.

It is important to understand that the disablement of the electronic devices with the detachable or attachable therapeutic hand support device 10' is a completely disablement of all the functions of all the devices. That means no gaming, no processing, no texting, and no internet is allowed. It is not a partial disablement of a program or set of programs and, furthermore, the disablement will activate a security dormant system that is activated when the electronic device with a detachable or attachable therapeutic hand support device 10' as described in the above preferred embodiments is removed from working perimeter boundaries and or tamper within its working perimeter. It will also interact with the surrounding environment.

In a case of removal of the electronic device with the detachable or attachable therapeutic hand support device 10', the electronic device with the detachable or attachable therapeutic hand support device 10' will stop working the panic system, turn on the GPS coordinates, and be given to law enforcement. In addition, the smart phone on file will be called and also the GPS will be activated to locate the player or user that the cell towers can triangulate the smart phone position and the credit card will be charged additional penalty fee.

If the smart phone is in the phone cavity 111', the smart phone will not be released by the portable electronic device with the detachable or attachable therapeutic hand support device 10' even when the corrected password is input. Furthermore, the Internet-Of-Things (IOT) can triangulate the device as to the direction, speed and the location of the electronic device with the detachable or attachable therapeutic hand support device 10'. Lastly, the electronic device with IOT technology equipped will interact with other interactive devices, such as switching on light bulbs, turning on radios or like, announcing the location of the damaged or out-of-place electronic device with the detachable or attachable therapeutic hand support device 10' by a dedicated (IOT) speaker near an exit or around the establishment. The same will apply to any tampering of the electronic devices within the facility.

Preferably, no electronic device nor the detachable or attachable therapeutic hand support device 10' can be turn off/on. All interactive electronic devices with the detachable or attachable therapeutic hand support device 10' will be on stand-by mode at all times, charging or in used. When any of the electronic devices with a detachable or attachable therapeutic hand support device 10' is outside its charging dock and needs to be charged, the detachable or attachable therapeutic hand support device 10' will send a high pitch sound and the security features discussed above will take place except for charging the credit card. In other words, all electronic devices including the detachable or attachable therapeutic hand support device 10' that are completely off are during repairing or being locked away.

It is worth mentioning that the preferred embodiment of the present invention is not to be confused for a temporary partial authorization of a particular function in an electronic device and or in the functions of the AR/VR devices or program applications for these devices. In other words, the portable electronic devices with the detachable or attachable therapeutic hand support device 10' will be disable completely. The user will not be able to operate any function and, in addition, the dormant security embodiments mentioned before will be activated as part of the total security system. It is important to mention that the disablement of these electronic devices with a detachable or attachable therapeutic hand support device 10' are not for the management and functions of these electronic devices with a detachable or attachable therapeutic hand support device 10', but for the purpose of stopping and preventing illegal operation and crime activity in relation to when the electronic device with the detachable or attachable therapeutic hand support device 10' is provided by the establishment.

In another example, the establishment can also be embodied as an education establishment, such as a tutorial school or college, and the communication network 30' is further embodied as an educational communication network 30' for electrically connecting two or more individual electronic devices with the detachable or attachable therapeutic hand support device 10' of one or more student users thereof, so that the student users are able to remotely link to the communication network 30' for processing education softwares or applications, such as doing a joint project or homework, remotely through the individual electronic devices with the detachable or attachable therapeutic hand support device 10'. Thus, the student users are able to discuss, communicate, and doing work anywhere and anytime that he or she is able to connect to the educational communication network 30'. In other words, the student users not only have their own privacy to do the work at their own desired locations but also have communication and interaction, sociability among other group students, all while the user is receiving various therapeutic modalities medically or leisurely.

In another example, the establishment can also be embodied as a working establishment, such as a working facility, the communication network 30' is further embodied as a working communication network 30' for electrically connecting two or more individual electronic devices with the detachable or attachable therapeutic hand support device 10' of one or more employed workers thereof, so that the worker users are able to remotely link to the communication network 30' for processing working softwares or applications, such as doing a joint project or program, remotely through the individual electronic devices with the detachable or attachable therapeutic hand support device 10'. Thus, the worker users are able to discuss, communicate, and doing work anywhere and anytime even they are not at the seats as long as he or she is able to connect to the working communication network 30'. In other words, the worker users not only have their own privacy to do the work at their own desired locations but also have communication and interaction, sociability among other workers or their supervisors. Preferably, each of the electronic devices with the detachable or attachable therapeutic hand support device 10' comprises a GPS unit for identifying the location of the electronic device 10'. For example, once the electronic device with the detachable or attachable therapeutic hand support device 10' is located outside the working area or facility or is out of the range of the working communication network 30', the particular electronic device along with the detachable or attachable therapeutic hand support device will be disabled for security reasons, like military installations etc.

For instance, the players or users may be able to connect the individual electronic devices with the detachable or attachable therapeutic hand support device 10' to the communication network 30' of the establishment while staying in the establishment, such as hotel of the casino, school or working facility, while obtaining optional therapeutic modalities through the therapeutic hand support device 10'.

Accordingly, for example, the game players are able to play the casino games to wager against the virtual dealer of game program 42' installed in the central control 40' via plugging into a communication plug provided in a hotel room to wirely connect to the communication network 30' of the casino or wirelessly link to the communication network 30' of the casino with a provided password. Therefore, the players are able to remotely gamble via playing the virtual games over the communication network 30' against other real players in a real time manner.

Also, the student users are able to do their homeworks or projects through the designated softwares or applications installed in the central control 40' of the school via plugging into a communication plug provided in their dormitory or library to wirely connect to the communication network 30' of the educational facility or wirelessly link to the communication network 30' of the educational facility with a provided password. Therefore, the student users are able to remotely and jointly work via the softwares or applications over the communication network 30' with other student users in a real time manner.

Similarly, the worker users are able to do their works or projects through the designated software or application installed in the central control 40' of the working facility via plugging into a communication plug provided in the work station, meeting room, cafeteria, or etc. to wirely connect to the communication network 30' of the working facility or wirelessly link to the communication network 30' of the working facility with a provided password. Therefore, the worker users are able to remotely and jointly work via the softwares or applications over the communication network 30' with other users in a real time manner.

Figure 31B:
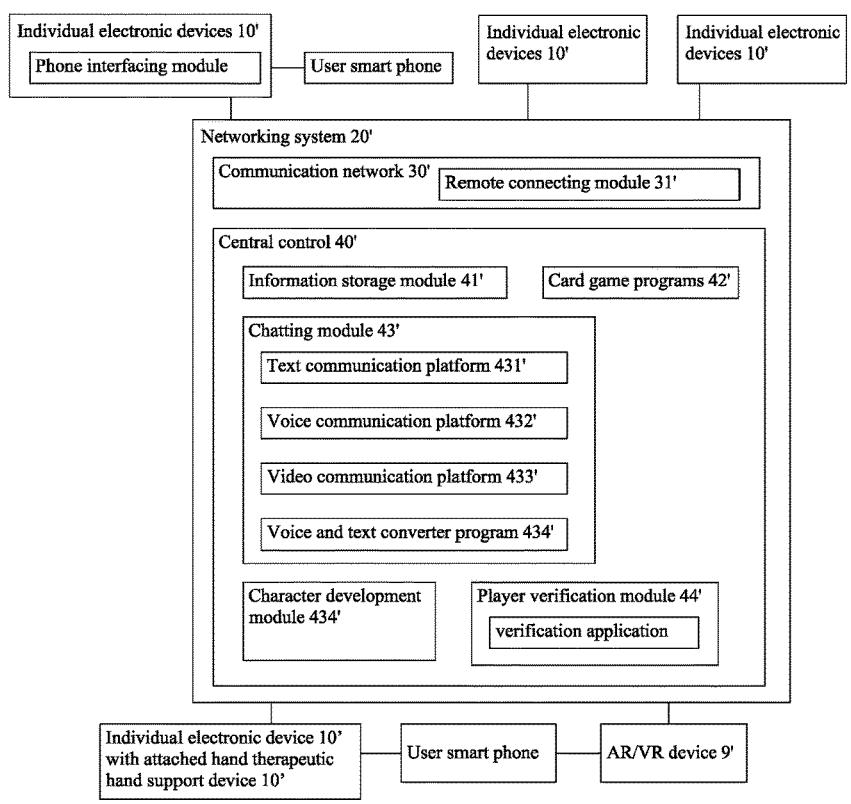
FIG. 31B is a block diagram of an operating system of two or more electronic devices according to the preferred embodiment of the present invention.
Figure 32:
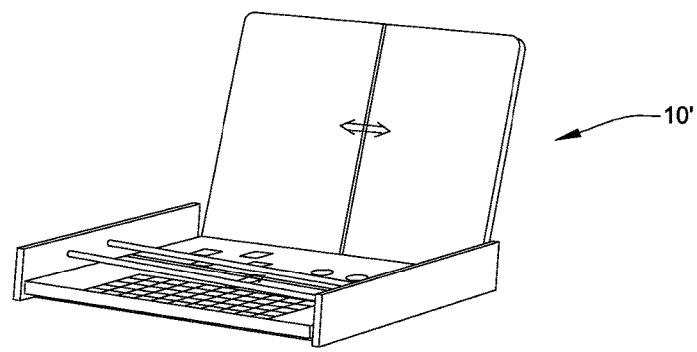
FIG. 32 is a perspective view of the electronic device and the hand support device according to the preferred embodiment of the present invention.

Referring to FIG. 31B of the drawings, the present invention further provides an arrangement of operating multi-task interactive electronic devices for playing games or processing softwares or applications through a networking system 20' thereof. The arrangement comprises the networking system 20' which preferably comprises the communication network 30 and the central control 40' as mentioned above, and the plurality of individual electronic devices with the detachable or attachable therapeutic hand support device 10', such as a notebook type electronic device as illustrated in FIG. 32-FIG. 33C, an augmented reality and virtual reality (AR/VR) device 9' as illustrated in FIGS. 33B and 33C, a tablet type electronic device with the detachable or attachable therapeutic hand support device as illustrated in FIG. 35, an innovative electronic device as illustrated in FIGS. 36A to 36B, and/or any other like electronic device adapted to be operated with a sideline program to form and display a slidable sideline on the display screen and/or the control panel of the electronic device with the detachable or attachable therapeutic hand support device 10'.

As an example, when the present invention is embodied as a method of playing games in a casino or the like as the establishment, the individual electronic devices with the detachable or attachable therapeutic hand support device 10', such as a personal computer, a notebook, a tablet, an iPad, a smart phone, a portable personal electronic device, an AR/VR device, or any other electronic devices which is able to link to the networking system 20' wired or wirelessly in the remotely connection manner, wherein the casino players are able to use the individual electronic devices with the detachable or attachable therapeutic hand support device 10' as the portable game consoles to remotely joint the networking system 20' for selectively monitoring and interacting with the games displayed on the game consoles with other real gambling players in the real time manner. In other words, each of the individual electronic devices (game consoles) with the detachable or attachable therapeutic hand support device 10' are programmed to be able to interact with the other paired game consoles with the detachable or attachable therapeutic hand support device 10' for playing the same game in real time manner.

It is worth mentioning that the casino players are able to select variety games provided in an electronic computing device with the detachable or attachable therapeutic hand support device 10', so that there is no need for players physically going to each of the gambling table for different types of games. Also, the players do not have to join the crowded gaming tables of the games while being able to enjoy playing with other players, to socialize with other players, and enjoy the entertaining environment in the casino.

The game console (electronic device) and the detachable or attachable therapeutic hand support device 10' as described in the above preferred embodiments in the casino remotely linked to the networking system 20' to communicate with the central control 40' is also programmed that the game console with the detachable or attachable therapeutic hand support device 10' is able to automatically count the winning or losing of each round of the game, so that the players may be able to collect the credit of winning or losing and cash the credit after the finishing the games. Therefore, the game consoles and the detachable or attachable therapeutic hand support device 10' are able to enhance the safety of the players by eliminating the need of carrying large amount of chips or cash, and solve the problem of the dealer shortage in casino.

In the preferred embodiment of the present invention, the method of operating multi-task interactive electronic devices for playing games may further comprise a step of providing a plurality of the game consoles as the individual electronic devices with the detachable or attachable therapeutic hand support device 10' as described in the above preferred embodiments which can be interacting with each other for playing the same game and/or chatting with each other, so that the players of the casino customers are able to operate multiple tasks with their game consoles with the detachable or attachable therapeutic hand support device 10'. For example, the players can enjoy the games simply via the display of their game consoles with the detachable or attachable therapeutic hand support device 10' to bet, monitor the games, and to remotely play with other real players who's being automatically arranged to the same virtual game room of the game via the central control 40'. Therefore, the players are able to stay in the same seat for selectively playing the games without moving around to different gaming tables of the games. Accordingly, casino will increase value of clients without having to expand casino facility size or increase extra wages for additional employees. By saving construction cost and waging cost, casino will be able to develop better services and to maintain high level entertainment quality.

As mentioned above, the arrangement may further comprise the chatting module 43' electrically stored in the central control 40', so that the players are able to play against the other players remotely connected to the networking system 20' while talking and chatting with each other, so as to enhance the reality as of playing in a real gaming table of game. In other words, the player, who is the casino resort quest, can play game any time anywhere even he or she is not presently stay in the casino resort.

The information storage module 41' of the central control 40' may store a plurality of personal information of the players, such as the ID numbers, pictures, phone numbers, names, mail and email addresses, passwords, and/or any activity records regarding the playing of the games, such as gaming dates, winning or losing thereof, and any other activities in casino. The information storage module 41' may further digitally store the cash flow information of the players, such that the players are able to directly bet against the virtual dealer of the networking system 20' and to deduct or add the amount of the cash stored in the information storage module 41' in responsive to the winning or losing of the games.

Accordingly, the information storage module 41' will store the surrogate character created by each of the players. In addition, the information storage module 41' will also store the tax information of each of the players. When the player plays each game, the gambling tax will be determined when the player wins the game. In other words, when the player logs out the game, the gambling tax will be determined and recorded in responsive to the gambling winning or losing. The gambling tax will be accumulated for a time period, such as yearly, wherein a gambling tax statement will be printed and sent to each player for tax purpose.

The communication network 30' of the arrangement is preferably embodied as a private casino communication network 30' provided for the players of the casino customers accessibly link with the communication network 30' in the authorized manner for entertaining the customers thereof. The game consoles are electrically and remotely linking to the casino communication network 30' to form the networking system 20' for remotely playing games through the game consoles with the detachable or attachable therapeutic hand support device 10' or any other individual electronic devices with the detachable or attachable therapeutic hand support device 10', such as AR/VR devices 9, in the real time manner.

The individual electronic devices with the detachable or attachable therapeutic hand support device 10' as described in the above preferred embodiments in the preferred embodiment of the arrangement, such as personal computer, notebook, tablet, or AR/VR device loaded with the sideline program as described below, may be able to activate in the hotel room of the casino wirely or wirelessly as mentioned above, so that the players of the casino customers are able to simply relax in their own rooms without physically coming out to the main gambling area of the casino, so as to further provide another way to enjoy gambling and playing games in the casino.

According to the preferred embodiment of the present invention, the players are able to remotely link to the individual electronic devices with the detachable or attachable therapeutic hand support device 10' as described in the above preferred embodiments via the casino communication network 30' through the remote connecting module 31' thereof, wherein the casino may provide a membership card or the like to each of individual players of casino customers, wherein the membership card is preferred to include a magnetic strip or smart chip that stores the corresponding personal information of the customer, so that when the membership card is being inserted into the individual electronic devices with the detachable or attachable therapeutic hand support device 10', the preloaded sideline program in the electronic device with a detachable or attachable hand therapeutic support device is activated and the communication network 30' is linking the individual electronic device with the detachable or attachable therapeutic hand support device 10' to the information storage module 41' of the central control 40' automatically, so that after confirming the players information by matching with the stored information in the information storage module 41' to authorize the activation request from the player, the central control 40' will automatically and remotely activate the computer program and the sideline program in the electronic device with the detachable or attachable therapeutic hand support device 10' to remotely link to the networking system 20'. Preferably, the photo ID is required to sign off to the individual electronic device with the detachable or attachable therapeutic hand support device 10' with date and time recorded. Therefore, the individual storage module 41' is able to link to the individual electronic devices with the detachable or attachable therapeutic hand support device 10' for posting the record of the competence in the game for each of the players at the respective individual electronic device with the detachable or attachable therapeutic hand support device 10'.

Alternatively, the individual electronic device (game consoles) with the detachable or attachable therapeutic hand support device 10' as described in the above preferred embodiments may be activated by providing the predetermined account, the user name and the corresponding passwords thereof, so that the players are able to enter the user names and passwords to submit to the central control 40' for being authorized to activate the individual electronic devices through the utilization of the detachable or attachable therapeutic hand support device 10'.

Alternatively, the electronic device (game console) with the detachable or attachable therapeutic hand support device 10' as described in the above preferred embodiments can also be activated by inserting a financial card, such as credit card, debit card, or the likes, so that the private casino communication network 30' may direct the players to the central control 40' for accessing the game programs 41' to remotely play the games through the individual electronic devices with the detachable or attachable therapeutic hand support device 10' supported by the sideline program and to automatically deduct all charges from playing the games directly from player's financial card.

Alternatively, the individual electronic device (game console) with the detachable or attachable therapeutic hand support device 10' as described in the above preferred embodiments is provided with input devices, including but not limited to a front/back camera 145' for image capturing and face recognition or, alternatively, a motion sensor 146 for motion detection, an image (holograph/light) projector 143' for non-touch interactive display motion and voice command, a microphone 142' for voice capturing, voice recognition, voice command, and/or a fingerprint scanner for fingerprint recognition, to function as activation tool of the electronic devices as well as the sideline program loaded in the electronic device with the detachable or attachable therapeutic hand support device 10', so that the individual electronic devices with the detachable or attachable therapeutic hand support device 10' and the sideline program can be activated by recognizing the player's face, voice and/or fingerprint which is submitted to the central control 40' for being authorized to activate the individual electronic devices with the detachable or attachable therapeutic hand support device 10' for accessing the game programs 41' to remotely play the games through the individual electronic devices, to operate the individual electronic devices with the detachable or attachable therapeutic hand support device 10' with the supporting sideline program, and to automatically deduct all charges from playing the games directly from the player's final card.

It should be noted that the membership card can also integrate with the room card key of the casino hotel, so that the casino can easily charge the fee of the entertainment of playing game through the room payment account of the players. The membership card can have variety of shapes, such as traditional flat rectangular shaped magnetic card or IC card, or chips shaped having magnetic sensor therein for electrically communicating with the individual electronic devices with the detachable or attachable therapeutic hand support device 10', in such a manner that the players are able to conveniently activate the individual electronic devices with the detachable or attachable therapeutic hand support device 10' and saving or transferring a predetermined amount of cash or credit therein without carrying around actual casino gambling chips or cash. It is worth mentioning that the players can also pay or paid through their smart phone application such as "Wallet", "ApplePay", "Alipay", "Bitcoin", or the like. The casino is able to securely manage the authorization of the players to enhance the security of casino. The information of the player, including credit card information and personal information, will be encrypted and stored, such tokenization, for enhancing the data security.

Therefore, the method of operating multi-task interactive electronic devices for playing games may further comprise a step of authorizing the remotely submitted activation requests by the players via each of the individual electronic devices with the detachable or attachable therapeutic hand support device 10' as described in the above preferred embodiments. Accordingly, the players are able to securely activate the individual electronic devices with the detachable or attachable therapeutic hand support device 10' for linking with the communication network 30', such as the private casino communication network 30' via the remote connecting module 31', so as to enhance the safety of the players and the casino. The authorizing of the activation requests of the players may be performed via providing the membership cards, or any of the above mentioned methods to accomplish the authority of the players via the individual electronic devices with the detachable or attachable therapeutic hand support device 10'.

It is worth mentioning that the electronic device with the detachable or attachable therapeutic hand support device 10', i.e. the portable game console, may be provided in every guest room as standard casino equipment ready to be utilized by the hotel guests of that particular room or requested on demand. For example, the same credit card of the user for the hotel will link to electronic device with a detachable or attachable therapeutic hand support device 10' as described in the above preferred embodiments for security purpose so as to provide the casino guests the correct financial statement. Criminals will be less likely to stay overnight. It is also important to mention GPS is in every electronic device with the detachable or attachable therapeutic hand support device 10'. This is why GP is so important to the collective operation of the present invention. Another safety feature that is link with the GPS is that the electronic device with the detachable or attachable therapeutic hand support device 10' will stop all operations when the electronic device is located outside its predetermine intranet working area. It is also worth mentioning when the electronic device with the detachable or attachable therapeutic hand support device 10' is back in its working territory, the electronic device will not return to operational capacity. The electronic device with the detachable or attachable therapeutic hand support device 10' must be return to the casino for evaluation and maintenance for a complete total restart-up of all devices. When and where all electrical devices are property of the casino or agents of the casino.

As will be readily appreciated by one skilled in the art, the arrangement of playing game preferably further comprises a private casino communication networking platform for remotely linking with the individual electronic devices with the detachable or attachable therapeutic hand support device 10' in the authorized manner and for providing an interface for the player managing their private account information and selectively controlling and monitoring the games through the individual electronic devices with the detachable or attachable therapeutic hand support device 10'.

Accordingly, the step (b) of the method of playing games may further comprises a step of providing the private casino communication networking platform for remotely linking the communication network 30' with the individual electronic devices with the detachable or attachable therapeutic hand support device 10' as described in the above preferred embodiments and providing a game interface for the players to interact with games and other registered players of the networking system 20'. It is worth to mention that the central control 40' may further electrically link to any other facilities or service system attached to the casino, so that the players of the casino customers are able to link to the interface of the casino communication networking platform for selectively and remotely placing an order, such as ordering room services, or reserve the restaurant reservation.

Accordingly, each of the individual electronic devices with the detachable or attachable therapeutic hand support device 10' as described in the above preferred embodiments further comprises a communication key to instantly communicate to the networking system 20'. For example, the communication key can be a service request button arranged in such a manner that when the service request button is pressed, the operator of the central control 40' will be notified to provide high quality service to the player. Therefore, even the player stays at the hotel room or sits in front of the individual electronic device with the detachable or attachable therapeutic hand support device 10' in the casino, the player will get the service immediately. The communication key can also be a panic button arranged in such a manner that the operator of the central control 40 will be notified in case of emergency. For example, when other players are cheating during the game, the player is able to notify the operator immediately. Or when the players are in dangerous, such as someone breaking in his hotel room, the operator of the central control 40' will be notified immediately.

Accordingly, the step (a) of the method may further comprise a step of providing the plurality of game console in the casino as electronic devices with the detachable or attachable therapeutic hand support device 10', so that the casino is able to provide the total gaming experience to their customers through another way of enjoying therapy and playing games or gambling as mentioned above.

According to the preferred embodiment, the method of the present invention further comprises a step of providing information of the casino including the services and upcoming events such as game competition, room and restaurant reservation, casino schedule, promotion, and etc.

The present invention enables multiple ways of communication in the arrangement, which includes texting, chatting, audio, video, photos, and the like in combination or selective modes without interfering in the flow of the game, among all guests and service personnel of the facility, such as the casino and the hotel or those who mutual accepted to form a communication group. There is an external component for surrounding people not playing with the users and there is an internal component for players playing with the users in the device.

In the external component, there are (1) general and surrounding personal surrogate greeting, (2) personal profile, (3) filter profile system, (4) save match, (5) line of sight, (6) save profile, (7) on and off system of communication of any or all external components. It is important to note that, in the external component, you can only save match and save profile information of other surrounding players, and only in the internal component, the user can communicate live. In save match mode, the computer will tell you when that particular person is able to play with you and in save match mode the user can put a numerical priority pending the other player availability. It is important to note the general personal profile can be of the same nature with the personal profile or they can be totally different. In the save profile, the line of sight and general profiles will be save. To be review now or later with the save profile, one must ask permission to the general profile or the line of sight profile to play together (which is different from save match). And the pictures/photos can be real or of a fantasy in nature.

In the internal components, user will select from novice mode, knowledgeable mode, skillful mode, and expert mode. These modes select the time function for all texting, chatting, pictures, videos, and audio during game time. It is important to note the user can have his or her picture displayed or the surrogate picture in the game to represent his or he physical table location in the game. It is important to note during the game only the players will see each other's selection of communication and all the pictures of the other players in the table. Some may want only using audio while other may only want pictures and text to communicate. And, it is in this window where each other past statistical analysis because this game will be recorded and updated no matter what mode the user in, for future reference.

It is important to note when playing in the skillful mode or expert mode, players can designate the table limits over, for example, 100 dollars and when two or more players want to share each other's general profile or personal profile and still play, they must request each other's approval to change game to novice mode or knowledgeable mode this will aloud for better flow of the game.

The electronic device with the detachable or attachable therapeutic hand support device 10' as described in the above preferred embodiments of the present invention will only save players that have both accepted to be saved and, in the future, if any of those players is in the same casino, it will automatically inform the user and the save match will let the user prioritize any preference of payers.

According to the preferred embodiment, the arrangement of the present invention can be set or modified to be used and customized for a facility or establishment, such as casino, resort, hotel, business entity, amusement park, university, resort, convention center, cruise, and the like. To a casino, the game will be the gambling game, such as card game. To a business entity, the method and arrangement of the present invention can be used for playing training games or processing softwares or applications for works or projects. To an education establishment such as university, the method and arrangement of the present invention can be used for playing educational games or processing softwares or applications for homeworks, teaching projects, league projects, and etc. To an amusement park, the method and arrangement of the present invention can be used for playing introduction games or processing softwares or applications for tourist guide or conducting sightseeing tour. Person skilled in the art will find easily applying the method and arrangement with the electronic devices disclosed in the present invention to play games or process softwares and applications within a facility or establishment for specific purpose.

The electronic device with the detachable or attachable therapeutic hand support device 10' as described in the above preferred embodiments is preferred to be a portable electronic device, such as notebook, tablet, console, smart phone, PDA, AR/VR device, and the like, provided by the facility or establishment for the users to individually access respectively, wherein each of the electronic devices with the detachable or attachable therapeutic hand support device 10' comprises a plurality of different applications preloaded therein, a positioning unit such as a GPS unit and a phone connection station 11 for connecting with an identification means. According to the preferred embodiment of the present invention, the identification means is embodied as a user smart phone of the user. It is appreciated that the identification means can be any other means as described above, including but not limited to ID card, smart chip, memory card, flash drive memory, face recognition means, voice recognition means, fingerprint recognition means, and etc.

The present invention further provides a method of communicatively linking the electronic devices and the detachable or attachable therapeutic hand support device 10' as described in the above preferred embodiments, they are executed by a computing system, such as electronic computer, quantum computer, liquid computer, server, IOT (internet of things), blockchains, and etc.

It is worth mentioning that blockchains are secure by design and are an example of a distributed computing system with high Byzantine fault tolerance, wherein decentralized consensus has therefore been achieved with a blockchain. This makes blockchains potentially suitable for the recording of events, medical records, video and/or casino games, and other records management activities, such as identity management, documenting provenance, food traceability or voting. In other words, a blockchain is a continuously growing list of records, called blocks, which are linked and secured using cryptography, wherein each block typically contains a cryptographic hash of the previous block, a timestamp and transaction data.

The method of communicatively linking the electronic devices with the detachable or attachable therapeutic hand support device 10' as described in the above preferred embodiments comprises the following steps:

(1) Remotely link the electronic devices with the detachable or attachable therapeutic hand support device 10' in a closed communication network 30', wherein the electronic devices with the detachable or attachable therapeutic hand support device 10' and the closed communication network 30' are provided by the facility.

(2) Verify each user for the respective electronic device with the detachable or attachable therapeutic hand support device 10' in an authorized manner in order to activate the electronic device with the detachable or attachable therapeutic hand support device 10' by connecting a user smart phone of the user to the electronic device with the detachable or attachable therapeutic hand support device 10'.

(3) Restrict each user to remotely access the electronic device with the detachable or attachable therapeutic hand support device 10' in limited locations within an area of the facility via the GPS unit, the cell tower and/or the internet of things (TOT) technology built-in with the electronic device with the detachable or attachable therapeutic hand support device 10' and within a range of the closed communication network 30'.

(4) Connect the electronic devices with the detachable or attachable therapeutic hand support devices 10' with each other through the closed networking system 20' that allows the user to selectively communicate with each other and to selectively execute different applications preloaded in the electronic device with the detachable or attachable therapeutic hand support device 10' through the closed networking system 20 in a real time manner.

According to the preferred embodiment, the electronic device with the detachable or attachable therapeutic hand support device 10' as described in the above preferred embodiments is arranged for connecting to the user smart phone. The electronic device with the detachable or attachable therapeutic hand support device 10' can be connected to the user smart phone wirelessly or by wire. Accordingly, through the connection between the electronic device with the detachable or attachable therapeutic hand support device 10' and the user smart phone, the record of the competence is sent to the user smart phone when it is authorized by the user. According to the preferred embodiment of the present invention, the electronic device with the detachable or attachable therapeutic hand support device 10' is wirelessly connected to the user smart phone by means of "Bluetooth", "NFC", "WiFi", LTE, 4G, 5G, ECT, or the closed communication network. It is worth mentioning that when the electronic device with the detachable or attachable therapeutic hand support device 10' is connected to the user smart phone by wire, the user smart phone is also charged by the electronic device, so as to prevent the user smart phone out of battery. Alternatively, the electronic device with the detachable or attachable therapeutic hand support device 10' may also provide with a charging pad for electrical charging the user smart phone. For wireless connection, the phone connection station 11' can be a wireless connection module having a predetermined connection range, such as 10 feet, of the electronic device with the detachable or attachable therapeutic hand support device 10', wherein the user smart phone should be located within the connection range of the electronic device. When the user smart phone is out of the connection range, the electronic device will disconnect with the user smart phone.

As shown in FIG. 33, the phone connection station 11' is arranged for holding the user smart phone in position. The phone connection station 11' can be a storage cavity 111' that the user smart phone can be received therein. Once the user smart phone is stored in the storage cavity 111', the electronic device and the detachable or attachable therapeutic hand support device 10' as described in the above preferred embodiments can be connected to the user smart phone wirelessly or by wire. In one embodiment, the user smart phone is received in the storage cavity 111' of the phone connection station 11' and is connected to the electronic device via a connection cable 114' extended from the storage cavity 111'. Therefore, the user smart phone is charged by the electronic device. In other words, the connection cable 114' is connected directly to the user smart phone or a charging pad for electrical charging the user smart phone and for activating the electronic device as well as its supporting sideline program. The electronic device with the detachable or attachable therapeutic hand support device 10' may or may not disconnected and deactivated when the connection cable 114' is disconnected to the user smart phone. In the secure holding, the electronic device with the detachable or attachable therapeutic hand support device 10' will activate an alarm system that will not release the storage cavity lock to the smart phone without a correct password. In other words, the user must enter a correct password, such as preset by the user, in order to release the storage cavity smart phone from the electronic device with the detachable or attachable therapeutic hand support device 10' once the user smart phone is inserted at the storage cavity 111'. It is also important as part of the security system if any of the electric devices is moved out of the facility, the electronic device will also not release the smart phone in the storage cavity 111' even though the correct password is enter, and furthermore the dormant security system will be activated.

Accordingly, each of the electronic devices with the detachable or attachable therapeutic hand support device 10' as described in the above preferred embodiments further comprises a phone interfacing module for screen-imaging the user smart phone on the electronic device. When the electronic device with the detachable or attachable therapeutic hand support device 10' can be connected to the user smart phone, the display screen of the electronic device will interface with the user smart phone. For example, the display screen 12' of the electronic device will be synchronized to image the screen of the user smart phone, such that the information displayed on the screen of the user smart phone will be displayed on the display screen 12' of the electronic device. Even though the user smart phone is received in the storage cavity 111' of the phone connection station 11', the user is able to view the information to be displayed on the user smart phone through the display screen 12' of the electronic device or by opening a new window on the display screen 12' of the electronic device to display the synchronized image of the screen of the user smart phone without removing the user smart phone from the electronic device. It is worth mentioning that the electronic device with the detachable or attachable therapeutic hand support device 10' cannot obtain or share any personal data from the user smart phone, such that no phone data will be transferred or stored in the electronic device 10' when it is connected to the electronic device.

It is worth mentioning that the phone connection station 113' is for the user smart phone and is held at the docking station 112', wherein a terminal plug 113' is provided at the docking station 112', such that when the user smart phone is docked at the docking station 112', the terminal plug 113' is inserted into a terminal slot of the user smart phone to connect to the user smart phone to connect with the electronic device with the detachable or attachable therapeutic hand support device 10' for data transmission. Therefore, the user smart phone can be charged by the electronic device. In other words, the terminal plug 113 is connected to the user smart phone for charging the user smart phone and for activation of the sideline program. The electronic device with the detachable or attachable therapeutic hand support device 10' is disconnected and deactivated when the terminal 113' is disconnected to the user smart phone. According to the preferred embodiment of the present invention, the electronic device is embodied to be activated and to activate the sideline program by an identification card, such as a membership card, issued by the facility by inserting the identification card into a card reader slot 102' of the electronic device with the detachable or attachable therapeutic hand support device 10'.

In one embodiment, the closed communication network 30' is a private casino communication network provided by the casino, such that the electronic devices with the detachable or attachable therapeutic hand support device 10' as described in the above preferred embodiments are connected with each other through the private casino communication network 30'. The identification card can also be the casino room card, such that the electronic device with the detachable or attachable therapeutic hand support device 10' and the sideline program in the electronic device are activated by the casino room card. In addition, the electronic device with the detachable or attachable therapeutic hand support device 10' and its sideline program can also be activated by the user smart phone. The verification module 44' further comprises a verification application arranged for being downloaded to the user smart phone, such that when the verification application is executed by the user smart phone, the electronic device with the detachable or attachable therapeutic hand support device 10' and its sideline program are automatically activated. The user is able to input the user' name and hotel room number, as an example, after the verification application is executed by the user smart phone. Then, the verification module 44' will verify the user when the user smart phone is linked to the networking system 20' through the mobile communication network or private casino network. For example, the verification application will generate a verification code at the user smart phone, such that when the verification code is sent to the verification module 44' by the electronic device with a detachable or attachable therapeutic hand support device 10' through the private casino communication network for verification, the electronic device with a detachable or attachable therapeutic hand support device

10' will be automatically activated. Likewise, the user is able to input the verification code in the electronic device for activation. It is worth mentioning that since the electronic device with the detachable or attachable therapeutic hand support device 10' is connected to the user smart phone, the verification code can be directly sent by the electronic device to the verification module 44' through the private casino communication network for activation. Once the user smart phone is disconnected from the electronic device, the electronic device will be automatically deactivated and locked. Therefore, the player requires re-activation of the electronic device with the detachable or attachable therapeutic hand support device 10' by the room card, player card and/or the user smart phone, wherein it is worth mentioning that the smart phone application can have all the biometric security features like iris, facial geometry, hand-voice recognition, facial pictures, finger print, and etc.

The electronic device with the detachable or attachable therapeutic hand support device 10' as described in the above preferred embodiments further comprises a connection indicator 13' generating a connection signal for indicating a connection between the electronic device with the detachable or attachable therapeutic hand support device 10' and the user smart phone. In one embodiment, the connection indicator 13' comprises a light indicator 103', which comprises at least a LED light, and/or an audio indicator 104', which comprises at least a speaker 144, provided on the electronic device with the detachable or attachable therapeutic hand support device 10', wherein the light indicator 103' is on for generating a light signal, such as a green light, and/or the audio indicator generates an "On" sound signal, such as a beep sound through the audio indicator 104', when there is the connection between the electronic device with the detachable or attachable therapeutic hand support device 10' and the user smart phone. Therefore, the player is notified that the user smart phone is received in the storage cavity 111' of the phone connection station 11'. In other words, the connection indicator 13' will generate the notifying signal that also indicates the presence of the user smart phone in the phone connection station 11'.

It is worth mentioning that the audio indicator 104' of the electronic device with the detachable or attachable therapeutic hand support device 10' can be activated for additional notification and voice command from the facility, playing music, voice communication with the employees of the facility, other users, or sound information during the playing of the games or processing of the softwares or applications.

When the electronic device with the detachable or attachable therapeutic hand support device 10' is disconnected from the user smart phone, the light indicator will be off and the audio indicator will generate an "Off" sound signal, such as two beep sounds.

In other words, once the user smart phone is removed in the storage cavity 111' of the phone connection station 11' by unplugging the connection cable, the light indicator will be off and the audio indicator will generate the "Off" sound signal.

Softwares and/or applications of games, functions and different amenities are preloaded in the electronic device with the detachable or attachable therapeutic hand support device 10' as described in the above preferred embodiments, wherein the users are able to acquire different games, functions and services provided by the facility via the applications of amenities. In one example, the amusement park will provide the electronic device with the detachable or attachable therapeutic hand support device 10' with different applications of amenities for different entertainment attractions, rides, and other events. The user is able to selectively execute the designated application of amenities to reserve a timed ticket for the rides, such that the user is able to spend time elsewhere instead of waiting in line for the rides and events. The user is able to selectively execute the designated application of amenities to make a table reservation of a restaurant in the amusement park and even able to view the menu and to pre-order food from the restaurant in advance. Through the GPS unit, the user is able to view the map in the amusement park and the user location there within to guide the user to go from place to place. The parent user is able to track the location of child in the facility via the GPS unit. In addition, different game applications preloaded in the electronic device 10' enable the user to play the games with the electronic device with the detachable or attachable therapeutic hand support device 10', especially during the waiting time or spare time. Parental controls can be set in the electronic device with the detachable or attachable therapeutic hand support device 10' by the parent users that sets controls for the use of the electronic device with the detachable or attachable therapeutic hand support device 10' by their children.

When equipment, furniture, instruments, and the detachable or attachable therapeutic hand support device 10' as described in the above preferred embodiments or other things provided in the facility are functioned with the technology of TOT (Internet-Of-Things), the electronic devices can be preloaded with applications for interacting with and/or controlling such things.

In one embodiment, the casino provides the electronic devices with the detachable or attachable therapeutic hand support device 10' as described in the above preferred embodiments for the players or users, wherein the applications are different game applications and different applications of amenities preloaded in the electronic devices with the detachable or attachable therapeutic hand support device 10'. Each of the game applications is executed in the electronic devices with the detachable or attachable therapeutic hand support device 10' for the users playing casino games with each other or against a virtual dealer through the private casino communication network in a real time manner. Each of the applications of amenities is executed in the electronic device with the detachable or attachable therapeutic hand support device 10' for the users acquiring different services provided by the casino. For example, the user is able to selectively execute the applications of amenities to make a table reservation of a restaurant in the casino. The user is able to set the room configuration in advance, such as switching on the air conditioning system or selectively adjusting the light intensity of the room light before the user enters into the hotel room. It is worth mentioning that since the applications are preloaded in the electronic device with the detachable or attachable therapeutic hand support device 10' and cannot be deleted in the electronic device with the detachable or attachable therapeutic hand support device 10' by the user, the user cannot download various applications into the user smart phone, selected by the establishment. When the user checks out the hotel casino, the corresponding electronic device with the detachable or attachable therapeutic hand support device 10' will be returned back to the hotel casino. The user verification information will be erased in the electronic device with the detachable or attachable therapeutic hand support device 10', such as deactivated by the user smart phone and/or factory reset by the casino, the user will no longer able to control the room configuration or play the casino game by the user smart phone.

The software operation system and firmware of the electronic device with the detachable or attachable therapeutic hand support device 10' as described in the above preferred embodiments are automatically updated by the facility. In one embodiment, the casino will update the hardware and software of the electronic devices with the detachable or attachable therapeutic hand support device 10'. For example, the casino/agents/contractors of the casino will update the game applications and the applications of amenities in the electronic devices with the detachable or attachable therapeutic hand support device 10', such that any new game or new amenities will be updated for the users.

The game application can be configured by the user to set the game expense through an option setting of "playing budget". For example, the user is able set $1000 as the limitation option for playing the casino games through the electronic device with the detachable or attachable therapeutic hand support device 10'. When the user loses close the limitation, the electronic device with the detachable or attachable therapeutic hand support device 10' will notify the user, such as through the light indicator and/or audio indicator. It is an option for the user to stop playing the game when exceeding the limitation unless the limitation option is disabled by the user.

It is worth mentioning that the user may charge a predetermined amount of money to the electronic device with the detachable or attachable therapeutic hand support device 10' logged in by the user to pay the accommodation expense, game expense and other service expenses through the user smart phone, Bitcoin application, or other payment applications in the user smart phone.

As shown in FIG. 33, the electronic device with the detachable or attachable therapeutic hand support device 10' as described in the above preferred embodiments further comprises a graphical display 14' for the user to play games. The graphical display 14' comprises a LED or LCD display panel 141' foldably coupled on the electronic device 10' and the holograph/light projector 142' provided on the electronic device for a holograph or a light projection. Alternatively, the display panel 141' can also be embodied as a projector screen and the graphical display 14' further comprises an image projector 143' for projecting an image on the display panel 141'. Preferably, the image projector 143' is a 3D hologram/light projector for holograph generation on the display panel 141'.

It is worth mentioning that the display screen 12' of the electronic device with the detachable or attachable therapeutic hand support device 10' is a touch screen that the user is able to play any game on the display screen 12'. Therefore, the electronic device with the detachable or attachable therapeutic hand support device 10' will provide a holographic display when the user plays the game and/or chat with other users through the electronic device with the detachable or attachable therapeutic hand support device 10'. It is an option that the game would be projected on the display panel 141' in a 3D holographic manner so as to enhance the excitement of the game. For example, when playing a card game, the cards can be digitally displayed on both of the display screen 12' and the display panel 141'. For privacy purpose, the user is able to select the cards to be displayed on the display screen 12' only. Other displays, such as text messages, game result, and/or other users' surrogate characters, can be displayed on the display panel 141'. For example, when the user wins the card game, a message of "win" will be displayed on the display panel 141'. It is worth mentioning that the message displayed on the display panel 141' is the holography.

It is worth mentioning that the graphical display 14' of the electronic device with the detachable or attachable therapeutic hand support device 10' can also use another tough screen type display screen to substitute and provide images of the games or applications or function as control console of the electronic device with the detachable or attachable therapeutic hand support device 10'. In addition, holograph can be displayed by the image projector (holograph/light) projector 143' on its own without the user of a back surface, wherein the light projection style depends on the display panel 141'. Both types can be set to interact with the user for the control of the game, prograph or device through voice command or motion detection through the microphone 142' or the motion sensor 146' respectively and vice versa. The hologram or light projection by the image (holograph/light) projector 143' can be used for alerts and interacting too. For example, the incoming caller can be displayed on the display screen 141' and the callers callsign can be a picture, surrogate, avitar, and/or emoji that can be a light projection or a holograph projection and vice versa.

In one embodiment, referring to FIG. 33B, an augmented reality and virtual reality (AR/VR) device 9' is used as the electronic device with the detachable or attachable therapeutic hand support device 10' as described in the above preferred embodiments of the present invention, wherein the electronic device with the detachable or attachable therapeutic hand support device 10', including both display screen 12' and the control panel 141' as shown in FIG. 33, is a simulated image projected from the AR/VR device 9'. The AR/VR device 9' comprises at least a headset 911' for wearing on the head of the user with speakers 912' for the user's surround sound hearing, at least a microphone 913' for receiving voice command, audio reception, voice recognition, and etc. of the user, an augmented reality device 914' for augmenting image projection, a removal virtual reality device 915' for providing virtual reality image projection, and a motion sensing device or camera 916' for detecting motions of the users so that the user may simply operate the display screen 12' as control panel and the user's motions are detected by the motion sensing device or camera 916'.

In one embodiment, referring to FIG. 33B, the AR/VR device 9' is interacting with a gaming electronic device with the detachable or attachable therapeutic hand support device 10' and the player or user. The player can operate the display screen 12' and the display panel 141' of the gaming electronic device while interacting with the sideline program to control the game in the AR/VR device 9'. The AR/VR device 9' provides augmented reality and virtual reality supporting the game electronic device with the detachable or attachable therapeutic hand support device 10' and motion detection and reception of voice command for operation of the game electronic device with the detachable or attachable therapeutic hand support device 10'. The AR/VR device 9 supported with the sideline program also projects sidelines on the display screen 12' and/or the display panel 141' the same as in the physical gaming electronic device with the detachable or attachable therapeutic hand support device 10', wherein the user is able to command through the use of hands, fingers, pupils, head motion, voice command, and etc. The gaming electronic device with the detachable or attachable therapeutic hand support device 10', the AR/VR device 9' supported with the sideline program, and the smart device such as cellular phone, are interacting with each other according to the method and arrangement of operating multi-task interactive electronic devices of the present invention. Furthermore the electronic device with the detachable or attachable therapeutic hand support device 10' is also equipped with the sideline program and also functions to aid with posture fatigue while in use and during operations of the (AR/VR) devices.

In one embodiment, the AR/VR device 9' is activated with the same security requirements for the sideline program by the combination of the smart phone and the security system that maintains the same disable function for the security tampering system as mentioned above in accordance with the invention.

In one embodiment, the game program can be seen in the AR/RV eye/head set of the AR/VR device 9' and the functions of the game are controlled in the gaming electronic device by the sideline program or vice versa. The player can have multiple sidelines operating in the gaming electronic device with the detachable or attachable therapeutic hand support device 10' as described in the above preferred embodiments as well as in the AR/VR device 9 and vice versa. The sideline program for the gaming electronic device with a detachable or attachable therapeutic hand support device 10' and the AV/VR device 9' can both be controlled by voice command. In addition, the motion sensing camera 145' provided on the front/back side of the display panel 141' and/or the AR/VR occipital sensor motion camera 916' can provide the user a 360 degree surrounding motion view of his/her location in the augmented reality and/or virtual reality while the AV/VR device 9' and the hand support device 10' are in used.

Also, the gaming electronic device with the detachable or attachable therapeutic hand support device 10' as described in the above preferred embodiments can provide the users of the AV/VR devices 9' a surround sound, the ability for the touch screen display to be an additional interactive tool and or the hologram to operate with the input apparatus such as typing apparatus like keyboard or motion sensors 146'. The user is able to select what he or she wants on the display screen 12' and what he or she wants on the augmented reality and/or virtual reality to include alert, message, game, confreres, amenities, and etc.

In addition, the AR/VR device 9' and the detachable or attachable hand therapeutic support device 10' can provide a panic button 901' just like the gaming electronic device with a detachable or attachable therapeutic hand support device 10' as described in the above preferred embodiments. In one embodiment, the AV/RV device 9' and the detachable or attachable therapeutic hand support device 10' can be activated by the smart phone and/or the gaming electronic device with the detachable or attachable therapeutic hand support device 10' and vice versa.

In one embodiment, once after the AV/RV device 9' and or the detachable or attachable therapeutic hand support device 10' is activated, the AR/VR device 9' and or the detachable or attachable therapeutic hand support device 10' can active all other sideline programs in all other gaming electronic devices with the detachable or attachable therapeutic hand support device 10' without additional step in the sideline program security or may only operate in an one AR/VR device 9' and one therapeutic hand support device 10' to one gaming electronic device. The AR/VR device 9' and or the detachable or attachable therapeutic hand support device 10' may or may not continue to need the smart phone application authorization. The AR/VR device 9' and or the detachable or attachable hand therapeutic support device interacting with the hologram and light projection motion controls can provide the user the best entertainment of his/her life. For example, in the AR/VR device 9', the user can have the holograph/light projection in the gaming electronic device with the detachable or attachable therapeutic hand support device 10' that provides an additional magical ambience as the user is playing on the gaming electronic device with the detachable or attachable therapeutic hand support device 10' in the support of the augmented reality and with the portable gaming electronic device with the detachable or attachable therapeutic hand support device 10' or vice versa.

In another embodiment, as the panic button 901' is armed on the AR/VR device 9' and on the detachable or attachable therapeutic hand support device 10', the hologram and/or the light projection and the gaming electronic device and on the detachable or attachable therapeutic hand support device 10' are activated to better assist and to identify the location of the user to first responders. It is important to mention that the AR/VR device 9 is one set with multiple functions that the user can detach the virtual reality monitor from the head set allowing the augmented reality controls to activate in addition. The augmented reality visual functions can be turn off allowing the voice command microphone, panic button and the hearing speaker to continue interacting with the electronic device programs with the detachable or attachable therapeutic hand support device 10'.

It is worth mentioning that, through the chatting module 43', the users are able to chat with each other as a group or individually via the electronic devices with the detachable or attachable therapeutic hand support device 10' and/or the AR/VR device 9' through the closed communication network 30'. Also, the user may select his or her status as available or not, such that the user is able accept or reject any chatting request from other users.

As it is mentioned above, the information storage module 41', which is executed by the computer of the facility, embodied as casino, linked to the electronic devices with the detachable or attachable therapeutic hand support device 10' for posting a record of competence in the game for each of the users at the respective electronic device with the detachable or attachable therapeutic hand support device 10' and/or the AR/VR device 9 and for transferring the record of competence to the user smart phone. For example, the record contains winning/losing records and tax information of each of the users in response to the winning/losing records.

Each of the electronic devices with the detachable or attachable therapeutic hand support device 10' as described in the above preferred embodiments is preferred to have the panic button 101' for being activated by the user to notify the facility in case of emergency. It is worth mentioning that the facility can have authorization to open the closed communication network to release the restriction of the access of the electronic devices with the detachable or attachable therapeutic hand support device 10', such that the users are able to access the electronic devices with the detachable or attachable therapeutic hand support device 10' through any public communication network. In one embodiment, for example, when the facility is the university, it will allow the students to access the electronic devices with the detachable or attachable therapeutic hand support device 10' through the public communication to access the library, bookstore, and/or classroom information in the university. In addition, the electronic devices 10 can be sold or rent by the facility to the users.

It is worth mentioning that the electronic device with the detachable or attachable therapeutic hand support device 10' of the present invention not only serves as a portable game console or processor for the user to play game or to process software or application but also serves as a conference tablet for conference meeting in the facility. Accordingly, the information and/or keynote of the conference meeting will be automatically saved in the electronic device with the detachable or attachable therapeutic hand support device 10'. For example, the conference note will be downloaded in the electronic device with the detachable or attachable therapeutic hand support device 10'. The recorded sound and video will be downloaded in the electronic device with the detachable or attachable therapeutic hand support device 10'. The text messages, voice messages, video messages, and/or other interacting messages for people will be saved in the electronic device with the detachable or attachable therapeutic hand support device 10'. It is worth mentioning that the above information of the conference meeting can also be stored in the "Cloud" storage, such that after the electronic device with the detachable or attachable therapeutic hand support device 10' is returned back to the facility, the user is able to recall all the information by login in the "Cloud" storage.

Figure 34A:
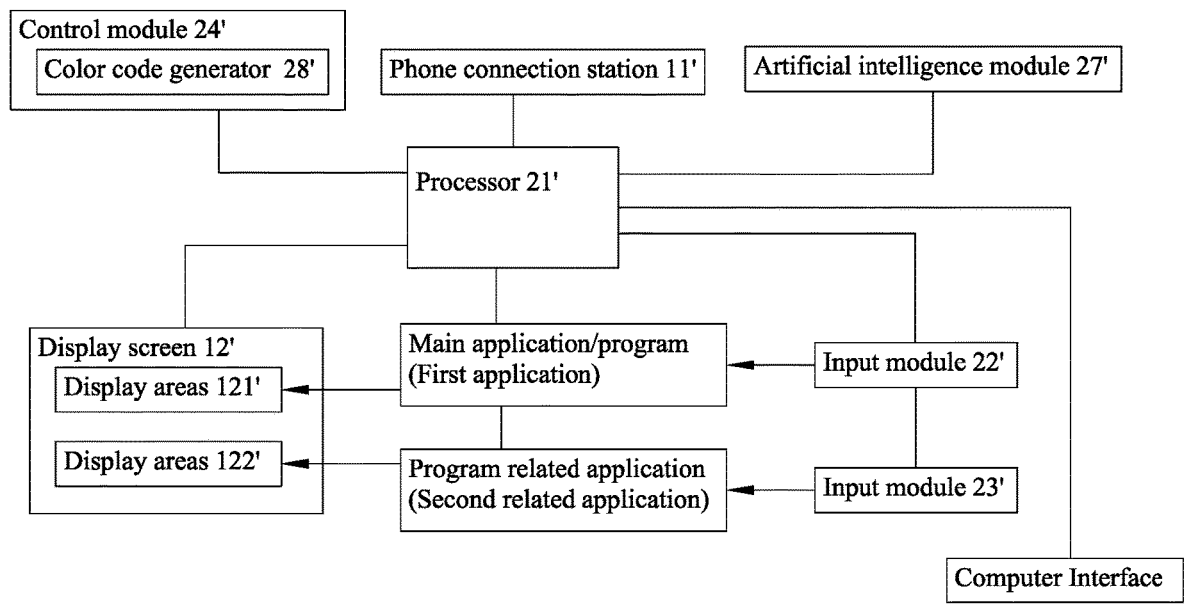
FIG. 34A is a block diagram illustrating a modification of the electronic device according to the preferred embodiment of the present invention.

FIG. 34A illustrates a modification of the electronic device with the detachable or attachable therapeutic hand support device 10' as described in the above preferred embodiments according to the preferred embodiment of the present invention, which is a device for a single touch screen or for multiple touch screen apparatus that is interactive and artificial intelligent that communicates with the operator simultaneously or independent of the games or events being run and without interfering in whatever games or events the operator selects. The electronic device and the detachable or attachable therapeutic hand support device 10' comprises one or more processors 21', one or more screen modules operatively linked to the processors 21', and two or more input modules 22', 23' operatively linked to the processors 21'. Accordingly, the one or more processors 21' are configured to execute two or more applications at the same time.

Before further disclosure of the modifications of the electronic device with the detachable or attachable therapeutic hand support device 10' as shown in FIG. 34A to FIG. 40, it is appreciated that the electronic device and the detachable or attachable therapeutic hand support device 10' as illustrated in FIGS. 34A to FIG. 40 can substitute the gaming electronic device with the detachable or attachable therapeutic hand support device 10' as shown in FIGS. 33 to 36D to equip and interact with the AR/VR device 9'. In addition, the controlling and operating of the sidelines 25' of the sideline program as described below can also be applied and operated in the electronic device with the detachable or attachable therapeutic hand support device 10' as illustrated in FIGS. 31 to 33D according to the preferred embodiment of the present invention. It is worth mentioning that the sideline(s) 25' as a tool for the process of this invention in the electronic device with the detachable or attachable therapeutic hand support device 10' in regards to the sideline program embodied in the AR/VR device 9'. In other words, what the user will observe in the AR/VR device 9' in accordance with the invention of the sidelines 25' of the sideline program, with the electronic device with the detachable or attachable therapeutic hand support device 10'. In addition, the sidelines 25' supported by the sideline program will have the same functions as in the electronic device with the detachable or attachable therapeutic hand support device 10', in the smart phone application and in the AR/VR device 9'.

Referring to FIGS. 34A to 36C, each of the one or more screen modules has two or more display areas 121', 122', dividing by one or more sidelines 25', for displaying two or more of the applications thereon respectively. Accordingly, the electronic device with the detachable or attachable therapeutic hand support device 10' as described in the above preferred embodiments comprises one or more display screens 12'. When two or more display screens 12' are used, two or more of the display areas 121', 122' are formed at each of the display screens 12'. When only one display screen 12' is used, at least two of the display areas 121', 122', dividing by one or more sidelines 25', are shared and formed at the single display screen 12'. The applications are simultaneously controlled by the input modules 22', 23' respectively, such that the applications are executed to be displayed on the display areas 121', 122' respectively and are independently controlled by the input modules 22', 23' at the same time. It is appreciated that the applications are interactively correlated with each other and are configured in one program, such that when the program is run by one of the processors 21', the applications are simultaneously executed to be displayed on the display areas 121', 122' in one of the display screens 12' respectively. In other words, when the user opens the program, the applications are simultaneously displayed on the display areas 121', 122' of the display screen 12' of the screen module. Accordingly, the input modules 22', 23' can be a keyboard, a touch pad, a set of buttons, a voice control input, a joy stick, a control console, a 3D camera module, a motion detecting input device, and etc.

According to the preferred embodiment of the present invention, the electronic device with the detachable or attachable therapeutic hand support device 10' of the present invention further comprises a control module 24' supported by the sideline program that generates at least one sideline 25' to be displayed on the display screen 12' to split or divide the display screen into two of the display areas 121', 122' on each sides of the sideline 25'. It is appreciated that the sideline 25' is a tool that the user can operate to interact and command the functions of the electronic device with the detachable or attachable therapeutic hand support device 10' (and/or the AR/VR device 9'). In other words, the sideline program with the sideline(s) 25' generated is the control system to the programs operating in the electronic device with the detachable or attachable therapeutic hand support device 10' (and/or the AR/VR device 9')

Referring to FIG. 35 of the drawings, a single quadrilateral display screen 12' is embodied that, the sideline 25' is a visual line displayed on the display screen 12' to split the display screen 12 into two different display areas 121', 122'. The sideline 25' can be, generally, a horizontal sideline or a vertical sideline to split the display screen into side-by-side display areas 121', 122' or upper-and-lower display areas 121', 122'. In particular, the sideline 25' is configured to be movable on the display screen 12 to adjust a size of each of the display areas 121', 122' correspondingly, in relation to the electronic device with the detachable or attachable therapeutic hand support device 10'.

It is worth mentioning that when two or more display screens 12' are used, each of the display screens 12' is provided with the one or more sideline 25'. In this example one to split that display screen 12' into two display areas 121', 122', such that totally four display areas 121', 122' are provided at two display screens 12'. Or, alternatively, if only one of the two display screens is provided with the sideline 25' to split that display screen 12' into two display area 121', 122' while the other display screen 12' remains to have one whole display area thereon, so that a total of three display areas will be provided at two display screens 12', as shown in FIG. 36C.

In addition, two or more sidelines 25' can also be formed on one display screen 12' to split the display screen 12' into three or more display areas 121', 122'. In other words, two or more margins can be formed on the single display screen 12' to split the display screen 12' into three or more display areas 121' in side by side and/or upper and lower manner. It is important to note that, as shown in FIGS. 35 and 36A-36D, the two display areas 121', 122' separated by the sideline 25' on one display screen 12' are configured to display the games on one of the display areas 121', 122', such as the display area 121', and the programs on the other display area 122' correspondingly. The sideline 25' separates the game programs from other non game programs.

Figure 34B:
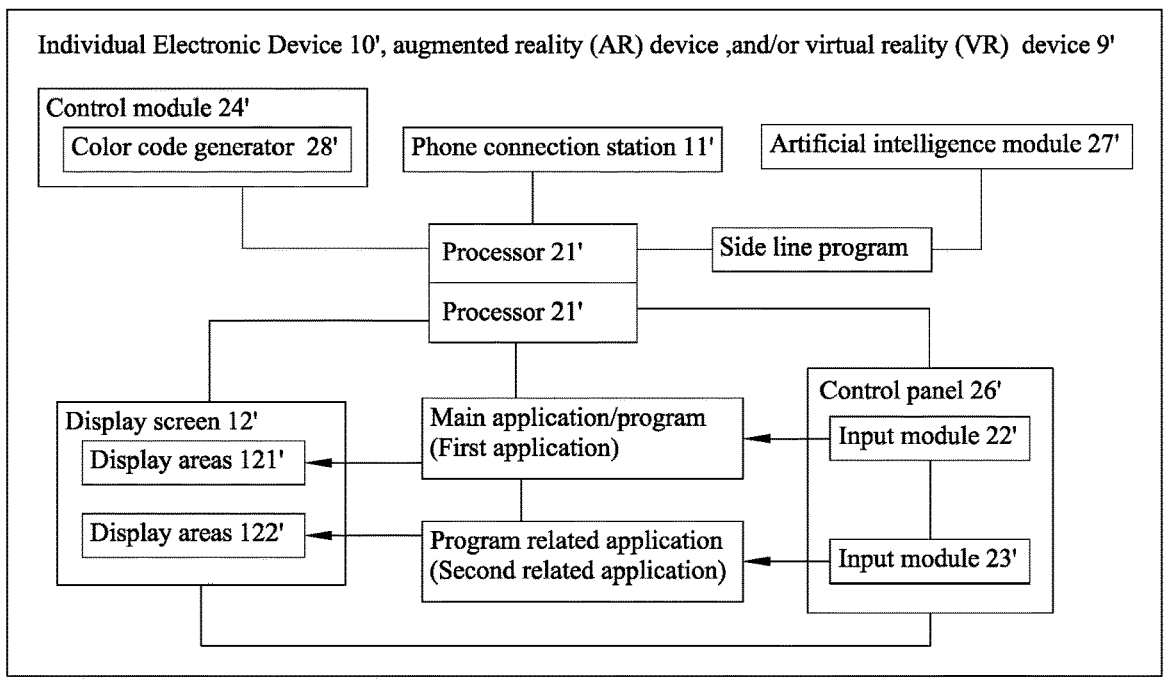
FIG. 34B is a block diagram illustrating another modification of the electronic device according to the preferred embodiment of the present invention.
Figure 34B:
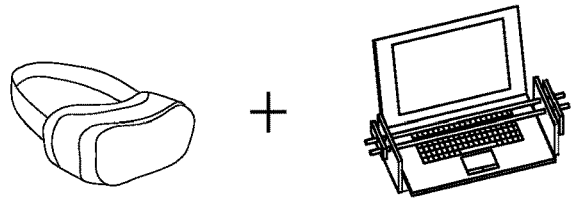

According to the preferred embodiment of the present invention, as shown in FIGS. 34A and 34B, the control module 24' further comprises a color code generator 28' that generates different color codes for the sideline 25' on the display screen 12' to indicate different program or game selections, i.e. different interactive programs, of the application. For example, the first color code generator 28' will generate the sideline in red color for the first interactive program and in blue for the second interactive program. Therefore, the user can notify which interactive program he or she has been selected via the color code of the sideline 25'. It is worth mentioning that the color codes can be set by the user via a setting configuration of the control module 24'.

In one embodiment, the electronic device with the detachable or attachable therapeutic hand support device 10' of the present invention is configured as a tablet computerized device to have a single display screen 12', such as a touch screen, as shown in FIG. 35. Accordingly, the sideline 25' is a vertical sideline displayed on the touch screen 12' to split the touch screen 12' into two display areas 121', 122'. Two different applications are executed and displayed on the display areas 121', 122'. At the same time, two input modules 22', 23' are displayed and integrally formed with the touch screen at the display areas 121', 122'. The two input modules 22', 23' can be the same or different depending the control of the application. For example, when the application is a game application, the input module 22' can be configured as a touch pad displayed and formed on the display area 121' of the touch screen. When the application is a chatting application, the input module 23' can be a keyboard displayed and formed on another display area 122' of the touch screen. The user can simply maintain a finger touching on the sideline 25' and move leftwards or rightwards, the sideline 25' is able to be moved to the right or left on the touch screen 12' to adjust the sizes of the display areas 121', 122' correspondingly in respective to the movement of the finger simultaneously. For example, when the sideline 25' is moved to the left, the left side display area 121' becomes smaller while the right side display area 122' becomes larger, vice versa.

According to the preferred embodiment of the present invention, the applications running on the display areas 121', 122' respectively are configured to be operated via the input modules 22', 23' at the same time. For example, the user is able to play the game via the game application via the touch pad of the input module 22' by one hand and to chat with other user via the keyboard of the input module 23' by the other hand, such that the user does not have to switch between the applications to display on the display screen 12' or between windows opened on the display screen 12' to show on top of the other windows for operation.

Person skilled in the art would appreciate that tablet type electronic device as shown in FIG. 35 would be a simulated electronic device projected from an AR/VR device 9' as shown in FIG. 33A. Or, alternatively, the tablet type electronic device with the detachable or attachable therapeutic hand support device 10' as described in the above preferred embodiments as shown in FIG. 35 would be interacted with an AR/VR device 9' as described above.

It is worth mentioning that, to the conventional computer, the user may merely operate one application at a time. For example, the user has to click on the icon shown on the control bar to open that window and then click on that window to activate that window so as to operate the application in that window. Or, the user may open two or more windows to show on the screen with different size at the same time, but the user must first click on the window selected in order to put that window on top of other windows and then click on that front window again to activate that front window so as to operate that activated window. However, according to the preferred embodiment of the present invention, as shown in FIGS. 35 and 36A-36D, the user may use both hands to operate the two or more applications on the two or more display areas 121', 122' independently and simultaneously at the same time. When more than one input devices are provided with the electronic device with the detachable or attachable therapeutic hand support device 10' as described in the above preferred embodiments, such as keyboard, touch pad, voice input device such as microphone 142', and the like, each of the display areas 121', 122' will provide an input device selection bar thereon with icons of different input devices, so that the user may simply select the desired input device for operating the application running in that display area 121', 122' and make changes of the desired input device anytime. Accordingly, for example, the user may use the touch pad to operate the game running on one of the display area 121', and use the microphone 142' and speaker 144' to operate the chatting application running on the other display area 122'.

In one embodiment, referring to FIG. 34B, the electronic device with the detachable or attachable therapeutic hand support device 10' as described in the above preferred embodiments further comprises a control panel 26' foldable coupled at the display screen 12' to form a laptop-like or notebook type computerized electronic device as shown in FIGS. 36A to 36C, wherein the electronic device illustrated by schematic drawings that merely shows the overall shape of the display the screen 12' and control panel 26' without illustrating the detail equipped elements such as storage cavity 111', microphone 142', speaker 144' and so on, as shown in FIG. 33.

Referring to FIGS. 36A to 36C, the input modules 22', 23' are provided at the control panel 26' to independently control the applications displayed on the display areas 121', 122' of the display screen 12'. Accordingly, the display screen 12' can be a touch display screen or a non-touch display screen. There are two or more sidelines 25' generated on the display screen 12' and the control panel 26' respectively. The sideline 25' formed at the display screen 12' is a visual sideline to separate the applications displayed on the display areas 121', 122' respectively while the sideline 25' formed at the control panel 26' is a control sideline to separate the input modules 22', 23' thereon.

It is noted that the control panel 26' can also be a touch screen and the two input modules 22', 23' are two display areas shown on the touch screen separated by the control sideline 25' on the control panel 26' too. Accordingly, the input devices such as keyboard, input apparatus such as typing apparatus like keyboard, touch pad or virtual images shown on the touch screen type control panel 26' as the input modules 22', 23'.

Preferably, one of the input modules 22' is automatically or manually selected to match with one of the applications correspondingly, such as game application, and one of the input modules 23' is manually selected by the user to match with other applications.

In one example, the notebook type, tablet type or AR/VR type electronic device with a detachable or attachable therapeutic hand support device 10' as described in the above preferred embodiments is embodied as a portable game device for the user (player) to play games. The portable game device with a detachable or attachable therapeutic hand support device 10' as described in the above preferred embodiments for the entertainment industry can provide program functions through the sidelines 25', wherein the sidelines 25' is in conjunction and independent to the games or events that the user (operator) is participating to enhance the entertainment experience. In addition, game developers will have the total autonomy to include additional functions in their games or by just utilizing the existing program functions in the sidelines 25'. In particular, the applications include at least a first application, for example a game application, and at least a second related application, for example a game related application. The game related application comprises different sideline programs. It is important that additional functions do not interfere with the sidelines programs because the programs functions in the sidelines 25 are independent of the games or the events being watch or play. It is important to understand the sideline programs are constantly running independent of the games or events running in the display areas 121', 122' of the display screen 12'. The sidelines programs are fully operational when wagging or in used in an authorize event. It is also important to understand there is a symbiotic relation between all the sideline commands and the game display area 121' of the display screen 12' to provide a smooth flow of the games being played and of the events being watched. For example, the game/event display area 121, 122' will minimax or enlarge base on the operator sideline positioning. The user can also select multiple games/events viewings being controlled by the program. The types of games played in the game display area 121' or 122' may have unlimited futuristic capacities but they need to be approved by the establishment or facility like casino, theme park and etc., and the same is true for events being watched that they need to be approved by the establishment or facility. For examples, games like e-sport, ninja fruit and events like live sport bets, concerts and etc. The program is especially important when being utilized in a localize settings that, no matter if it is an hour event or a 4 years event, it is made for the communication of guest and the participation and enjoyment of the amenities in that establishment or facility.

Referring to FIGS. 36A to 36C, there are two sidelines 25' provided for every game, application or event, wherein one of the sidelines 25' is the visual sideline provided on the display screen 12' to divide it into the two display areas 121', 122' to display the game, application or event on the left display area 121' and the function program on the right display area 122', and the other sideline 25' is the control sideline provided on the control panel 26' to divide it into the two input modules 22', 23' for operating the game or event and the function program of the two display area 121', 122' respectively at the same time.

It is worth mentioning that the applications of the game or event and the function program displayed on the two display areas 121', 122' of the display screen 12' can be ran by the same processor 21' of the electronic device with the detachable or attachable therapeutic hand support device 10' or by more than one processors 21' of the electronic device on the detachable or attachable therapeutic hand support devices 10' independently while at least one of the two processors 21' is configured to operate the positioning of the sidelines 25' in responsive to the operation and selection of the positions of the sidelines 25 as mentioned above. Of course, the applications can also be ran and controlled by the server computer of the facility with the detachable or attachable hand therapeutic support device, and one or more processors 21' of the electronic device with the detachable or attachable therapeutic hand support device 10' is merely provided for communication, setting, computation, operating and controlling the control panel 26', data transmission between the electronic device with the detachable or attachable therapeutic hand support device 10' and the server computer of the facility via the networking system 20', and so on.

Both sidelines 25', i.e. the visual and control sidelines, are configured to be able to be moved such as by rolling up, down, right, or left for the users' choices according to their own personal selection. Both sidelines 25' (visual/control) can be configured and preset wide, narrow, short, or enlarge as well as provided with label words and audible. Both sidelines 25', including the visual and the control sidelines, can be in any setting independent of each other and will continue providing the programmable functions in each corresponding sidelines programmable function, without interfering with the flow of the game or with the less distraction to the game. The program symbiotic relation between the sideline and the game screen on the respective display area 121', 122' will automatically give player the biggest game screen viewing field (at all times) base on the user's selection of size of the sideline 25'.

Both sidelines 25', including the visual and the control sidelines, are configured to have interactive and artificial intelligence. The interactive sideline is color code, with or without audio effect from the speaker 142', to alert you to the most resent activated program. For example, the players have three program functions in the visual sideline (1) profiles, (2) alerts and (3) promotions. The player may select red for profiles, green for alerts and blue for promotions, so that as the player is playing, the program profile is activate inside the sideline 25' flashing red and the sideline 25' itself is also flashing red to indicate that the profile program has a match for the player to see the color code and/or to hear the audio effect. The same is provided for the control sideline too. For example, if the player has already seen a profile and has been communicating in the past and, while he is playing, the control sideline 25' turns red to indicate the resent text, voice, video or audio message a match profile has been send to the player.

It is also important to note that the inside to the sidelines 25' can also all be illuminated red in the same example. The interactive sidelines are program functions that do not change even if you change games or watching different events, unless the user edits his or her filter sideline settings to have different results generated by the programs. For example, editing different profiles functions will generate different profile matches. Also, editing a different service functions will generate different food selections, and etc. The same is true for all other program functions, or as many other program functions as the player selected in the sidelines 25'. It is also important to understand the programs can be edit as a onetime change or as a permanent change.

The other interactive function of the sidelines is the audio program for all the programs in the sidelines 25' and not in the game display area of the display screen 12' or control screen of the control panel 26'. The way it works is that, as the programs are working, the operator can select any or all programs on or off to be heard as they come on. For example, the user will see a profile color code message on screen in the visual sideline 25' at the same time the operator will hear it. The operator has the control to hear it louder than the games or events on both ears or on the right or left ear or softer (likewise). The same is true for the control sidelines programs. The operator will also be able to hear the message he or she are sending out or to read the messages shown in the display areas 121', 122'.

According to the preferred embodiment of the present invention, the electronic device with the detachable or attachable therapeutic hand support device 10' as described in the above preferred embodiments of the present invention further comprises an artificial intelligence module 27' running by at least one of the one or more processors 21' as an intelligent user assistant for assisting the user to operate the sideline program, the first application and the second related application such as player ranking alerts, promotions, browsers, and other services. The artificial intelligence in the sideline 25' is the program that remembers your choices, likes and dislikes, and activities in the sideline programs, to include pass profile matches. Therefore, if next time you come and a match user was saved from last visit of the sideline programs will notify you and assist you with a record (text, video, or audio) of pass communication to remind the user (operator) and better assist you in communications. It may also remind you of food selection, activities and etc. It is also important to note that an operator may set the interactive and artificial intelligence module 27' to run automatically or off. The automatic setting saves everything and follows the user's pass choices if there is any history of past activity or learns from the user's current actions for the future. Also, in the automatic settings, the program of the visual sideline 25' will active the control sideline programs into a symbiotic force reaction to incoming information and will automatically provide the tools to answer in the control sideline 25' and minimax or enlarge the game/event display area of the display screen 12'. In the manual setting, users must select from novice, skillful, expert or master, and this will enable the operator adequate time.

It is appreciated that the user is always in control of both sidelines 25'. The sidelines 25' are configured as a function of the program and so are the game being played or events being watched. The user can choice to add another game and play two games at the same time. He or she can determine the presentation of the games by moving the sidelines 25' and, furthermore, the user can select what game is displayed on top, bottom, right or left, up to twelve games. In other words, users can play up to six games at one time and continue using the program functions provided by the sidelines 25'. The user accomplishes this task by dragging the games and events through the color coded sideline 25' from the browser inside the sideline 25'. It is important to know that no matter the size of the sidelines 25', the user selects the program will automatically set the game screen of the display screen 12' and the control screen of the control panel 26' to the largest possible size. The user can set fix locations of the sidelines 25' to fix size to permanently expose all the program functions of the sideline 25' that he or she wishes to see, while at the same time the program maximizing the game/event screen size at all times.

This is not a picture in picture function to the main screen while this is a complex communicating interactive and artificial intelligence program, that enhances the games, program events, communications, and the entertainment of the events. The control sideline 25', when manually widen, reveals a (1) keyboard, (2) emojis, (3) panic bottom, and (4) control settings. The control sideline 25' that can also be fix to size to permanently expose the keyboard and other controls in the control sideline 25', while at the same time maximizing the control screen size of the control panel 26'.

The program functions are in the sidelines 25' and these are the tools the device communicates with the players or users, with or without the less interference to the game screen of the display screen 12'. The player or user has the control of which functions he or she wants to use on/off if any or all. For example, some functions in the visual sideline 25' are (1) ranking of players, (2) alerts, (3) promotions, (4) brows game/pop ups and (5) services. Once again, these programs functions have artificial intelligence. In other words, the electronic device with the detachable or attachable therapeutic hand support device 10' remembers and selects from past activities but will also remember both sidelines settings, so that the more the user plays or uses, the better the program works for the user. In these programs, the filter controls can also be changed by the players or users to get different selection options from the electronic device with the detachable or attachable therapeutic hand support device 10' as a one-time selection or as a permanent option.

Person skilled in the art would appreciate that tablet type electronic device with the detachable or attachable therapeutic hand support device 10' as described in the above preferred embodiments as shown in FIGS. 36A to 36C would be an simulated electronic device projected from an AR/VR device 9' as shown in FIG. 33. Or, alternatively, the electronic device with the detachable or attachable therapeutic hand support device 10' as shown in FIGS. 36A to 36C would be interacted with an AR/VR device 9 to control and operate the games, programs and functions as described above. For example, the user can wear the AR/VR device 9' with the headset 911', receive sound from the speakers 912', give voice commands to control and operate the electronic device as well as the sidelines 25' through the microphone 913', have augmented reality and/or virtual reality supported for the display screen 12' and the control panel 26' of the electronic device with the detachable or attachable therapeutic hand support device 10' from the AR device 914 and VR device 915', and/or give motion commands to control and operate the electronic device with the detachable or attachable therapeutic hand support device 10' as well as the sidelines 25' through by detecting motions of the user through the motion sensing device or camera 916'.

It is worth mentioning that the sideline 25' may have two different computer languages operating on opposite sides of the sideline 25'. For example, a computer programmer may select a game engine based on best graphics while another computer programmer may select a different computer language based on the program flexibility. It is appreciated that the sideline program controls are ergonomic human motions optimizing the most speed with the less effort conserving energy for prolong utilization. For example, touch point commands can be demanding in prolong repetition and are seriously near to impossible with muscular, and neurological tremer. It is important to mention that the sideline program is also voice commandable and user friendly. Programmable sideline controls the display of selected pop-ups programs and their location like incoming programs, communications, visual and voice alerts, with the less effort to the user and with the artificial intelligence that the more the user plays, the better the sideline program works for the user.

The ranking of player is a combination of programs that will provide multiple players a communication tool for the games/events that do not have a communication tools platform and will provide additional communication options to the game that have communication tools. In this arrangement, the electronic device with the detachable or attachable therapeutic hand support device 10' will save match of these profiles for you to rank while in a game/event.

The first tool is a (1) filter survey for player and the other facility guest. In other words, likes, dislikes and personality. (2) The other is a brief surrogate clip video, text, photos, audio, or any combination. (3) The next tool is a general video. (4) The next is a line of sight video this is when the electronic device with the detachable or attachable therapeutic hand support device 10' has physically been targeted because someone wants to contact you. In all these options, the electronic device with the detachable or attachable therapeutic hand support device 10' can save, delete and rank the other users after the main user has viewing the profiles. This will provide the electronic device with the detachable or attachable therapeutic hand support device 10' the ability to assist the user with communications. The program will assist the user to communicate with the user's selected users as they become available in the ranked order the user provided.

Alerts will be set by the user's choice of phone numbers and emails the user wants to take. Emergency notice will be posted to override the game and the nature of the emergency. Promotions will have selected algorithms to generated gifts, coupons, and discounts to better reward the user and will also include advertisement. Services will range from booking restaurant, room services, operator, security, waiter, scheduling theme rides, GPS maps, event tickets, and etc.

In one example, the user is verified for the electronic device with the detachable or attachable therapeutic hand support device 10' in an authorized manner via the verification code to use the electronic device with the detachable or attachable therapeutic hand support device 10' as a portable game device within the private communication network, such as private casino communication network. The game application and the game related application are preloaded in the portable game device with the detachable or attachable therapeutic hand support device 10'. Alternatively, the game application and the game related application are saved in a cloud storage that the game application and the game related application can be loaded in the portable game device with the detachable or attachable therapeutic hand support device 10' through Internet or Intranet. For example, once the portable game device with the detachable or attachable therapeutic hand support device 10' is wirelessly connected to the communication network, the game application and the game related application will be automatically loaded in the portable game device through the communication network.

It is worth mentioning that the user is able to download the game application and the game related application to his or her personal electronic device, such as a notebook, a tablet, a smart phone, or an AR/VR device, as the portable game device with the detachable or attachable therapeutic hand support device 10', and connect the personal electronic device to the communication network in order to play. The game application and the game related application are downloaded to the personal electronic device with the detachable or attachable therapeutic hand support device 10' and its screen is functioned as the display screen 12' and configured by the downloaded program to form the display areas 121', 122' by forming the visual sideline 25' in the display screen 12', wherein the game application and the game related application are displayed in the two display areas 121', 122' respectively. In addition, the keyboard or mouse pad can be used as the first input module 22' to control and operate the game application displayed on the display area 121', and the microphone 142' or another mouse connected thereto can be used the second input module 23' to control and operate the game related application displayed on the display area 122' at the same time.

Likewise, another personal electronic device can be wirelessly linked to the communication network by the electronic device with the detachable or attachable therapeutic hand support device 10' of the present invention in order to play game, such that the electronic device with the detachable or attachable therapeutic hand support device 10' of the present invention forms a communication link between the personal electronic device and the communication network.

In view of the electronic device with the detachable or attachable therapeutic hand support device 10' as described in the above preferred embodiments according to the preferred embodiment of the present invention, as shown in FIGS. 36A-36C, when the game application is loaded and displayed at the display area 121' of the display screen 12', the game related application is automatically loaded and displayed at the other display area 122' of the display screen 12'. The first input module 22' will be automatically loaded at the control panel 26'. For example, when the user selects to play the "Blackjack" electronic card game, a set of touch buttons are automatically configured at the first input module 22 of the control panel 26' for the user to select the betting amount, card drawing/holding selections, and etc. At the same time, the user is able to select one of the sideline programs of the game related application, such as chatting platform, intelligent user assistant, ranking, user profile, and etc. When the chatting platform is selected, the virtual keyboard as the second input module 23' will be automatically selected and displayed on the control panel 26'. Therefore, the user is able to control (play) the electronic card game via the first input module 22' and to chat with other player users via the second input module 23' at the same time. It is worth mentioning that the user is able to select different input modules 23', such as voice input, keyboard, motion detecting input, mouse input, touch pad, touch screen input, holograph control activation, and etc., for the game related application. In addition, other player users who play the same game will be automatically shown in the chatting platform, such to that the user is able to chat with other player users at the same time when he or she plays the game.

Accordingly, the phone connection station 11' is adapted for connecting with the user smart phone. The player verification module 44' comprises a verification program application to generate a verification code in order to activate the electronic device with the detachable or attachable therapeutic hand support device 10' and also to execute the user smart phone settings and preferences downloading to the electronic device with the detachable or attachable therapeutic hand support device 10' automatically. In other words, the smart phone program applications is a set up version for the continue continuity of use on to the portable electronic devices with the detachable or attachable therapeutic hand support device 10', for the user to use with and without the portable electronic device with the detachable or attachable therapeutic hand support device 10'.

As shown in FIG. 36A, the display screen 12' is split by the visual sideline 25' into the two display areas 121', 122', such as left display area and right display area. The game application, such as an electronic tic-tac-toe game, is selected and executed on one of the display areas 121', 122', for example the left display area 121'. The related game application, including different program selections such as profile, alert, promotions, and browsing, is displayed on the other display areas, i.e. the right display area 122', for the user to select. At the same time, the first input module 22' is automatically loaded as a set of directional buttons and selection buttons on the control panel 26' and the second input module 23' is automatically loaded as a virtual keyboard on the control panel 26'. It is worth mentioning that the first and second modules 22', 23' are separated by the control sideline 25' on the touch screen type control panel 26'. Therefore, the user is able to play the game via the first input module 22' by the left hand of the user and to select one of the program selections via the second input module 23' by the right hand of the user at the same time. The electronic device with the detachable or attachable therapeutic hand support device 10' is configured to enable user to select the positions of the first input module 22' and the second input module 23' that the user is convenient to control and operate the game application and the game related application displayed on the left and right display areas 121', 122' of the display screen 12' respectively at the same time. For example, if the game application is displayed on the left display area 121', it may be more convenient to set the first input module 22' configured to control and operate the game application on the left side of the control panel 26' too while the second input module 23' is set to position on the right side of the control panel 26' to control and operate the game related application displayed on the right display area 122' of the display screen 12'. Of course, it is free for the user to configure according to his or her convenient and desire.

As shown in FIG. 36B, an alternative mode of the above preferred embodiment of the present invention is illustrated, wherein the display screen 12' is embodied as the bottom touch screen panel and the control panel 26' is embodied as the upper touch screen panel. Person skilled in the art may already understand that the positions of the display areas 121', 122' and the input modules 22', 23' are preferably configured to be interchangeable or set according to the desire of the user, especially when both the display screen 12' and the control panel 26' are touch screen panels. Some users may prefer to have the game application and its input module 22' displayed on, for example, the bottom touch screen panel and the game related application and its input module 23' displayed on, for example, the upper touch screen panel of the electronic device with the detachable or attachable therapeutic hand support device 10'. In other words, the electronic device with the detachable or attachable therapeutic hand support device 10' is preferably programmed to be capable of interchanging the positions of the applications and their input modules on the screen panels anytime by setting and configuring them.

FIG. 36C illustrates another alternative mode of the above preferred embodiment of the present invention, wherein the display screen 12' is divided into three display areas 121', 122', 123' by a vertical virtual sideline and a horizontal virtual sideline, while the control panel 26' is divided into three input modules 22', 23', 24' by a vertical control sideline and a horizontal control sideline 25' accordingly to control and operate a total of three applications displayed on the three display areas 121', 122', 123' respectively at the same time. As mentioned above, the sidelines 25' are all configured to be movable by such as rolling upwards, downwards, leftwards, or rightwards to adjust the relative sizes of the display areas 121', 122', 123' and the input modules 22', 23', 24' anytime. In other words, the electronic device with the detachable or attachable therapeutic hand support device 10' according to the preferred embodiment of the present invention enables the user to select the number of display areas provided on the display screen 12' and input modules provided on the control panel 26' by selecting the number and positions of the virtual sidelines 25' configured on the display screen 12' and the control sidelines 25' configured on the control panel 26'.

It is worth to further mention that the surrounding rims of the frame of the display screen 12' and the control panel 26' can also be made to form illuminating rims so as to provide lighting effect of different colors as well as flashing with respect to the game(s) playing with the electronic device with the detachable or attachable therapeutic hand support device 10' to enhance the game effect, indication and entertainment experience. Also, the sound effect from the speaker, the incoming alerts, the sideline programs and the panic button may be corresponding to the lighting effect to strengthen the indication of "ON" status of the electronic device with the detachable or attachable therapeutic hand support device 10' for enhancing entertainment experience.

Figure 37:
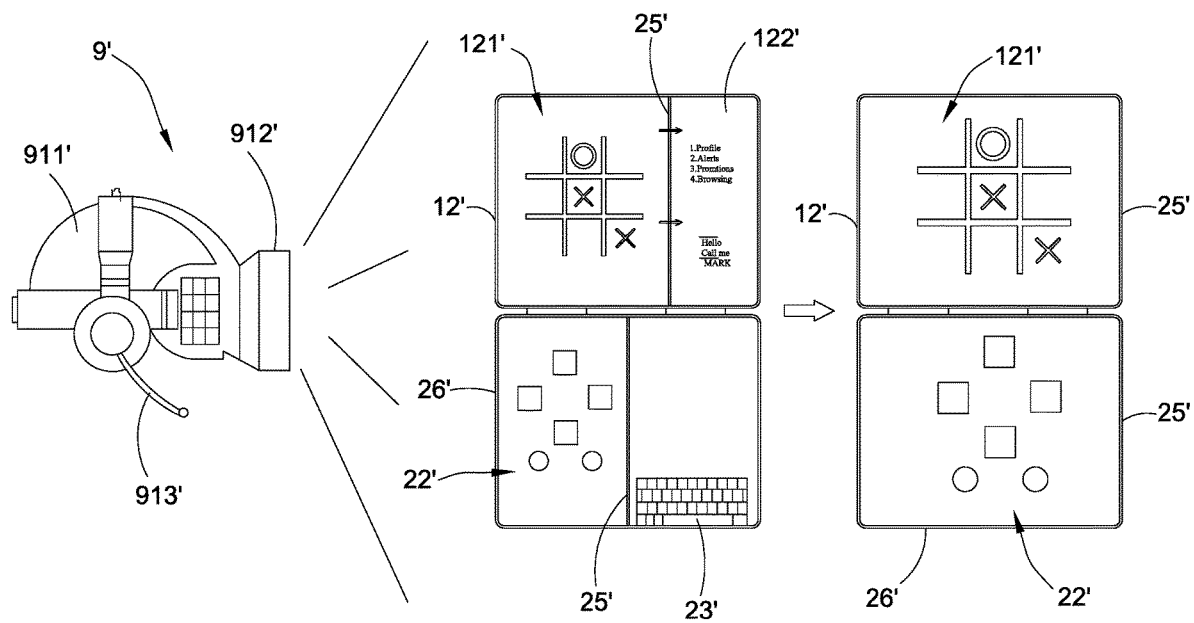
FIG. 37 illustrates the size adjustment of each of the display areas via the movement of the sideline according to the preferred embodiment of the present invention.

As described above, the user is able to move the visual sideline 25' to adjust the size of each of the display areas 121', 122'. In particular, the user is able to preset that when the visual sideline 25' is moved, the control sideline 25' will be moved correspondingly. Referring to FIG. 37, for example, when the visual sideline 25' is moved to the right direction, the control sideline 25' can be preset to be moved correspondingly to the right direction too. Preferably, when the visual sideline 25' is moved to the one boundary edge of the display screen 12', the corresponding display area 121', 122' will be minimized. For example, when the visual sideline 25' is moved to the right boundary edge of the display screen 12', the right display area 122' will be disappeared, such that only the game application will be displayed on the display screen 12'. Correspondingly, the second input module 23' will be closed at the same time.

Figure 38B:
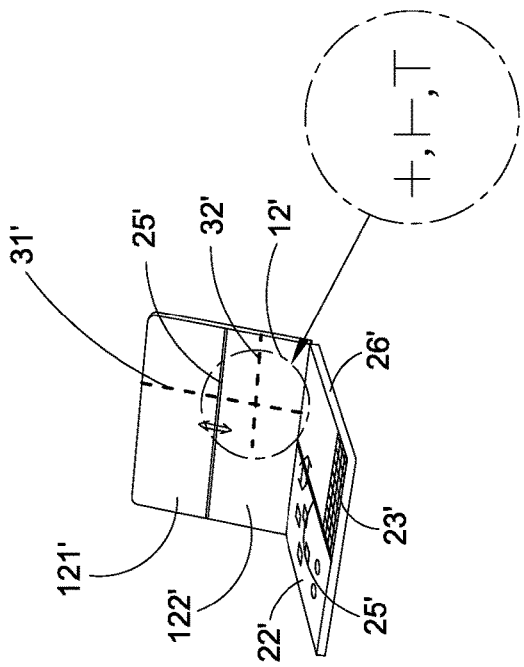
FIGS. 38A to 38C illustrate different sideline configurations of the electronic device and how to reset or reposition the sidelines of the electronic device according to the preferred embodiment of the present invention.
Figure 38C:
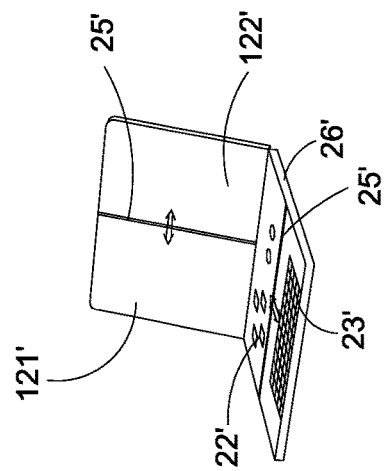
Figure 38A:
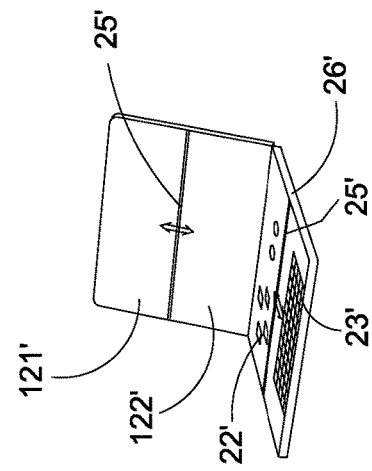

In addition, the visual and control sidelines 25' can be selectively configured by the user as shown in FIGS. 38A to 38C to either form as a vertical sideline or horizontal sideline. Referring to FIG. 38A, the virtual sideline 25' is set to be a horizontal sideline on the display screen 12' to divide into an upper display area 121' and a lower display area 122' while the control sideline 25' is also set to be a horizontal sideline on the control panel 26' that divides the control panel into an upper input module 22' and a lower input module 23', wherein the user may select and set one of the upper and lower input modules 22', 23', for example the upper input module 22', to control and operate the upper display area 121' and the other input module, for example the lower input module 23' controls and operates the other display area 122', vice versus.

FIGS. 38B and 38C illustrate the virtual and control sidelines 25' can also be configured and set in opposite manner, wherein the electronic device with the detachable or attachable therapeutic hand support device 10' is illustrated by schematic drawings that merely shows the overall shape of the display screen 12' and control panel 26' without illustrating the detail equipped elements such as storage cavity 111', microphone 142', speaker 144' and so on as shown in FIG. 33.

As shown in FIG. 38B, the virtual sideline 25' on the display screen 12' is set as a horizontal sideline to divide the display screen 12' into an upper display area 121' and a lower display area 122', and the control sideline 25' of the control panel 26' is set a vertical sideline to form a left input module 22' and a right input module 23' on the control panel 26'. The user may select one of the left and right input modules 22', 23', for example the left input module 22' to control and operate the upper display area 121' while the other input module, for example the right input module 23' to control and operate the lower display area, vice versus. As shown in FIG. 38C, the virtual sideline 25' on the display screen 12' is set as a vertical sideline to divide the display screen 12' into a left display area 121' and a right display area 122', and the control sideline 25' of the control panel 26' is set a horizontal sideline to form an upper input module 22' and a lower input module 23' on the control panel 26'. The user may select one of the upper and lower input modules 22', 23', for example the upper input module 22' to control and operate the left display area 121' while the other input module, for example the lower input module 23' to control and operate the right display area, vice versus.

According to the preferred embodiment of the present invention, in order to resetting or repositioning of the sideline 25' parallelly, as show in FIG. 39A, the user may simply use his or her finger, for example, double clicking or touching and holding for a predetermined period of time on any of the sideline 25' to activate that sideline 25' to movable status, and then the user may use a finger to touch and hold that sideline 25' to slide to the desired position. When the user removes his or her finger from that sideline 25' at the new position, after a predetermined period of time, such as three seconds, that sideline 25' will stay at that new position. Similarly, when the control panel 26' is a touch screen, the parallel resetting or repositioning the sideline 25' separating the input modules 22', 23' on the control panel 26' can also be changed or reset by the above "T" setting method too.

To reset or change the orientation of the sideline 25', such as from a horizontal sideline to a vertical sideline or from a vertical sideline to a horizontal sideline, there are multiple ways being able to program. For example, the change of the orientation of any desired spot of the sidelines 25' can be done by a "T" setting method, wherein referring to FIGS. 39B and 39C, the user may simply use his or her finger, for example, to draw a first setting line 31' from the sideline 25' and generally perpendicular to the sideline 25', and then draw second setting line 32' across the first setting line 31' and generally parallel to the sideline 25' to form a "T" setting FIG. 40A. After a certain period of time, the original sideline 25' disappears and a new sideline 25' is formed to substitute the original sideline 25' at the position of the first setting line 31' and the "T" setting FIG. 30 disappears too. Therefore, the orientation of the sideline 25' changes perpendicularly.

For example, a horizontal sideline 25' is reset and changed to a vertical sideline 25' as shown in FIG. 39B, wherein the first application and second related application displayed on the upper and lower display areas 121', 122' originally will be displayed on the left and right display areas 121', 122' separated by the new vertical sideline 25', if the default setting is preset to upper-to-left and lower-to-right format, or alternatively, upper-right and lower-left format. Or, a vertical sideline 25' is reset and changed to a horizontal sideline 25', as shown in FIG. 39C, wherein the first application and second related application displayed on the left and right display areas 121', 122' originally will be displayed on the upper and lower display areas 121', 122' separated by the new horizontal sideline 25', if the default setting is preset to left-to-upper and right-to-lower format by the user in the electronic device with the detachable or attachable therapeutic hand support device 10'. Of course, alternatively, the default setting preset to right-to-upper and left-to-lower format by the user. Similarly, when the control panel 26' is a touch screen, the orientation change of the sideline 25' separating the input modules 22', 23' on the control panel 26' can also be changed or reset by the above "T" setting method too.

FIGS. 39A to 39C illustrate that the electronic device with the detachable or attachable therapeutic hand support device 10' as shown in FIGS. 38A to 38C can also be interacting with the AR/VR device 9' as shown in FIG. 33A, wherein the user can wear the AR/VR device 9' with the headset 911', receive sound from the speakers 912', give voice commands to control and operate the electronic device with the detachable or attachable therapeutic hand support device 10' as well as the sidelines 25' through the microphone 913', have augmented reality and/or virtual reality supported for the display screen 12' and the control panel 26' of the electronic device with the detachable or attachable therapeutic hand support device 10' from the AR device 914' and VR device 915', and/or give motion commands to control and operate the electronic device with the detachable or attachable therapeutic hand support device 10' as well as the sidelines 25' through by detecting motions of the user through the motion sensing device or camera 916'.

Figure 41:
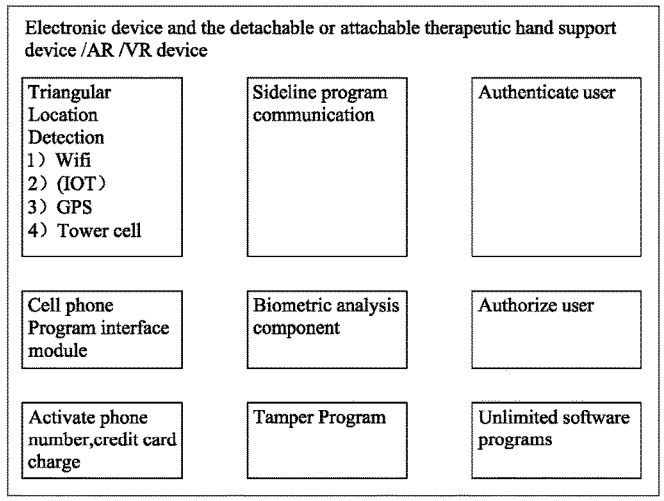
FIG. 41 is a block diagram illustrating the interacting of the electronic device and the AR/VR device according to the preferred embodiment of the present invention.
Figure 42:
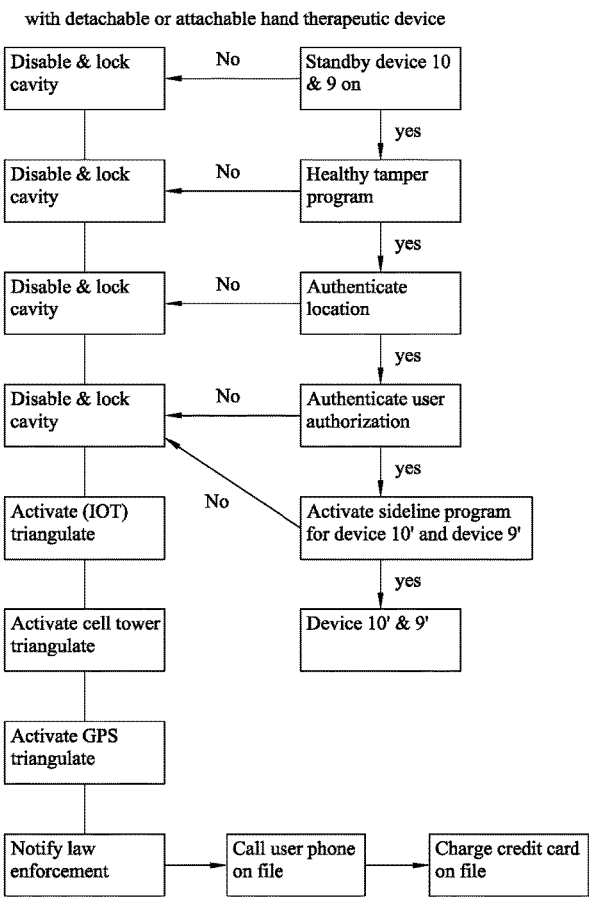
FIG. 42 is a schematic diagram illustrating the arrangement of the multi-task interactive electronic device and AR/VR device according to the preferred embodiment of the present invention.
Figure 43:
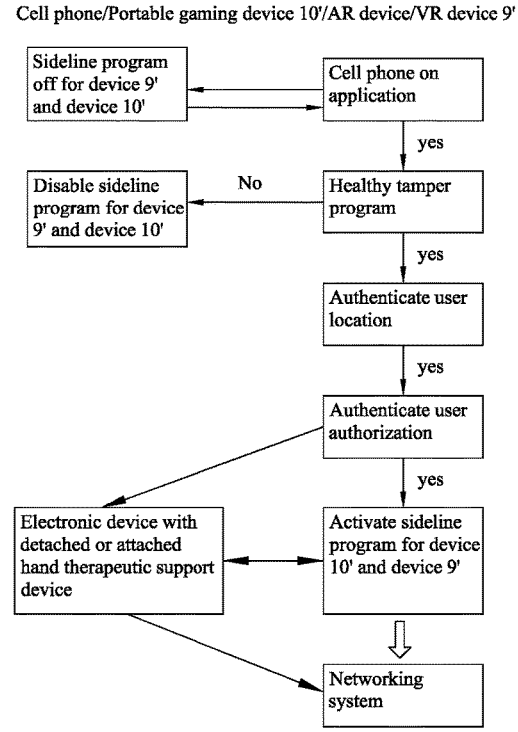
FIG. 43 is a flow chart illustrating the interacting of the smart cellular phone, the gaming electronic device and the AR/VR device according to the preferred embodiment of the present invention.
Figure 44:
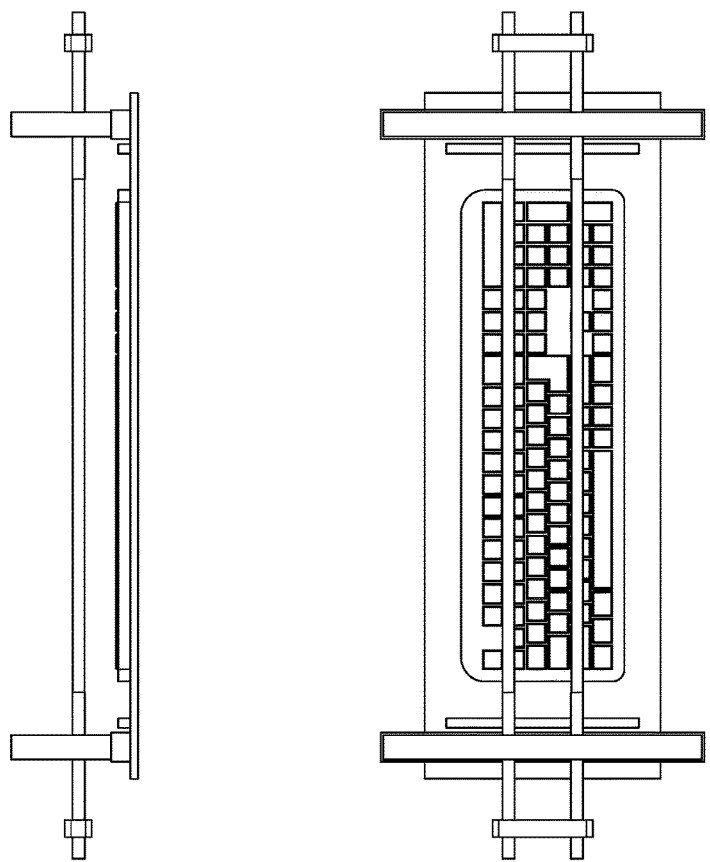
FIG. 44 illustrates a perspective view, an elevation view, a top view, and a side view of the hand support device as shown in FIG. 33A according to the another preferred embodiment of the present invention.
Figure 44:
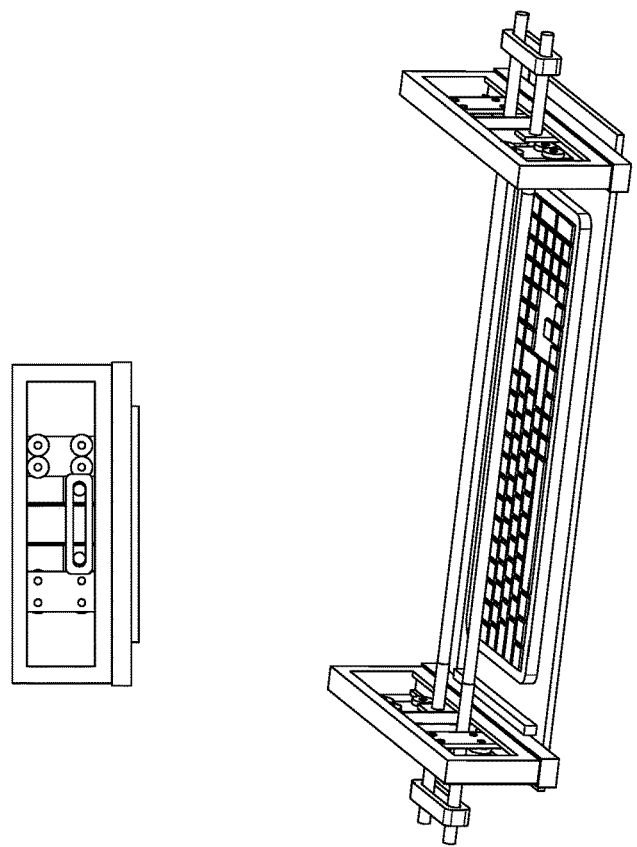

In particular, referring to FIGS. 41-43, the AR/VR device 9' can be interacts with electronic device with the detachable or attachable therapeutic hand support device 10' and the players or users. The player may see the display screen 12' and the control panel 26' and interact with the sidelines supported by the sideline program in the AR/VR device 9' for controlling and operating the game in the electronic device with the detachable or attachable therapeutic hand support device 10'. The user of the AR/VR device 9' is able to slide the sidelines 25' the same as in the physical portable electronic device with the detachable or attachable therapeutic hand support device 10'. Through the AR/VR device 9', the user may also be able to command through hand, finger, pupil, head motion, and voice command. The gaming electronic device with the detachable or attachable therapeutic hand support device 10', sideline program in the AR/VR device 9 and the smart phone of the user are interacted with each other forming the arrangement of operating multi-task interactive electronic devices of the present invention.

The AR/VR device 9' may also replace the physical portable gaming electronic device with the detachable or attachable therapeutic hand support device 10' by simply projecting an image as a simulated electronic device that also interacts with the sideline program and the smart phone of the user. In one embodiment, the AR/VR device 9' can be activated with the same security requirements for the sideline program by combination of the smart phone and the security system while maintaining the same disable function for the security tampering system as mentioned above for the physical portable gaming electronic device.

In one embodiment, the game program can be seen in the eye/head set of the AR/RV device 9' and the functions of the game are controlled in the AR/VR device 9' by the sideline program or vice versa. The player can have multiple sidelines 25' operating in the gaming electronic device with the detachable or attachable therapeutic hand support device 10' and in the AR/VR device 9' vice versa. The sideline program for the gaming electronic device with the detachable or attachable therapeutic hand support device 10' and the AR/VR device 9' can both be activated by voice command. In addition, the motion sensing camera 145' or 916' on the back side of the display screen 12' or on the back posterior occipital region of the AR/VR device 9' can provide the user a surround motion view of his/her location in the AR/VR device 9'. The gaming electronic device with the detachable or attachable therapeutic hand support device 10' can provide the AR/VR user surround sound and the ability for the user to also have a 360 view in his/her AR/VR device 9' through the use of the sideline program while the user is entertaining. The user is able to select what he or she wants to see on the display screen 12' of the electronic device with the detachable or attachable therapeutic hand support device 10' and what he or she wants on the AR/VR device 9' to include alert, message, game, confreres, amenities, and etc. In addition, the AR/VR device 9' may have the panic button 901' just like the gaming electronic device with the detachable or attachable therapeutic hand support device 10'.

In one embodiment, the AV/RV device 9' can be activated by the smart phone and or the gaming electronic device with the detachable or attachable therapeutic hand support device 10' and vice versa. In another embodiment, the smart phone, portable gaming electronic device with the detachable or attachable therapeutic hand support device 10' and the AR/VR device 9' once being activated can up load and down load into other interacting device(s) after the AV/RV device 9' and other portable gaming electronic devices with the detachable or attachable therapeutic hand support device 10' as a form of convenience without additional step in the sideline program security or may only be operated in a one AR/VR device 9' to one gaming electronic device system as a form to added security. The AR/VR device 9' may or may not continue to need the smart phone application authorization. The AR/VR device 9' is able to interact with the hologram while the light projection motion controls will provide the user the best entertainment of his/her life. For example, the AR user can have the holograph/light projection in the gaming electronic device with the detachable or attachable therapeutic hand support device 10' to provide an additional magical ambience as the user is playing on the gaming electronic device in the AR device and, with the portable gaming electronic device, the user can also use the touch screen in the VR device or vice versa. In another embodiment, as the panic button 901 is armed on the AR/VR device 9', the hologram and light projection on the gaming electronic device with the detachable or attachable therapeutic hand support device 10' will identify the location of the user to first responders. The AR/VR device 9' is an all-in-one device that the virtual reality (VR) can be control through the touch screen (display screen 12' and control panel 26') of the portable gaming electronic device. The VR device can also be removed and the AR device will activate in addition while the AR device can be turn off. Furthermore, the head set 911' of the AR/VR device 9' can continue provide the user a surround sound system and microphone interaction with the electronic portable electronic device with the detachable or attachable therapeutic hand support device 10'.

Figure 40A:
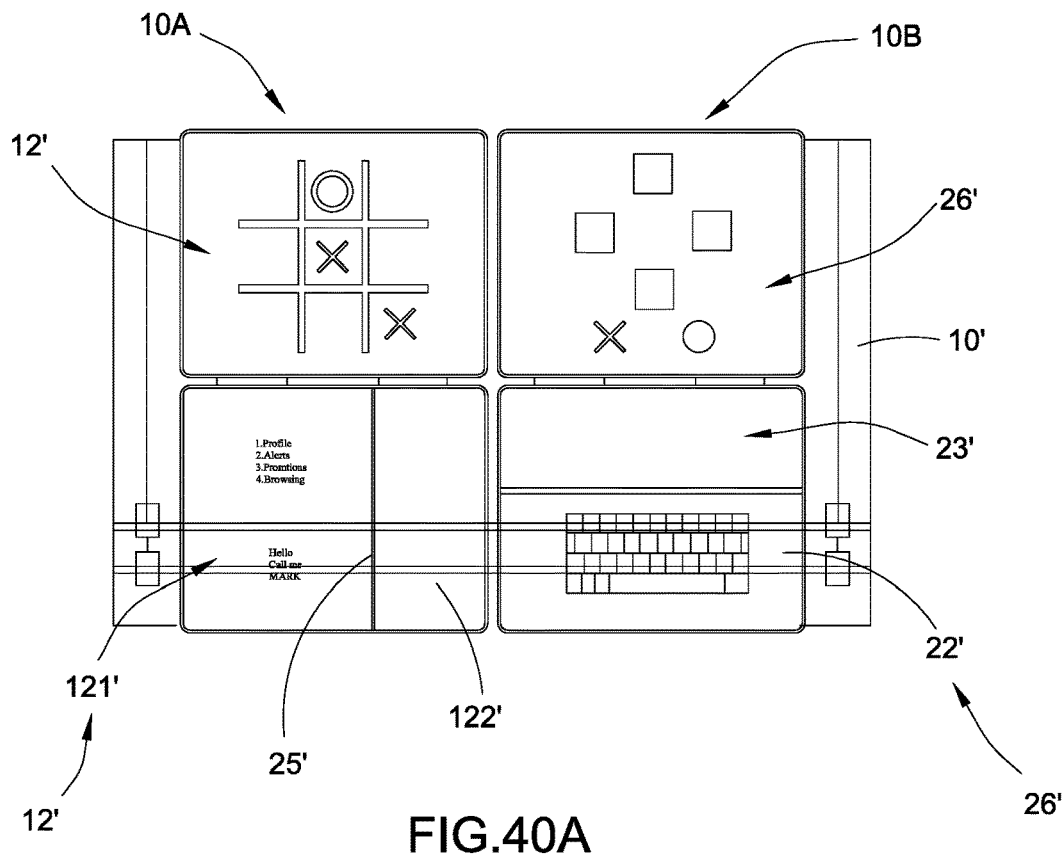
FIGS. 40A and 40B illustrate the usage of two electronic devices together according to the preferred embodiment of the present invention.
Figure 40B:
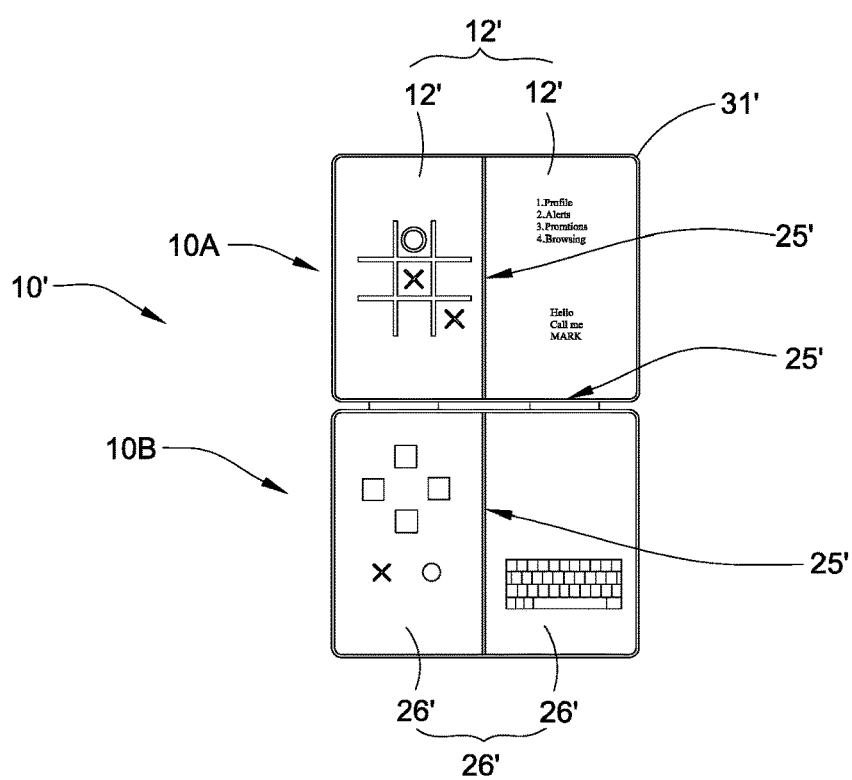

It is appreciated that the electronic device with the detachable or attachable therapeutic hand support device 10' as described in the above preferred embodiments according to the present invention is programmed to be able to be used with at least another electronic device with the detachable or attachable therapeutic hand support device 10' together. Referring to FIG. 40A, a first electronic device in FIG. 40A and a second electronic device in FIG. 40B are used side by side together and the user is able to configure them into an arrangement and link with the facility through the communication network, wherein four touch screens are present to arrange the display areas and input modules. The user may set the two touch screens of the electronic devices 40A' as two display screens 12' and the two touch screens of the electronic devices 10B as two control panels 26' to control and operate the first application and the second related application displayed on the two display screens 12' of the electronic device 40A' respectively. One or more sidelines 25' are also able to use to separate each of the two display screens 12 into two or more display areas 121', 122' and each of the two control panels 26' into two or more input modules 22', 23' to control and operate the games or applications displayed on the display areas 121', 122' respectively.

Referring to FIG. 40B, the first and second electronic devices in FIGS. 40A and 40B can be hinged together to form a single portable electronic device with the detachable or attachable therapeutic hand support device 10' as described in the above preferred embodiments with two display screens 12' and two control panels 26'. Accordingly, the two display screens 12' can be configured to form a combined display screen 12' and the two control panels 26' can be configured to form a combined control panel 26' and the boundary between the two electronic devices with the detachable or attachable therapeutic hand support devices 10A' and 10B' is set as sidelines 25' of the combined display screen 12' and the combined control panel 26' respectively.

It is worth mentioning that when the electronic device with the detachable or attachable therapeutic hand support device 10' is embodied as or interacted with the AV/VR device 9', the user is preferred to be educated or explained for how the sideline program and the sidelines operated with the AR/VR projections from the AV/VR device 9' that the user may view in accordance with present invention.

It is worth mentioning that the hand support device or the detachable or attachable therapeutic multi-task support device as illustrated in FIGS. 1 to 43 of the drawings according to the present invention can be permanently or detachably installed on an ergonomic standing and/or sitting up and down table system, such as a standing table converter, sit to stand up desk riser, height adjustable desk and the like. Where the ergonomic table surface can decline or incline independent of the hand support device and where both the table and the hand support device have installed with computer controlled device and corresponding APP or software for settings and functions mentioned in the present invention.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A hand support device for an input apparatus of an electronic device for providing assistance with repetitive fingers and wrists movements of a user while using the input apparatus, comprising:
   a hand supporting bridge unit comprising two elongated bars arranged in parallel across the input apparatus for supporting wrists of the user while using the input apparatus;
   a support base assembly configured to support said two elongated bars directly and parallelly over the input apparatus from a right side to a left side of the input apparatus for providing an upward and downward motion support, a left to right distance support, oblique angles left to right horizontal plane reaching support, and a bilateral vertical angular finger distant positioning support,
   the support base assembly comprising a first base unit and a second base unit, each having a height equal to or higher than the input apparatus, configured for arranging at a first side and a second side of the input apparatus; and
   a pillar and bar joint assembly comprising a first pillar and bar joint and a second pillar and bar joint respectively arranged at said first base unit and said second base unit, wherein first ends and second ends of said two elongated bars of said hand supporting bridge unit are supported by said first pillar and bar joint and said second pillar and bar joint respectively in such a manner that said two elongated bars bridge across said first base unit and said second base unit in a parallel manner and are capable of moving up and down while extending along a length of the input apparatus for the wrists of the user resting between said two elongated bars while using the input apparatus, such that hands of the user are able to hang down from the wrists supported by said two elongated bars of said hand supporting bridge unit to reach the input apparatus while providing a transversal support for volar medial, lateral ulnar and metacarpal regions of the wrists and flexor retinaculum, distal ulnar, radius anterior and lateral regions of the hands of the user over the input apparatus in a wrist support typing posture that the wrists of the user are supported by said two elongated bars enabling the hands hanging down from the wrists to reach the typing apparatus while the user is able to move fingers of the hands freely and naturally without stresses applied on the wrists.

2. The hand support device, as recited in claim 1, wherein said first base unit has a first guiding slot and said second base unit has a second guiding slot, wherein said first pillar and bar joint comprises two first bearing members and has two first bearing sockets mounted in said first guiding slot of said first base unit, and said second pillar and bar joint comprises two second bearing members and has two second bearing sockets mounted in said second guiding slot of said second base unit, wherein said first bearing members are respectively arranged at said first ends of said two elongated bars and mounted actively in two of said two first bearing sockets, wherein said two second bearing members are respectively arranged at said second ends of said two elongated bars and mounted actively in two of said two second bearing sockets, such that each of said first ends of said elongated bars is able to be rotated to move forward, backward, upward, and downward freely and independently, and that each of said second ends of said elongated bars is able to be rotated to move forward, backward, upward, and downward freely and independently, thereby the wrists of the user resting and being supported on said two elongated bars in the wrist supporting typing posture are able to move up-and-down and left-and-right above the input apparatus while the hands and fingers of the user are able to hang down from the wrists of the user.

3. The hand support device, as recited in claim 2, wherein said first guiding slot is formed in an inner side of said first base unit and has a first gear rail arranged at a bottom of said first guiding slot, wherein said second guiding slot is formed in an inner side of said second base unit and has a second gear rail arranged at a bottom of said second guiding slot, wherein a first periphery of each of said first bearing sockets matches to said first gear rail and a second periphery of each of said second bearing sockets matches to said second gear rail so as to allow said first bearing sockets with said first ends of said two elongated bars rotating forward and backward and allow said second bearing sockets with said second ends of said two elongated bars rotating forward and backward.

4. The hand support device, as recited in claim 3, wherein each of said first ends and second ends of said two elongated bars is able to lock at a predetermined position with respect to said first bearing sockets and said second bearing sockets respectively so as to maintain a predetermined fix separation between said two elongated bars.

5. The hand support device, as recited in claim 3, wherein said first ends of said two elongated bars are capable of selectively moving distally away from the user or moving proximally closer to the user, and said second ends of said two elongated bars are capable of selectively moving distally away from the user or moving proximally closer to the user.

6. The hand support device, as recited in claim 4, wherein said first ends of said two elongated bars are capable of selectively moving distally away from the user or moving proximally closer to the user, and said second ends of said two elongated bars are capable of selectively moving distally away from the user or moving proximally closer to the user.

7. The hand support device, as recited in claim 1, wherein said support base assembly and said pillar and bar joint assembly provide a rolling motion of each of said two elongated bars.

8. The hand support device, as recited in claim 6, wherein said support base assembly and said pillar and bar joint assembly provide a rolling motion of each of said two elongated bars.

9. The hand support device, as recited in claim 1, wherein said first base unit and said second base unit are configured to be adjustable in height so as to adjust a vertical parallel height between said two elongated bars of said hand supporting bridge unit.

10. The hand support device, as recited in claim 8, wherein said first base unit and said second base unit are configured to be adjustable in height so as to adjust a vertical parallel height between said two elongated bars of said hand supporting bridge unit.

11. The hand support device, as recited in claim 1, wherein said support base assembly further comprises a first swing pillar and a second swing pillar mounted rotatably at said first base unit and said second base unit respectively, wherein said two elongated bars are supported between said first swing pillar and said second swing pillar, wherein said first pillar and bar joint is arranged at said first swing pillar and said second pillar and bar joint is arranged at said second swing pillar, said first pillar and bar joint movably inserting said first ends of said two elongated bars into said first swing pillar and said second pillar and bar joint movably inserting said second ends of said two elongated bars into said second swing pillar.

12. The hand support device, as recited in claim 11, wherein said support base assembly further comprises a first rotation and fix component and a second rotation and fix component, wherein said first swing pillar is mounted at said first base unit in a swing manner by said first rotation and fix component and said second swing pillar is mounted at said second base unit in a swing manner by said second rotation and fix component, such that said first swing pillar and said second swing pillar are rotatable to a predetermined position to enable a surface of each of said elongated bars defined having a predetermined angle with respect to the input apparatus, and that when said first swing pillar and said second swing pillar rotate at another predetermined position, said first rotation and fix component and said second rotation and fix component are locked for rotation.

13. The hand support device, as recited in claim 3, wherein said support base assembly further comprises a first swing pillar and a second swing pillar mounted rotatably at said first base unit and said second base unit respectively, wherein said two elongated bars are supported between said first swing pillar and said second swing pillar, wherein said first pillar and bar joint is arranged at said first swing pillar and said second pillar and bar joint is arranged at said second swing pillar, said first pillar and bar joint movably inserting said first ends of said two elongated bars into said first swing pillar and said second pillar and bar joint movably inserting said second ends of said two elongated bars into said second swing pillar, wherein said first guiding slot with said first gear rail is defined at said first swing pillar and said second guiding slot with said second gear rail is defined at said second swing pillar, wherein said first periphery of said first bearing socket couples with said first gear rail and said second periphery of said second bearing socket couples with said second gear rail so as to mount said first ends and said second ends of said two elongated bars movably in relative to said first swing pillar and said second swing pillar respectively.

14. The hand support device, as recited in claim 13, wherein said support base assembly further comprises a first rotation and fix component and a second rotation and fix component, wherein said first swing pillar is mounted at said first base unit in a swing manner by said first rotation and fix component and said second swing pillar is mounted at said second base unit in a swing manner by said second rotation and fix component, such that said first swing pillar and said second swing pillar are rotatable to a predetermined position to enable a surface of each of said elongated bars defined having a predetermined angle with respect to the input apparatus, and that when said first swing pillar and said second swing pillar rotate at another predetermined position, said first rotation and fix component and second rotation and fix component are locked for rotation.

15. The hand support device, as recited in claim 1, further comprising a mid-bar divider which comprises a first mid-bar divider and a second mid-bar divider, wherein said first mid-bar divider and said second mid-bar divider are arranged to slide with each other, wherein each of said two elongated bars has a first half bar and a second half bar, wherein said first half bars of said two elongated bars extend between said first base unit and said first mid-bar divider, and said second half bars of said two elongated bars extend between said second base unit and said second mid-bar divider.

16. The hand support device, as recited in claim 3, further comprising a mid-bar divider which comprises a first mid-bar divider and a second mid-bar divider, wherein said first mid-bar divider and said second mid-bar divider are arranged to slide with each other, wherein each of said two elongated bars has a first half bar and a second half bar, wherein said first half bars of said two elongated bars extend between said first base unit and said first mid-bar divider, and said second half bars of said two elongated bars extend between said second base unit and said second mid-bar divider, wherein said mid-bar divider and said second mid-bar divider have opposite frictionless surfaces parallel to each other.

17. The hand support device, as recited in claim 11, further comprising a mid-bar divider which comprises a first mid-bar divider and a second mid-bar divider, wherein said first mid-bar divider and said second mid-bar divider are arranged to slide with each other, wherein each of said two elongated bars has a first half bar and a second half bar, wherein said first half bars of said two elongated bars extend between said first base unit and said first mid-bar divider, and said second half bars of said two elongated bars extend between said second base unit and said second mid-bar divider.

18. The hand support device, as recited in claim 14, further comprising a mid-bar divider which comprises a first mid-bar divider and a second mid-bar divider, wherein said first mid-bar divider and said second mid-bar divider are arranged to slide with each other, wherein each of said two elongated bars has a first half bar and a second half bar, wherein said first half bars of said two elongated bars extend between said first base unit and said first mid-bar divider, and said second half bars of said two elongated bars extend between said second base unit and said second mid-bar divider, wherein said first mid-bar divider and said second mid-bar divider have opposite frictionless surfaces parallel to each other.

19. The hand support device, as recited in claim 1, further comprising a base assembly which comprises a first base, a second base and a back brace supporting said first base and said second base for arranging a first side and a second of the input apparatus, wherein said back brace has a thickness ranging from $1/16$ inch to 2 inches, a length ranging from 1 inch to 38 inches, and a width ranging from 1 inch to 18 inches, wherein said first base unit movably sits on said first base and said second base unit movably sit on said second base.

20. The hand support device, as recited in claim 19, wherein each of said elongated bars has a diameter ranging from $1/16$ inch to 3 inches, wherein said two elongated bars are adjustable in relation to each other.

21. The hand support device, as recited in claim 20, further comprising a plurality of sleeves provided on said two elongated bars in a movable manner, wherein a diameter of each of said sleeves is larger than that of each of said two elongated bars, thereby said sleeves provide additional comfort, therapeutic, and health benefits to the user, wherein said two or more elongated bars and said plurality of sleeves have adjustable functions and are replaceable.

22. The hand support device, as recited in claim 21, further comprising a mount place adapted for the input apparatus to be disposed thereon and one or more universal clips provided on said mount plate for affixing the input apparatus in position on said mount plate, wherein said first base unit and said second base unit are coupled at two sides of said mount plate while said mount plate and said one or more universal clips are adjustable.

23. The hand support device, as recited in claim 22, wherein each of said two elongated bars has a length ranging from 1 inch to 38 inches, wherein a length adjustment of each of said two elongated bars is independent from a height adjustment of each of said first base unit and said second base unit, wherein said height adjustment of each of said first base unit and said second base unit is independent from function adjustments of said plurality of sleeves, wherein the function adjustments of said plurality of sleeves are independent from up and down gradient adjustments of said first base, wherein said up and down gradient adjustments of said first base are independent from adjustments of said mount plate, wherein said adjustments of said mount plate are independent from adjustments of said one or more universal clips.

* * * * *